(12) United States Patent
Yocum et al.

(10) Patent No.: US 7,858,335 B2
(45) Date of Patent: Dec. 28, 2010

(54) MICROORGANISMS AND ASSAYS FOR THE IDENTIFICATION OF ANTIBIOTICS

(75) Inventors: R. Rogers Yocum, Lexington, MA (US); Thomas A. Patterson, North Attleboro, MA (US)

(73) Assignee: OmniGene Bioproducts, Inc., Woburn, MA (US)

( * ) Notice: Subject to any disclaimer, the term of this patent is extended or adjusted under 35 U.S.C. 154(b) by 272 days.

(21) Appl. No.: 11/709,370

(22) Filed: Feb. 22, 2007

(65) Prior Publication Data

US 2008/0160551 A1 Jul. 3, 2008

Related U.S. Application Data

(62) Division of application No. 11/011,979, filed on Dec. 13, 2004, now abandoned, which is a division of application No. 09/813,453, filed on Mar. 20, 2001, now Pat. No. 6,830,898.

(60) Provisional application No. 60/227,860, filed on Aug. 24, 2000.

(51) Int. Cl.
| | |
|---|---|
| *C12Q 1/02* | (2006.01) |
| *C12P 21/00* | (2006.01) |
| *C12N 9/00* | (2006.01) |
| *C12N 1/20* | (2006.01) |
| *C12N 15/09* | (2006.01) |
| *C07H 21/00* | (2006.01) |

(52) U.S. Cl. ........................ 435/29; 435/183; 435/71.1; 435/252.3; 435/320.1; 536/23.2; 536/23.7

(58) Field of Classification Search ........................ None
See application file for complete search history.

(56) References Cited

FOREIGN PATENT DOCUMENTS

| WO | WO-01/21772 A2 | 3/2001 |
| WO | WO-01/49721 A2 | 7/2001 |

OTHER PUBLICATIONS

Bowie et al., "Deciphering the Message in Protein Sequences: Tolerance to Amino Acid Substitutions," Science, vol. 247 No. 4948, pp. 1306-1310 (Mar. 1990).*
Calder, Robert B. et al., "Cloning and Characterization of a Eukaryotic Pantothenate Kinase Gene (*panK*) from *Aspergillus nidulans*," The Journal of Biological Chemistry, vol. 274(4):2014-2020 (1999).
DeShazer, David et al., "Identification of a *Bordetella pertussis* Regulatory Factor Required for Transcription of the Pertussis Toxin Operon in *Escherichia coli*," Journal of Bacteriology, vol. 177(13):3801-3807 (1995).
Dunn, Stanley et al., "Isolation and Temperature-Sensitive Pantothenate Kinase Mutants of *Salmonella typhimurium* and Mapping of the *coaA* Gene," Journal of Bacteriology, vol. 140(3):805-808 (1979).
Flamm, Jason A. et al., "The nucleotide sequence of the *Escherichia coli rts* gene," Gene, vol. 74:555-558 (1988).
GenBank Accession No. AAB64970, Dietrich, F.S. et al., "The sequence of *Saccharomyces cerevisiae* chromosome IV right," (2002).
GenBank Accession No. U12020, DeShazer, D. et al., "Identification of a Bordetella pertussis regulatory factor required for transcription of the pertussis toxin operon in *Escherichia coli*," J. Bacteriol., vol. 177(13):3801-3807 (1995).
Rock, Charles O. et al., "Pantothenate Kinase Regulation of the Intracellular Concentration of Coenzyme A," The Journal of Biological Chemistry, vol. 275(2):1377-1383 (2000).
Song, Woo-Joo et al., "Cloning, Sequencing, and Expression of the Pantothenate Kinase (*coaA*) Gene of *Escherichia coli*," Journal of Bacteriology, vol. 174(20):6411-6417 (1992).
Trias, Joaquim et al., "Innovative approaches to novel antibacterial drug discovery," Current Opinion in Biotechnology, vol. 8:757-762 (1997).
Vallari, David S. et al., "Isolation and Characterization of Temperature-Sensitive Pantothenate Kinase (*coaA*) Mutants of *Escherichia coli*," Journal of Bacteriology, vol. 169(12):5795-5800 (1987).
Wood, Gwendolyn E. et al., "The Bvg accessory factor (Baf) enhances pertussis toxin expression in *Escherichia coli* and is essential for *Bordetella pertussis* viability," FEMS Microbiology Letters, vol. 193(1):25-30 (2000).
Wood, G.E. et al., "The effect of the Bvg accessory factor (Baf) on the expression of pertussis toxin in *Bordetella pertussis* and *Escherichia coli* and on the viability of *B. pertussis*," Abstracts of the General Meeting of the American Society for Microbiology May 1997; Abstr. B-349.

* cited by examiner

*Primary Examiner*—Zachariah Lucas
(74) *Attorney, Agent, or Firm*—Nelson Mullins Riley & Scarborough LLP; Debra J. Milasincic, Esq.

(57) ABSTRACT

The present invention features methods for the identification of compounds and compositions useful as antibiotics and antibacterial agents. In particular, the invention features methods for the identification of modulators of a previously unidentified target protein, termed CoaX. High-throughput assay systems are featured as well as assay kits for the identification of CoaX modulators. Also featured are coaX nucleic acid molecules and purified CoaX proteins, as well as recombinant vectors and microorganisms including the gene, coaX.

22 Claims, 13 Drawing Sheets

FIG. 6A

CLUSTAL W (1.7) Multiple Sequence Alignments

Sequence type explicity set to Protein
Seqnuce format is Pearson

```
sp     | B. subtilis |CoaX (SEQ ID NO:2)                         258 aa
dbj    | BAA21476.1 | D. vulgaris (SEQ ID NO:59)                 212 aa
gb     | AAD35964.1 | T. maritima (SEQ ID NO:9)                  246 aa
pir    | T36391    | S. coelicolor (SEQ ID NO:4)                 265 aa
sp     | Q45338    | B. pertussis (SEQ ID NO:15)                 267 aa
sp     | O06282    | M. tuberculosis (SEQ ID NO:5)               272 aa
gb     | O93446    | T. pallidum (SEQ ID NO:10)                  273 aa sp     | O51477    | B. burgdorferi (SEQ ID NO:11)               262 aa
sp     | P74045    | Synechocystis (SEQ ID NO:13)                257 aa
sp     | O25533    | H. pylori (SEQ ID NOs:14 or 67)             223 aa
sp     | O67753    | A. aeolicus (SEQ ID NO:12)                  229 aa
sp     | Q9RX54    | D. radiodurans (SEQ ID NO:8)                262 aa
WIT    | RCA03301| C. acetobutylicum (SEQ ID NO:3)               250 aa
WIT    | RRC02473 | R. capsulatus (SEQ ID NO:6)                  258 aa B. subtilis |CoaX (SEQ ID NO:2)           ----------------MLLVIDVGNTNTVLGVYHDG----KLEYHWRIE
WIT    | RCA03301| C. acetobutylicum (SEQ ID NO:3)   NKRAAFMLLFLRSVLKVILVLDVGNTNIVLGIYNDT----KLTAEWRLS
pir    | T36391 | S. coelicolor (SEQ ID NO:4)       ----------------MLLTIDVGNTHTVLGLFDGE----DIVEHWRIS
sp     | O06282 | M. tuberculosis (SEQ ID NO:5)     ----------------MLAIDVRNTHTVGLLSGMKEHAKVVQQWRIR
WIT    | RRC02473 | R. capsulatus (SEQ ID NO:6)     ----------------MLLCIDCGNTNTVFSVWDGT----DFAATWRIA
dbj    | BAA21476.1 | D. vulgaris (SEQ ID NO:59)    -----------MTQHFLLFDIGNTNVKIGIAVET----AVLTSYVLP
sp     | Q9RX54 | D. radiodurans (SEQ ID NO:8)      -----------MPAFPLLAVDIGNTTTVLGLADASG----ALTHTWRIR
gb     | AAD35964.1 | T. maritima (SEQ ID NO:9)     -----------MYLLVDVGNTHSVFSITEDG----KTFRRWRLS
gb     | O93446 | T. pallidum (SEQ ID NO:10)        ----------MLLIDVGNSHVVFGIQGENGGRVCVRELFRLA
sp     | O51477 | B. burgdorferi (SEQ ID NO:11)     MNKPLLSELIIDIGNTSIAFALFKDN----QVNLFIKMK
sp     | O67753 | A. aeolicus (SEQ ID NO:12)        -----------MRFLTVDVGNSSVDIALWEGK----KVK
sp     | P74045 | Synechocystis (SEQ ID NO:13)      METSKPGCGLALDNDKQKPWLGLMIGN----SRLHWAYC
sp     | O25533 | H. pylori (SEQ ID NOs:14 or 67)   -----------MPARQSFTDLKN---LVLCDIGN----------TR
sp     | Q45338 | B. pertussis (SEQ ID NO:15)       ----------MILIDSGNSRLKVGWFDPDAP---QAAREPAPV
```

FIG. 6B

```
B. subtilis |CoaX (SEQ ID NO:2)                           TSRHKTEDEFGMILRSLFDHS----GLMFEQIDGIIISSVVPPIMFALER
WIT|RCA03301| C. acetobutylicum (SEQ ID NO:3)             TDVLRSADEYGIQVMNLFQQD----KLDPTLVEGVIISSVVPNIMYSLEH
pir|T36391 | S. coelicolor (SEQ ID NO:4)                  TDSRRTADELAVLLQGLMGMHPLLGDELGDGIDGIAICATVPSVLHELRE
sp |006282 | M. tuberculosis (SEQ ID NO:5)                TESEVTADELALTIDGLIG------EDSERLTGTAALSTVPSVLHEVRI
WIT|RRC02473 | R. capsulatus (SEQ ID NO:6)                TDHRRTADEYFVWLNTLMQLK----GLQGRISEAIISSTAPRVVFNLRV
dbj|BAA21476.1 | D. vulgaris (SEQ ID NO:59)               TDPGQTTDSIGLRLLEVLRHAG----LGPADVGACVASSVVPGVNPLIRR
sp |Q9RX54 | D. radiodurans (SEQ ID NO:8)                 TNREMLPDDLALQLHGLFTLA----GAP-IPRAAVLSSVAPPVGENYAL
gb |AAD35964.1 | T. maritima (SEQ ID NO:9)                TGVFQTEDELFSHLHPLLG------DAMREIKGIGVASVVPTQNTVIER
sp |093446 | T. pallidum (SEQ ID NO:10)                   PDARKTQDEYSLLIHALCERAG----VGRASLRDAFISSVVPVLTKTIAD
sp |051477 | B. burgdorferi (SEQ ID NO:11)                TNLMLRYDEVYSFFEENFDFN-----VN---K--VFISSVVPILNETFKN
sp |067753 | A. aeolicus (SEQ ID NO:12)                   DFLKLSHEEFLKEEFPKLK-----------------ALGISVKQSFSEKVRG
P74045 | Synechocystis (SEQ ID NO:13)                     SGNAPLQTWTDYNPKSAQLP---------------VLLGKVPLMLASVVPE
sp |025533 | H. pylori (SEQ ID NOs:14 or 67)              IHFAQNYQLFSSAKEDLKR-----------------LGIQKEIFYISVNEE
sp |Q45338 | B. pertussis (SEQ ID NO:15)                  AFDNLDLDALGRWLATLPRRP---------Q-----RALGVNAGLARGEAIA B. subtilis |CoaX (SEQ ID NO:2)                           MCTKYFHIEPQIVG-PG-MKTGLNIKYDNPKEVGADRIVNAVAAIHLYG-
WIT|RCA03301| C. acetobutylicum (SEQ ID NO:3)             MIRKYFKINPLVVG-PG-IKTGINIKYDNPKEVGADRIVNAVAAHEIYK-
pir|T36391 | S. coelicolor (SEQ ID NO:4)                  VTRRYYGDVPAVLVEPG-VKTGVPILTDHPKEVGADRIINAVAAVELYG-
sp |006282 | M. tuberculosis (SEQ ID NO:5)                MLDQYWPSVPHVLIEPG-VRTGIPLLVDNPKEVGADRIVNCLAAYDRFR.
WIT|RRC02473 | R. capsulatus (SEQ ID NO:6)                LCNRYFDCRPYVVGKPG-CELPVAPRVDPGTTVGPDRLVNTVAGYDREG-
dbj|BAA21476.1 | D. vulgaris (SEQ ID NO:59)               ACERYL--YRKLLFAPGDIAIPLDNRYERPAEVGADRLVAAYAARRLYP-
sp |Q9RX54 | D. radiodurans (SEQ ID NO:8)                 ALKRHFMIDAFAVSAEN--LPDVTVELDTPGSVGADRLCNLFGAEKYLG-
gb |AAD35964.1 | T. maritima (SEQ ID NO:9)                FSQKYFHISPIWVKAKN--GCVKWNVKNPSEVGADRVANVAFVKFEYG-
sp |093446 | T. pallidum (SEQ ID NO:10)                   AVAQISGVQPVVFGPWAYEHIPVRIPEPVRAEIGTDLVANAVAAYVHFR-
sp |051477 | B. burgdorferi (SEQ ID NO:11)                VIPSFFKIKPLFIGFDLNYDLTFNPYKSDKFLLGSDVFANLVAAIENYS-
sp |067753 | A. aeolicus (SEQ ID NO:12)                   KIPKIK------FLKKEN-----FPIQVDYKTPETLGTDRVALAYSAKKFYG-
P74045 | Synechocystis (SEQ ID NO:13)                     QTEVWRVYQPKILTLKN-----LPLVNLYP---SFGIDRALAGLGTLTVG-
sp |025533 | H. pylori (SEQ ID NOs:14 or 67)              NEKALLNCYPNAKNLAG---FFHLETDYVG---LGIDRQMACLA---VN--
sp |Q45338 | B. pertussis (SEQ ID NO:15)                  ATLRAGGCDIRWLRAQP-LAMGLRNGYRNPDQLGADRWACMVGVLARQPS
                                                                                                    * *
```

FIG. 6C

| | | |
|---|---|---|
| B. subtilis \|CoaX (SEQ ID NO:2) | NP-- | LIVVDFGTATTYCYIDENKQYMGAIAPGITISTEALYSRAAKLPR |
| WIT\|RCA03301\| C. acetobutylicum (SEQ ID NO:3) | RS-- | LIIIDFGTATTFCAVRENGDYLGGAICPGIKVSSEALFEKAAKLPR |
| pir\|T36391\| S. coelicolor (SEQ ID NO:4) | GP-- | AIVVDFGTATTFDAVSARGEYIGGVIAPGIEISVEALGVKGAQLRK |
| sp\|006282\| M. tuberculosis (SEQ ID NO:5) | KA-- | AIVVDFGSSICVDVVSAKGEFLGGAIAPGVQVSSDAAARSAALRR |
| WIT\|RRC02473\| R. capsulatus (SEQ ID NO:6) | GD-- | LIVVDFGTATTFDVVAPDGAYIGGVIAPGVNLSLEALHMAAAALPH |
| dbj\|BAA21476.1\| D. vulgaris (SEQ ID NO:59) | GPRSLVSVDFGTATTFDCVEG- | GAYLGGLICPGVLSSAGALSSRTAKLPR |
| sp\|Q9RX54\| D. radiodurans (SEQ ID NO:8) | GLDYAVVVDFGTSTNFDVVGRGRRFLGGILATGAQVSADALFARAAKLPR | |
| gb\|AAD35964.1\| T. maritima (SEQ ID NO:9) | KN-- | GIIIDMGTATTVDLVVN-GSYEGGAILPGFFMVHSLFRGTAKLPL |
| gb\|093446\| T. pallidum (SEQ ID NO:10) | SA-- | CVVVDCGTALTFTAVDGTGLIQGVAIAPGLRTAVQSLHTGTAQLPL |
| gb\|051477\| B. burgdorferi (SEQ ID NO:11) | FEN-- | VLVVDLGTACTIFAVSRQDGILGGIINSGPLINFNSLHDNAYLIKK |
| sp\|067753\| A. aeolicus (SEQ ID NO:12) | KN-- | VVVISAGTALVIDLVLE-GKFKGGFITLGLGKKLKILSDLAEGIPE |
| sp\|P74045\| Synechocystis (SEQ ID NO:13) | FP-- | CLVVDGGTALTITGFDQDKKLVGGAILPGLGLQLATLGDRLAALPK |
| sp\|025533\| H. pylori (SEQ ID NOs:14 or 67) | NG-- | VVVDAGSAITIDLIKE-GKHLGGCILPGLAQYIHAYKKSAKILEQ |
| sp\|Q45338\| B. pertussis (SEQ ID NO:15) | VHPPLLVASFGTATTLDTIGPDNVFPGGLILPGPAAMRGALAYGTAHLPL | |
| | : *:: . * . * * * |
| | |
| B. subtilis \|CoaX (SEQ ID NO:2) | IEITTRPDN---IIGKNTVSAMQSGILFGYVGQVEGIVKRMKWQAKQDLK- |
| WIT\|RCA03301\| C. acetobutylicum (SEQ ID NO:3) | VELIKPAY---AICKNTISSIQSGIVYRYLRQVTKYLFEKLKENLPDGRRT |
| pir\|T36391\| S. coelicolor (SEQ ID NO:4) | IEVARPRS---VIGKNTVEAMQSGIVYGFAGQVDGVVNRMARELADD--P |
| sp\|006282\| M. tuberculosis (SEQ ID NO:5) | VELARPRS---VVGKNTVECMQAGAVFGFAGLVDGLVGRIREDVSGFSVD |
| WIT\|RRC02473\| R. capsulatus (SEQ ID NO:6) | VDVTKPQG---VIGTNTVACIQSGVVWGYIGLVEGIVRQIRMERDRP--- |
| dbj\|BAA21476.1\| D. vulgaris (SEQ ID NO:59) | ISLEVEEDS-PVIGRSTTTSLNHGFIFGFAAMTEGVLAA----------- |
| sp\|Q9RX54\| D. radiodurans (SEQ ID NO:8) | ITLQAPET---AIGKNTVHALQSGLVFGYAEMVDGLLRRIRAELPGE--- |
| gb\|AAD35964.1\| T. maritima (SEQ ID NO:9) | VEVKPADF---VVGKDTEENIRLGVVNGSVYALEGIIGRIKEVYGDLP-- |
| gb\|093446\| T. pallidum (SEQ ID NO:10) | VPLALPDS---VLGKDTTHAVQAGVVRGTLFVIRAMIAQCQKELGCR--- |
| gb\|051477\| B. burgdorferi (SEQ ID NO:11) | FPISTPNN---LLERTTSGSVNSLFYQYKLIEGVTRDIKQMYKKK----- |
| sp\|067753\| A. aeolicus (SEQ ID NO:12) | FFPEEVEI---FLGRSTRECVLGGAYRESTEFIKSTLKLWRKVFKRK--- |
| sp\|P74045\| Synechocystis (SEQ ID NO:13) | LEMDQLTELPDRWALDTPSAIFSGVVYGVLGALQSYLQDWQKLFPGA--- |
| sp\|025533\| H. pylori (SEQ ID NOs:14 or 67) | PFKALDSL--EVLPKSTRDAVNYGMVLSVIACIQHLAK--NQK------- |
| sp\|Q45338\| B. pertussis (SEQ ID NO:15) | ADGLVADY----PIDTHQAIASGLAAAQAGAIVRQWLAGRQRYGQAP--- |
| | * . * |

FIG. 6D

```
B. subtilis |CoaX (SEQ ID NO:2)                          ----VIATGG-------LAPLIANES------DCIDIVDPFLTLKGLELI
WIT|RCA03301| C. acetobutylicum (SEQ ID NO:3)            RTSLVLATGG-------LAKLIN-----------------------
pir|T36391| S. coelicolor (SEQ ID NO:4)                  DDVTVIATGG-------LAPMVLGES-------SVIDEHEPWLTLMGLRLV
sp|O06282|M. tuberculosis (SEQ ID NO:5)                  HDVAIVATGH-------TAPLLLPEL-------HTVDHYDQHLTLQGLRLV
WIT|RRC02473| R. capsulatus (SEQ ID NO:6)                --MKVIATGG-------LASLFDLGF-------DLFDKVEDDLTMHGLRLI
dbj|BAA21476.1| D. vulgaris (SEQ ID NO:59)               ---------------------------------------------
sp|Q9RX54| D. radiodurans (SEQ ID NO:8)                  --AVAVATGG-------FSRTVQGIC-------QEIDYDETLTLRGLIVEL
gb|AAD35964.1| T. maritima (SEQ ID NO:9)                 ----VVLTGG-------QSKIVK-DM-------IKHEIFDEDLTIKGVYHF
gb|O93446| T. pallidum (SEQ ID NO:10)                    ---CAAVITGG------LSRLFS-SE-------VDFPPIDAQLTLSGLAHI
gb|O51477| B. burgdorferi (SEQ ID NO:11)                 ---FNLIITGG------NADLILSLI-------EIEFIFNIHLTVEGVRIL
sp|O67753| A. aeolicus (SEQ ID NO:12)                    ---FKVVITGG------EGKYFS----------KFGIYDPLLVHRGMRNL
sp|P74045| Synechocystis (SEQ ID NO:13)                  ---AMVITGG-------DGKILHGFLKEHSPNLSVAWDDNLIFLGMAAI
sp|O25533| H. pylori (SEQ ID NOs:14 or 67)               ----IYLCGG-------DAKYLSAFL-------PHSVCKERLVFDGMEIA
sp|Q45338| B. pertussis (SEQ ID NO:15)                   ---EIYVAGGWPEVRQEAERLLAVTGAAFGATPQPTYLDSPVLDGLAAL B. subtilis |CoaX (SEQ ID NO:2)                          YERNRVGSV-----------
WIT|RCA03301| C. acetobutylicum (SEQ ID NO:3)            --------------------
pir|T36391| S. coelicolor (SEQ ID NO:4)                  YERNVSRM------------
sp|O06282|M. tuberculosis (SEQ ID NO:5)                  FERNLEVQRGRLKTAR----
WIT|RRC02473| R. capsulatus (SEQ ID NO:6)                FDYNKGLGA-----------
dbj|BAA21476.1| D. vulgaris (SEQ ID NO:59)               WASRSEVR------------
sp|Q9RX54| D. radiodurans (SEQ ID NO:8)                  CFGD----------------
gb|AAD35964.1| T. maritima (SEQ ID NO:9)                 ARLVPTSLLPPATVSGSSGN
gb|O93446| T. pallidum (SEQ ID NO:10)                    GNSIDFKFVN----------
gb|O51477| B. burgdorferi (SEQ ID NO:11)                 LYLYHRI-------------
sp|O67753| A. aeolicus (SEQ ID NO:12)                    HHGDRPIC------------
sp|P74045| Synechocystis (SEQ ID NO:13)                  LKKAGILECK----------
sp|O25533| H. pylori (SEQ ID NOs:14 or 67)               --------------------
sp|Q45338| B. pertussis (SEQ ID NO:15)                   AAQGAPTA------------
```

US 7,858,335 B2

MICROORGANISMS AND ASSAYS FOR THE IDENTIFICATION OF ANTIBIOTICS

RELATED APPLICATIONS

This application is a divisional application of U.S. patent application Ser. No. 11/011,979, entitled "Microorganisms and Assays for the Identification of Antibiotics", filed Dec. 13, 2004, (abandoned), which is a divisional application of U.S. patent application Ser. No. 09/813,453, entitled "Microorganisms and Assays for the Identification of Antibiotics" filed Mar. 20, 2001, now U.S. Pat. No. 6,830,898B2, which claims the benefit of prior filed provisional U.S. Patent Application Ser. No. 60/227,860, entitled "Novel Microbial Pantothenate Kinase Gene and Methods of Use", filed Aug. 24, 2000, which is also related to U.S. patent application Ser. No. 09/667,569, entitled "Methods and Microorganisms for Production of Panto-Compounds", filed Sep. 21, 2000. The entire contents of the above-referenced patent applications are incorporated herein by this reference.

BACKGROUND OF THE INVENTION

Antimicrobial or antibiotic treatment is a well-accepted therapy for fighting microbial infections that takes advantage of the existence of biological processes that are unique to bacteria or fungi that can be safely inhibited to the detriment of the bacteria, without producing undesired or harmful side effects in the individual receiving such therapy. However, due at least in part to the continual evolution of microbial resistance to the available classes of antibiotics, and in part to the recent slowdown in the introduction of novel antimicrobials to market, there exists a need for the development of screening assays that target previously unexploited biochemical systems in microbes. In particular, there exists the need for the identification of new bacterial targets for use in drug discover programs designed to identify agents having potential use as anti-infective agents with novel modes of actions.

SUMMARY OF THE INVENTION

The present invention is based at least in part, on the identification of a novel target for use in screening assays designed to identify antimicrobial agents. In particular, the present invention is based on the identification and characterization of a previously unidentified microbial pantothenate kinase gene, coaX. The coaX gene was first identified in *B. subtilis* where it is one of two genes encoding functional pantothenate kinase. Initially the present inventors identified and cloned the *B. subtilis* coaA gene (previously termed yqjs) that encodes a pantothenate kinase homologous to the CoaA enzyme previously characterized in *E. coli*. A second gene (previously termed yacB) has also been identified and cloned by the present inventors that is not homologous to any previously described pantothenate kinase. This latter pantothenate kinase-encoding gene has been renamed coaX. The coaX gene could be deleted from *B. subtilis* strains with an intact coaA gene, but it could not be deleted from a strain containing a deletion in the coaA gene, indicating that the coaX gene is not essential in *B. subtilis* strains with a wild-type coaA gene. Homologs of the coaX gene can be found in a number of bacterial species, including but not limited to *Aquifex aeolicus, Bacillus anthracis, Bacillus halodurans, Bacillus stearothermophilus, Caulobacter crescentus, Chlorobium tepidum, Clostridium acetobutylicum, Dehalococcoides ethenogenes, Deinococcus radiodurans, Desulfovibrio vulgaris, Geobacter sulfurreducens, Pseudomonas putida, Rhodobacter capsulatus, Thiobacillus ferrooxidans, Streptomyces coelicolor, Synechocystis* sp., *Thermotoga maritima, Bordetella pertussis, Borrelia burgdorferi, Campylobacter jejuni, Clostridium difficile, Helicobacter pylori, Neisseria meningitidis, Neisseria gonorrhoeae, Porphyromonas gingivalis, Pseudomonas aeruginosa, Pseudomonas syringae pv tomato, Treponema pallidum, Xylella fastidiosa* and *Mycobacterium tuberculosis*. More importantly, however, this novel pantothenate kinase gene has been found to be the sole essential pantothenate kinase in troublesome pathogens including, but not limited to, *Bordetella pertussis, Borrelia burgdorferi, Campylobacter jejuni, Helicobacter pylori, Neisseria meningitidis, Pseudomonas aeruginosa, Treponema pallidum* and *Xylella fastidiosa*. Accordingly, the coaX gene represents an attractive target for screening for new antibacterial compounds to combat these pathogenic microorganisms, particularly microorganisms in which coaX is the sole pantothenate kinase-encoding gene.

Accordingly, the present invention features isolated CoaX proteins, in particular, proteins encoded by the coaX gene in bacteria. The invention also features isolated nucleic acid molecules and/or genes, e.g., bacterial nucleic acid molecules and/or genes, in particular, isolated bacterial coaX nucleic acid molecules and/or genes. Also featured are vectors that contain isolated coaX nucleic acid molecules and/or genes as well as mutant coaX nucleic acid molecules and/or genes. Also featured are recombinant microorganisms (e.g., microorganisms belonging to the genus *Escherichia* or *Bacillus*, for example, *E. coli* or *B. subtilis*) containing isolated coaX nucleic acid molecules and/or genes or mutant coaX nucleic acid molecules and/or genes of the present invention. In particular, the invention features recombinant microorganisms that produce the CoaX proteins of the present invention, e.g., pantohthenate kinase proteins encodes by the coaX nucleic acid molecules and/or genes of the present invention.

Also featured are methods for identifying CoaX modulators utilizing, for example, isolated CoaX proteins of the present invention or recombinant microorganisms expressing the CoaX proteins of the present invention.

Other features and advantages of the invention will be apparent from the following detailed description and claims.

BRIEF DESCRIPTION OF THE DRAWINGS

FIG. 6A-D depicts a multiple sequence alignment (MSA) of the amino acid sequences encoded by fourteen known or predicted microbial coaX genes. SEQ ID NOs:2-15 correspond to the amino acid sequences of *Bacillus subtilis* (Swiss Prot™ Accession No. P37564), *Clostridium acetobulyticum* (WIT™ Accession No. RCA03301, Argonne National Laboratories), *Streptomyces coelicolor* (PIR™ Accession No. T36391), *Mycobacterium tuberculosis* (SwissProt™ Accession No. 006282), *Rhodobacter capsulatus* (WIT™ Accession No. RRC02473), *Desulfovibrio vulgaris* (DBJ™ Accession No. BAA21476.1), *Deinococcus radiodurans* (SwissProt™ Accession No. Q9RX54), *Thermotoga maritima* (GenBank™ Accession No. AAD35964.1), *Treponema pallidum* (SwissProt™ Accession No. 083446), *Borrelia burgdorferi* (SwissProt™ Accession No. 051477), *Aquifex aeolicus* (SwissProt™ Accession No. 067753), *Synechocystis* sp. (SwissProt™ Accession No. P74045), *Helicobacter pylori* (SwissProt™ Accession No. 025533), and *Bordetella pertussis* (SwissProt™ Accession No. Q45338), respectively. The alignment was generated using ClustalW MSA software at the GenomeNet CLUSTALW Server at the Institute for Chemical Research, Kyoto University. The following parameters were used: Pairwise Alignment, K-tuple (word) size=1, Window size=5, Gap Penalty=3, Number of Top Diagonals=5, Scoring Method=Percent; Multiple Alignment, Gap Open Penalty=10, Gap Extension Penalty=0.0, Weight Transition=No, Hydrophilic residues=Gly, Pro, Ser, Asn, Asp, Gln, Glu, Arg and Lys, Hydrophobic Gaps=Yes; and Scoring Matrix=BLOSUM.

DETAILED DESCRIPTION OF THE INVENTION

Figure 1:
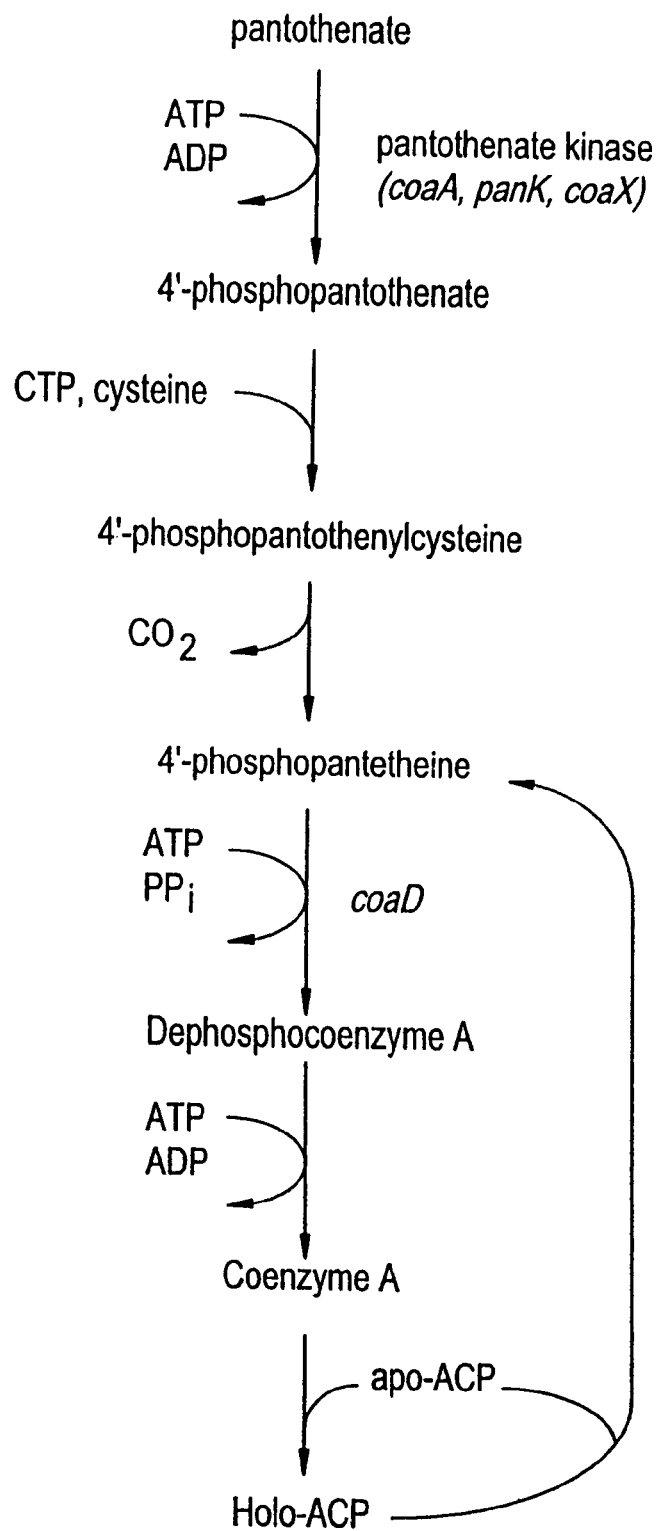
FIG. 1 is a schematic representation of the Coenzyme A biosynthetic pathway in *E. coli*.

The present invention is based at least in part, on the identification of a novel target for use in screening assays designed to identify antimicrobial agents. In particular, the present invention is based on the identification and characterization of a previously unidentified microbial pantothenate kinase. This pantothenate kinase, encoded by a gene, termed coaX herein, is structurally unrelated to the previously characterized *E. coli* pantothenate gene, coaA, however, both genes encode functional pantothenate kinase enzymes, pantothenate kinase being essential for the synthesis of Coenzyme A (CoA). CoA is an essential coenzyme in all cells, participating in over 100 different intermediary reactions in cellular metabolism including, but not limited to, the tricarboxylic acid (TCA) cycle, fatty acid metabolism, vitamin biosynthesis and numerous other reactions of intermediary metabolism. Accordingly, pantothenate kinase production is essential for microbial growth. Coenzyme A (CoA) is synthesized in both eukaryotes and prokaryotes from pantothenate, also known as pantothenic acid or vitamin B5. The initial (and possibly rate-controlling) step in the conversion of pantothenate to Coenzyme A (CoA) is phosphorylation of pantothenate by pantothenate kinase. A schematic representation of the pathway leading to CoAA biosynthesis in *E. coli*, i.e., the *E. coli* CoA biosynthetic pathway is set forth as FIG. 1. The term "CoA biosynthetic pathway", as used herein, includes the biosynthetic pathway involving CoA biosynthetic enzymes (e.g., polypeptides encoded by biosynthetic enzyme-encoding genes), compounds (e.g., precursors, substrates, intermediates or products), cofactors and the like utilized in the formation or synthesis of CoA from pantothenate. The CoA biosynthetic pathway depicted is also presumed to be that utilized by other microorganisms. The term "CoA biosynthetic pathway" includes the biosynthetic pathway leading to the synthesis of CoA in microorganisms (e.g., in vivo) as well as the biosynthetic pathway leading to the synthesis of CoA in vitro.

The term "Coenzyme A or CoA biosynthetic enzyme" includes any enzyme utilized in the formation of a compound (e.g., intermediate or product) of the CoA biosynthetic pathway, for example, the coaA, panK or coaX gene product which catalyzes the phosphorylation of pantothenate to form 4'-phosphopantothenate, or the coaD gene product which catalyzes the conversion of 4'-phosphopantetheine to dephosphocoenzyme A.

The coaX gene was first identified in *B. subtilis*, a microorganism in which it is one of two pantothenate kinase-encoding genes. Initially, the present inventors identified and cloned the *B. subtilis* coaA gene (previously termed yqjs) that encodes a pantothenate kinase homologous to the CoaA enzyme previously characterized in *E. coli*. A second gene (previously termed yacB) has also been identified and cloned by the present inventors that is not homologous to any previously described pantothenate kinase. This latter pantothenate kinase-encoding gene has been renamed coaX. The coaX gene could be deleted from *B. subtilis* strains with an intact coaA gene, but it could not be deleted from a strain containing a deletion in the coaA gene, indicating that the coaX gene is not essential in *B. subtilis* strains with a wild-type coaA gene.

Homologs of the coaX gene can be found in a number of bacterial species, including but not limited to *Aquifex aeolicus, Bacillus anthracis, Bacillus halodurans, Bacillus stearothermophilus, Caulobacter crescentus, Chlorobium tepidum, Clostridium acetobutylicum, Dehalococcoides ethenogenes, Deinococcus radiodurans, Desulfovibrio vulgaris, Geobacter sulfurreducens, Pseudomonas putida, Rhodobacter capsulatus, Thiobacillus ferrooxidans, Streptomyces coelicolor, Synechocystis* sp., *Thermotoga maritima, Bordetella pertussis, Borrelia burgdorferi, Campylobacter jejuni, Clostridium difficile, Helicobacter pylori, Neisseria meningitidis, Neisseria gonorrhoeae, Porphyromonas gingivalis, Pseudomonas aeruginosa, Legionella pneumophila, Treponema pallidum, Xylella fastidiosa* and *Mycobacterium tuberculosis*. More importantly, however, this novel pantothenate kinase gene has been found to be the sole essential pantothenate kinase in troublesome pathogens including, but not limited to, *Bordetella pertussis, Borrelia burgdorferi, Campylobacter jejuni, Helicobacter pylori, Neisseria meningitidis, Pseudomonas aeruginosa, Treponema pallidum* and *Xylella fastidiosa*. Accordingly, the coaX gene represents an attractive target for screening for new antibacterial compounds to combat these pathogenic microorganisms, particularly microorganisms in which coaX is the sole pantothenate kinase-encoding gene.

Accordingly, in one aspect the present invention features assays for the identification an antibiotic that involve contacting a composition comprising a CoaX protein with a test compound; and determining the ability of the test compound to inhibit the activity of the CoaX protein; wherein the compound is identified as an antibiotic based on the ability of the compound to inhibit the activity of the CoaX protein. In another aspect, the invention features an assay for the identification a potential antibiotic that involves contacting an assay composition comprising CoaX with a test compound; and determining the ability of the test compound to bind to the CoaX; wherein the compound is identified as a potential antibiotic based on the ability of the compound to bind to the CoaX. In a preferred assay format, the composition is also contacted with pantothenate or a pantothenate analog and activity determined.

In another aspect, the invention features methods for identifying pantothenate kinase modulators that involve contacting a recombinant cell expressing a single pantothenate kinase encoded by a coaX gene with a test compound and determining the ability of the test compound to modulate pantothenate kinase activity in said cell. In another aspect, the invention features methods for identifying pantothenate kinase modulators that involve contacting a recombinant cell expressing a first and second pantothenate kinase, with a test compound and determining the ability of the test compound to modulate pantothenate kinase activity in said cell, wherein the first or second pantothenate kinase has reduced activity. Preferred recombinant microorganisms are of the genus Bacillus or Escherichia (e.g., Bacillus subtilis or Escherchia coli).

Also featured are isolated nucleic acid molecules that include a coaX gene of the present invention, isolated proteins encoded by the coaX genes of the present invention and biologically active portions thereof. In one embodiment, the invention features a coaX gene derived from a microorganism selected from the group consisting of Aquifex aeolicus, Bacillus anthracis, Bacillus halodurans, Bacillus stearothermophilus, Bacillus subtilis, Caulobacter crescentus, Chlorobium tepidum, Clostridium acetobutylicum, Dehalococcoides ethenogenes, Deinococcus radiodurans, Desulfovibrio vulgaris, Geobacter sulfurreducens, Pseudomonas putida, Rhodobacter capsulatus, Thiobacillus ferrooxidans, Streptomyces coelicolor, Synechocystis sp., Thermotoga maritima, Bordetella pertussis, Borrelia burgdorferi, Campylobacter jejuni, Clostridium difficile, Helicobacter pylori, Neisseria meningitidis, Neisseria gonorrhoeae, Porphyromonas gingivalis, Pseudomonas aeruginosa, Legionella pneumophila, Treponema pallidum, Xylella fastidiosa and Mycobacterium tuberculosis, or a protein encoded by said coaX gene.

In another embodiment, the invention features isolated nucleic acid molecules that include a coaX gene derived from a pathogenic bacterium selected from the group consisting of Bacillus anthracis, Bordetella pertussis, Borrelia burgdorferi, Campylobacter jejuni, Clostridium difficile, Helicobacter pylori, Neisseria meningitidis, Neisseria gonorrhoeae, Pseudomonas aeruginosa, Porphyromonas gingivalis, Legionella pneumophila, Treponema pallidum and Xylella fastidiosa, or a protein encoded by said coaX gene. In a preferred embodiment, the invention features isolated nucleic acid molecules that include a coaX gene derived from a pathogenic bacterium selected from the group consisting of Bordetella pertussis, Borrelia burgdorferi, Campylobacter jejuni, Helicobacter pylori, Neisseria meningitidis, Pseudomonas aeruginosa, Treponema pallidum and Xylella fastidiosa, or a protein encoded by said coaX gene.

Also featured are recombinant vectors that include the isolated coaX genes of the present invention and recombinant microorganisms that include said vectors.

I. General Background

A pantothenate kinase activity was first identified in Salmonella typhimurium by screening for temperature-sensitive mutants which synthesized CoA at permissive temperatures but excreted pantothenate at non-permissive temperatures. The mutations were mapped in the Salmonella chromosome and the genetic locus was designated coaA. The gene encodes the enzyme that catalyzes the first step in the biosynthesis of coenzyme A from pantothenate (Dunn and Snell (1979) J. Bacteriol. 140:805-808). Escherichia coli temperature sensitive mutants have also been isolated and characterized (Vallari and Rock (1987) J. Bacteriol. 169:5795-5800). These mutants (named coaA15(Ts)) are defective in the conversion of pantothenate to CoA and further exhibit a temperature-sensitive growth phenotype, indicating that pantothenate kinase activity is essential for growth. Moreover, it was noted that CoA inhibited pantothenate kinase activity to the same degree in the mutant as compared to the wild-type enzyme.

Feedback resistant E. coli mutants (named coaA16(Fr)) have also been isolated that possess a pantothenate kinase activity that is refractory to feedback inhibition by CoA (Vallari and Jackowski (1988) J. Bacteriol. 170:3961-3966). The mutation responsible for the reversion is, suprisingly, not genetically linked to the coaA gene by transduction. Additional data described therein support the view that the total cellular CoA content is controlled by both modulation of biosynthesis at the pantothenate kinase step and possibly by degradation of CoA to 4'-phosphopantetheine.

The wild-type E. coli coaA gene was cloned by functional complementation of E. coli temperature-sensitive mutants. The sequence of the wild-type gene was determined (Song and Jackowski (1992) J. Bacteriol. 174:6411-6417 and Flamm et al. (1988) Gene (Amst.) 74:555-558). Strains containing multiple copies of the coaA gene possessed 76-fold higher specific activity of pantothenate kinase, however, there was only a 2.7-fold increase in the steady state level of CoA (Song and Jackowski, supra). It has further been reported that the prokaryotic enzyme (encoded by coaA in E. coli and a variety of other microorganisms) is feedback inhibited by CoA both in vivo and in vitro with CoA being about five times more potent than acetyl-CoA in inhibiting the enzyme (Song and Jackowski, supra and Vallari et al., supra). These data further support the view that feedback inhibition of pantothenate kinase activity is a critical factor controlling intracellular CoA concentration. The E. coli CoaA protein has been crystalized and the structure solved (Yun et al. (2000) J. Biol. Chem. 275(36):28093-28099).

Using standard search and alignment tools, coaA homologues have been identified in Hemophilus influenzae, Mycobacterium tuberculosis, Vibrio cholerae, Streptococcus pyogenes and Bacillus subtilis. By contrast, proteins with significant similarity could not be identified in eukaryotic cells including Saccharomyces cerevisiae or in mammalian expressed sequence tag (EST) databases. Using a genetic selection strategy, a cDNA encoding pantothenate kinase activity has recently been identified from Aspergillus nidulans (Calder et al. (1999) J. Biol. Chem. 274:2014-2020). The eukaryotic pantothenate kinase gene (panK) has distinct primary structure and unique regulatory properties that clearly distinguish it from its prokaryotic counterpart. A mammalian pantothenate kinase gene (mpanK1α) has also been isolated which encodes a protein having homology to the A. nidulans PanK protein and to the predicted gene product of GenBank™ Accession Number 927798 identified in the S. cerevisiae genome (Rock et al. (2000) J. Biol. Chem. 275:1377-1383).

II. CoaX Nucleic Acid Molecules

The present invention relates, at least in part, to the identification of a novel microbial pantothenate kinase encoding gene, coaX, that is structurally distinct from a previously identified microbial pantothenate kinase encoding gene, coaA. Accordingly, one aspect of the present invention features isolated coaX nucleic acid molecules and/or genes useful, for example, for encoding pantothenate kinase enzymes for use in screening assays.

The term "nucleic acid molecule" includes DNA molecules (e.g., linear, circular, cDNA or chromosomal DNA)

and RNA molecules (e.g., tRNA, rRNA, mRNA) and analogs of the DNA or RNA generated using nucleotide analogs. The nucleic acid molecule can be single-stranded or double-stranded, but preferably is double-stranded DNA. The term "isolated" nucleic acid molecule includes a nucleic acid molecule that is free of sequences that naturally flank the nucleic acid molecule (i.e., sequences located at the 5' and 3' ends of the nucleic acid molecule) in the chromosomal DNA of the organism from which the nucleic acid is derived. In various embodiments, an isolated nucleic acid molecule can contain less than about 10 kb, 5 kb, 4 kb, 3 kb, 2 kb, 1 kb, 0.5 kb, 0.1 kb, 50 bp, 25 bp or 10 bp of nucleotide sequences which naturally flank the nucleic acid molecule in chromosomal DNA of the microorganism from which the nucleic acid molecule is derived. Moreover, an "isolated" nucleic acid molecule, such as a cDNA molecule, can be substantially free of other cellular materials when produced by recombinant techniques, or substantially free of chemical precursors or other chemicals when chemically synthesized.

The term "gene", as used herein, includes a nucleic acid molecule (e.g., a DNA molecule or segment thereof), for example, a protein or RNA-encoding nucleic acid molecule, that in an organism, is separated from another gene or other genes, by intergenic DNA (i.e., intervening or spacer DNA which naturally flanks the gene and/or separates genes in the chromosomal DNA of the organism). A gene may direct synthesis of an enzyme or other protein molecule (e.g., may comprise coding sequences, for example, a contiguous open reading frame (ORF) which encodes a protein) or may itself be functional in the organism. A gene in an organism, may be clustered in an operon, as defined herein, said operon being separated from other genes and/or operons by the intergenic DNA. Individual genes contained within an operon may overlap without intergenic DNA between said individual genes. An "isolated gene", as used herein, includes a gene which is essentially free of sequences which naturally flank the gene in the chromosomal DNA of the organism from which the gene is derived (i.e., is free of adjacent coding sequences which encode a second or distinct protein or RNA molecule, adjacent structural sequences or the like) and optionally includes 5' and 3' regulatory sequences, for example promoter sequences and/or terminator sequences. In one embodiment, an isolated gene includes predominantly coding sequences for a protein (e.g., sequences which encode *Bacillus* proteins). In another embodiment, an isolated gene includes coding sequences for a protein (e.g., for a *Bacillus* protein) and adjacent 5' and/or 3' regulatory sequences from the chromosomal DNA of the organism from which the gene is derived (e.g., adjacent 5' and/or 3' *Bacillus* regulatory sequences). Preferably, an isolated gene contains less than about 10 kb, 5 kb, 2 kb, 1 kb, 0.5 kb, 0.2 kb, 0.1 kb, 50 bp, 25 bp or 10 bp of nucleotide sequences which naturally flank the gene in the chromosomal DNA of the organism from which the gene is derived.

In one embodiment, an isolated nucleic acid molecule is or includes a coaX gene. In another embodiment, an isolated nucleic acid molecule is or includes a portion or fragment of a coaX gene. In one embodiment, an isolated coaX nucleic acid molecule is derived from a microorganism selected form the group consisting of *Aquifex aeolicus, Bacillus anthracis, Bacillus halodurans, Bacillus stearothermophilus, Bacillus subtilis, Caulobacter crescentus, Chlorobium tepidum, Clostridium acetobutylicum, Dehalococcoides ethenogenes, Deinococcus radiodurans, Desulfovibrio vulgaris, Geobacter sulfurreducens, Pseudomonas putida, Rhodobacter capsulatus, Thiobacillus ferrooxidans, Streptomyces coelicolor, Synechocystis sp., Thermotoga maritima, Bordetella pertussis, Borrelia burgdorferi, Campylobacter jejuni, Clostridium difficile, Helicobacter pylori, Neisseria meningitidis, Neisseria gonorrhoeae, Porphyromonas gingivalis, Pseudomonas aeruginosa, Pseudomonas syringae pv tomato, Treponema pallidum, Xylella fastidiosa, Legionella pneumophila* and *Mycobacterium tuberculosis*. In another embodiment, an isolated coaX nucleic acid molecule is derived from a microorganism selected from the group consisting of *Bacillus anthracis, Bordetella pertussis, Borrelia burgdorferi, Campylobacter jejuni, Clostridium difficile, Helicobacter pylori, Neisseria meningitidis, Neisseria gonorrhoeae, Porphyromonas gingivalis, Pseudomonas aeruginosa, Treponema pallidum, Xylella fastidiosa* and *Legionella pneumophila*. In another embodiment, an isolated coaX nucleic acid molecule is derived from a microorganism selected from the group consisting of *Bordetella pertussis, Borrelia burgdorferi, Campylobacter jejuni, Clostridium difficile, Helicobacter pylori, Neisseria meningitidis, Pseudomonas aeruginosa, Treponema pallidum* and *Xylella fastidiosa*. In another embodiment, an isolated coaX nucleic acid molecule or gene comprises a nucleotide sequence set forth as any one of SEQ ID NOs:SEQ ID NO:32, SEQ ID NO:69, SEQ ID NO:46, SEQ ID NO:48, SEQ ID NO:50, SEQ ID NO:1, SEQ ID NO:38, SEQ ID NO:31, SEQ ID NO:36, SEQ ID NO:52, SEQ ID NO:54, SEQ ID NO:23, SEQ ID NO:56, SEQ ID NO:58, SEQ ID NO:28, SEQ ID NO:60, SEQ ID NO:27, SEQ ID NO:34 or SEQ ID NO:68, SEQ ID NO:25, SEQ ID NO:40, SEQ ID NO:44, SEQ ID NO:42, SEQ ID NO:35 or SEQ ID NO:37, SEQ ID NO:62, SEQ ID NO:26, SEQ ID NO:24, SEQ ID NO:33, SEQ ID NO:29, SEQ ID NO:64, SEQ ID NO:30 and SEQ ID NO:66. In another embodiment, an isolated nucleic acid molecule of the present invention comprises a nucleotide sequence which is at least about 50-55%, preferably at least about 60-65%, more preferably at least about 70-75%, more preferably at least about 80-85%, and even more preferably at least about 90-95% or more identical to a nucleotide sequence set forth as any one of SEQ ID NOs:SEQ ID NO:32, SEQ ID NO:69, SEQ ID NO:46, SEQ ID NO:48, SEQ ID NO:50, SEQ ID NO:1, SEQ ID NO:38, SEQ ID NO:31, SEQ ID NO:36, SEQ ID NO:52, SEQ ID NO:54, SEQ ID NO:23, SEQ ID NO:56, SEQ ID NO:58, SEQ ID NO:28, SEQ ID NO:60, SEQ ID NO:27, SEQ ID NO:34 or SEQ ID NO:68, SEQ ID NO:25, SEQ ID NO:40, SEQ ID NO:44, SEQ ID NO:42, SEQ ID NO:35 or SEQ ID NO:37, SEQ ID NO:62, SEQ ID NO:26, SEQ ID NO:24, SEQ ID NO:33, SEQ ID NO:29, SEQ ID NO:64, SEQ ID NO:30 and SEQ ID NO:66.

In yet another embodiment, an isolated coaX nucleic acid molecule or gene comprises a nucleotide sequence that encodes a protein having an amino acid sequence as set forth in any one of SEQ ID NOs:SEQ ID NO:12, SEQ ID NO:70, SEQ ID NO:45, SEQ ID NO:47, SEQ ID NO:49, SEQ ID NO:2, SEQ ID NO:51, SEQ ID NO:53, SEQ ID NO:3, SEQ ID NO:57, SEQ ID NO:8, SEQ ID NO:59, SEQ ID NO:7, SEQ ID NO:61, SEQ ID NO:6, SEQ ID NO:63, SEQ ID NO:4, SEQ ID NO:13, SEQ ID NO:9, SEQ ID NO:15, SEQ ID NO:11, SEQ ID NO:21, SEQ ID NO:55, SEQ ID NO:14 or SEQ ID NO:67, SEQ ID NO:43 or SEQ ID NO:22, SEQ ID NO:39, SEQ ID NO:41, SEQ ID NO:20, SEQ ID NO:10, SEQ ID NO:65 and SEQ ID NO:5. In yet another embodiment, an isolated coaX nucleic acid molecule or gene encodes a homologue of the CoaX proteins having the amino acid sequences of SEQ ID NOs:SEQ ID NO:12, SEQ ID NO:70, SEQ ID NO:45, SEQ ID NO:47, SEQ ID NO:49, SEQ ID NO:2, SEQ ID NO:51, SEQ ID NO:53, SEQ ID NO:3, SEQ ID NO:57, SEQ ID NO:8, SEQ ID NO:59, SEQ ID NO:7, SEQ ID NO:61, SEQ ID NO:6, SEQ ID NO:63, SEQ ID NO:4, SEQ ID NO:13, SEQ ID NO:9, SEQ ID NO:15, SEQ ID NO:11, SEQ ID NO:21, SEQ ID NO:55, SEQ ID NO:14 or SEQ ID NO:67, SEQ ID NO:43 or SEQ ID NO:22, SEQ ID NO:39, SEQ ID NO:41, SEQ ID NO:20, SEQ ID NO:10, SEQ ID NO:65 and SEQ ID NO:5. As used herein, the term "homologue" includes a protein or polypeptide sharing at least about 30-35%, preferably at least about 35-40%, more preferably at least about 40-50%, and even more preferably at least about 60%, 70%, 80%, 90% or more identity with the amino acid sequence of a wild-type protein or polypeptide described herein and having a substantially equivalent functional or biological activity as said wild-type protein or polypeptide. For example, a CoaX homologue shares at least about 30-35%, preferably at least about 35-40%, more preferably at least about 40-50%, and even more preferably at least about 60%, 70%, 80%, 90% or more identity with any one of the proteins having the amino acid sequences set forth as SEQ ID NOs:SEQ ID NO:12, SEQ ID NO:70, SEQ ID NO:45, SEQ ID NO:47, SEQ ID NO:49, SEQ ID NO:2, SEQ ID NO:51, SEQ ID NO:53, SEQ ID NO:3, SEQ ID NO:57, SEQ ID NO:8, SEQ ID NO:59, SEQ ID NO:7, SEQ ID NO:61, SEQ ID NO:6, SEQ ID NO:63, SEQ ID NO:4, SEQ ID NO:13, SEQ ID NO:9, SEQ ID NO:15, SEQ ID NO:11, SEQ ID NO:21, SEQ ID NO:55, SEQ ID NO:14 or SEQ ID NO:67, SEQ ID NO:43 or SEQ ID NO:22, SEQ ID NO:39, SEQ ID NO:41, SEQ ID NO:20, SEQ ID NO:10, SEQ ID NO:65 and SEQ ID NO:5 and has a substantially equivalent functional or biological activity (i.e., is a functional equivalent) of the proteins having the amino acid sequences set forth as SEQ ID NOs:SEQ ID NO:12, SEQ ID NO:70, SEQ ID NO:45, SEQ ID NO:47, SEQ ID NO:49, SEQ ID NO:2, SEQ ID NO:51, SEQ ID NO:53, SEQ ID NO:3, SEQ ID NO:57, SEQ ID NO:8, SEQ ID NO:59, SEQ ID NO:7, SEQ ID NO:61, SEQ ID NO:6, SEQ ID NO:63, SEQ ID NO:4, SEQ ID NO:13, SEQ ID NO:9, SEQ ID NO:15, SEQ ID NO:11, SEQ ID NO:21, SEQ ID NO:55, SEQ ID NO:14 or SEQ ID NO:67, SEQ ID NO:43 or SEQ ID NO:22, SEQ ID NO:39, SEQ ID NO:41, SEQ ID NO:20, SEQ ID NO:10, SEQ ID NO:65 and SEQ ID NO:5 (e.g., has a substantially equivalent CoaX activity). In a preferred embodiment, an isolated coaX nucleic acid molecule or gene comprises a nucleotide sequence that encodes a polypeptide as set forth in any one of SEQ ID NOs:SEQ ID NO:12, SEQ ID NO:70, SEQ ID NO:45, SEQ ID NO:47, SEQ ID NO:49, SEQ ID NO:2, SEQ ID NO:51, SEQ ID NO:53, SEQ ID NO:3, SEQ ID NO:57, SEQ ID NO:8, SEQ ID NO:59, SEQ ID NO:7, SEQ ID NO:61, SEQ ID NO:6, SEQ ID NO:63, SEQ ID NO:4, SEQ ID NO:13, SEQ ID NO:9, SEQ ID NO:15, SEQ ID NO:11, SEQ ID NO:21, SEQ ID NO:55, SEQ ID NO:14 or SEQ ID NO:67, SEQ ID NO:43 or SEQ ID NO:22, SEQ ID NO:39, SEQ ID NO:41, SEQ ID NO:20, SEQ ID NO:10, SEQ ID NO:65 and SEQ ID NO:5.

In another embodiment, an isolated coaX nucleic acid molecule hybridizes to all or a portion of a nucleic acid molecule having the nucleotide sequence set forth in any one of SEQ ID NOs:SEQ ID NO:32, SEQ ID NO:69, SEQ ID NO:46, SEQ ID NO:48, SEQ ID NO:50, SEQ ID NO:1, SEQ ID NO:38, SEQ ID NO:31, SEQ ID NO:36, SEQ ID NO:52, SEQ ID NO:54, SEQ ID NO:23, SEQ ID NO:56, SEQ ID NO:58, SEQ ID NO:28, SEQ ID NO:60, SEQ ID NO:27, SEQ ID NO:34 or SEQ ID NO:68, SEQ ID NO:25, SEQ ID NO:40, SEQ ID NO:44, SEQ ID NO:42, SEQ ID NO:35 or SEQ ID NO:37, SEQ ID NO:62, SEQ ID NO:26, SEQ ID NO:24, SEQ ID NO:33, SEQ ID NO:29, SEQ ID NO:64, SEQ ID NO:30 and SEQ ID NO:66 or hybridizes to all or a portion of a nucleic acid molecule having a nucleotide sequence that encodes a polypeptide having the amino acid sequence of any of SEQ ID NOs:SEQ ID NO:12, SEQ ID NO:70, SEQ ID NO:45, SEQ ID NO:47, SEQ ID NO:49, SEQ ID NO:2, SEQ ID NO:51, SEQ ID NO:53, SEQ ID NO:3, SEQ ID NO:57, SEQ ID NO:8, SEQ ID NO:59, SEQ ID NO:7, SEQ ID NO:61, SEQ ID NO:6, SEQ ID NO:63, SEQ ID NO:4, SEQ ID NO:13, SEQ ID NO:9, SEQ ID NO:15, SEQ ID NO:11, SEQ ID NO:21, SEQ ID NO:55, SEQ ID NO:14 or SEQ ID NO:67, SEQ ID NO:43 or SEQ ID NO:22, SEQ ID NO:39, SEQ ID NO:41, SEQ ID NO:20, SEQ ID NO:10, SEQ ID NO:65 and SEQ ID NO:5. Such hybridization conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15 M NaCl, 10 mM NaH$_2$PO$_4$, and 1.25 mM EDTA, pH 7.4) can be substituted for SSC (1×SSC is 0.15 M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m(° C.)=2(\# of A+T bases)+4(\# of G+C bases)$. For hybrids between 18 and 49 base pairs in length, $T_m(° C.)=81.5+16.6(\log_{10}[Na^+])+0.41(\% G+C)-(600/N)$, where N is the number of bases in the hybrid, and [Na$^+$] is the concentration of sodium ions in the hybridization buffer ([Na$^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M NaH$_2$PO$_4$, 7% SDS at about 65° C., followed by one or more washes at 0.02M NaH$_2$PO$_4$, 1% SDS at 65° C., see e.g., Church and Gilbert (1984) *Proc. Natl. Acad. Sci. USA* 81:1991-1995, (or, alternatively, 0.2×SSC, 1% SDS). In another preferred embodiment, an isolated nucleic acid molecule comprises a nucleotide sequence that is complementary to a coaX nucleotide sequence as set forth herein (e.g., is the full complement of the nucleotide sequence set forth as SEQ ID NO:19). Preferably, an isolated nucleic acid molecule of the invention that hybridizes under stringent conditions to the sequence of SEQ ID NO:SEQ ID NO:32, SEQ ID NO:69, SEQ ID NO:46, SEQ ID NO:48, SEQ ID NO:50, SEQ ID NO:1, SEQ ID NO:38, SEQ ID NO:31, SEQ ID NO:36, SEQ ID NO:52, SEQ ID NO:54, SEQ ID NO:23, SEQ ID NO:56, SEQ ID NO:58, SEQ ID NO:28, SEQ ID NO:60, SEQ ID NO:27, SEQ ID NO:34 or SEQ ID NO:68, SEQ ID NO:25, SEQ ID NO:40, SEQ ID NO:44, SEQ ID NO:42, SEQ ID NO:35 or SEQ ID NO:37, SEQ ID NO:62, SEQ ID NO:26, SEQ ID NO:24, SEQ ID NO:33, SEQ ID NO:29, SEQ ID NO:64, SEQ ID NO:30 and SEQ ID NO:66, or to a complement thereof, corresponds to a naturally-occurring nucleic acid molecule. As used herein, a "naturally-occurring" nucleic acid molecule refers to an RNA or DNA molecule having a nucleotide sequence that occurs in nature.

A nucleic acid molecule of the present invention (e.g., a coaX nucleic acid molecule or gene), can be isolated using standard molecular biology techniques and the sequence information provided herein. For example, nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989) or can be isolated by the polymerase chain reaction using synthetic oligonucleotide primers designed based upon the coaX nucleotide sequences set forth herein, or flanking sequences thereof. A nucleic acid of the invention (e.g., a coaX nucleic acid molecule or gene), can be amplified using cDNA, mRNA or alternatively, chromosomal DNA, as a template and appropriate oligonucleotide primers according to standard PCR amplification techniques. Assays for identifying coaX gene of the present invention or homologues thereof can be accomplished, for example, by expressing the coaX gene in a microorganism, for example, a microorganism which expresses pantothenate kinase in a temperature-sensitive manner, and assaying the gene for the ability to complement a temperature sensitive (Ts) mutant for pantothenate kinase activity. A coaX gene that encodes a functional pantothenate kinase is one that complements the Ts mutant.

Yet another embodiment of the present invention features mutant coaX and coaA nucleic acid molecules or genes. The phrase "mutant nucleic acid molecule" or "mutant gene" as used herein, includes a nucleic acid molecule or gene having a nucleotide sequence which includes at least one alteration (e.g., substitution, insertion, deletion) such that the polypeptide or protein that may be encoded by said mutant exhibits an activity that differs from the polypeptide or protein encoded by the wild-type nucleic acid molecule or gene. Preferably, a mutant nucleic acid molecule or mutant gene (e.g., a mutant coaA or coaX gene) encodes a polypeptide or protein having a reduced activity (e.g., having a reduced pantothenate kinase activity) as compared to the polypeptide or protein encoded by the wild-type nucleic acid molecule or gene, for example, when assayed under similar conditions (e.g., assayed in microorganisms cultured at the same temperature). A mutant gene also can encode no polypeptide or have a reduced level of production of the wild-type polypeptide.

As used herein, a "reduced activity" or "reduced enzymatic activity" is one that is at least 5% less than that of the polypeptide or protein encoded by the wild-type nucleic acid molecule or gene, preferably at least 5-10% less, more preferably at least 10-25% less and even more preferably at least 25-50%, 50-75% or 75-100% less than that of the polypeptide or protein encoded by the wild-type nucleic acid molecule or gene. Ranges intermediate to the above-recited values, e.g., 75-85%, 85-90%, 90-95%, are also intended to be encompassed by the present invention. As used herein, a "reduced activity" or "reduced enzymatic activity" also includes an activity that has been deleted or "knocked out" (e.g., approximately 100% less activity than that of the polypeptide or protein encoded by the wild-type nucleic acid molecule or gene). Activity can be determined according to any well accepted assay for measuring activity of a particular protein of interest. Activity can be measured or assayed directly, for example, measuring an activity of a protein isolated or purified from a cell. Alternatively, an activity can be measured or assayed within a cell or in an extracellular medium or in a crude extract of cells.

It will be appreciated by the skilled artisan that even a single substitution in a nucleic acid or gene sequence (e.g., a base substitution that encodes an amino acid change in the corresponding amino acid sequence) can dramatically affect the activity of an encoded polypeptide or protein as compared to the corresponding wild-type polypeptide or protein. A mutant nucleic acid or mutant gene (e.g., encoding a mutant polypeptide or protein), as defined herein, is readily distinguishable from a nucleic acid or gene encoding a protein homologue, as described above, in that a mutant nucleic acid or mutant gene encodes a protein or polypeptide having an altered activity, optionally observable as a different or distinct phenotype in a microorganism expressing said mutant gene or nucleic acid or producing said mutant protein or polypeptide (i.e., a mutant microorganism) as compared to a corresponding microorganism expressing the wild-type gene or nucleic acid or producing said mutant protein or polypeptide. By contrast, a protein homologue has an identical or substantially similar activity, optionally phenotypically indiscernable when produced in a microorganism, as compared to a corresponding microorganism expressing the wild-type gene or nucleic acid. Accordingly it is not, for example, the degree of sequence identity between nucleic acid molecules, genes, protein or polypeptides that serves to distinguish between homologues and mutants, rather it is the activity of the encoded protein or polypeptide that distinguishes between homologues and mutants: homologues having, for example, low (e.g., 30-50% sequence identity) sequence identity yet having substantially equivalent functional activities, and mutants, for example sharing 99% sequence identity yet having dramatically different or altered functional activities. Exemplary homologues are set forth as SEQ ID NOs:SEQ ID NO:12, SEQ ID NO:70, SEQ ID NO:45, SEQ ID NO:47, SEQ ID NO:49, SEQ ID NO:51, SEQ ID NO:53, SEQ ID NO:3, SEQ ID NO:57, SEQ ID NO:8, SEQ ID NO:59, SEQ ID NO:7, SEQ ID NO:61, SEQ ID NO:6, SEQ ID NO:63, SEQ ID NO:4, SEQ ID NO:13, SEQ ID NO:9, SEQ ID NO:15, SEQ ID NO:11, SEQ ID NO:21, SEQ ID NO:55, SEQ ID NO:14 or SEQ ID NO:67, SEQ ID NO:43 or SEQ ID NO:22, SEQ ID NO:39, SEQ ID NO:41, SEQ ID NO:20, SEQ ID NO:10, SEQ ID NO:65 and SEQ ID NO:5 (i.e., CoaX homologues). Exemplary mutants are described in Examples III-IV herein.

III. CoaX Proteins

Another aspect of the present invention features isolated proteins (e.g., isolated CoaX proteins encoded, for example, by any one of the coaX genes or nucleic acids described herein). In one embodiment, the isolated proteins are produced by recombinant DNA techniques and can be isolated from microorganisms expressing, for example, any one of the coaX genes or nucleic acids described herein, by an appropriate purification scheme using standard protein purification techniques. In another embodiment, proteins are synthesized chemically using standard peptide synthesis techniques.

An "isolated" or "purified" protein (e.g., an isolated or purified CoaX enzyme) is substantially free of cellular material or other contaminating proteins from the microorganism from which the protein is derived, or substantially free from chemical precursors or other chemicals when chemically synthesized. In one embodiment, an isolated or purified protein has less than about 30% (by dry weight) of contaminating protein or chemicals, more preferably less than about 20% of contaminating protein or chemicals, still more preferably less than about 10% of contaminating protein or chemicals, and most preferably less than about 5% contaminating protein or chemicals.

A "partially purified" protein (e.g., a partially purified CoaX enzyme) is a composition comprising a protein of interest where the composition has been subjected to at least one purification step, separation step, concentration step, or the like, such that the protein of interest is present at a greater concentration or level than prior to the purification step, separation step, concentration step, or the like. In one embodiment, a partially purified protein has between about 50-65% (by dry weight) of contaminating protein or chemicals, preferably between about 40%-50% of contaminating protein or chemicals, more preferably between about 30-40% of contaminating protein or chemicals.

Included within the scope of the present invention are CoaX proteins encoded by naturally-occurring bacterial or microbial genes, for example, by coaX genes derived from a microorganism selected from the group consisting of *Aquifex aeolicus, Bacillus anthracis, Bacillus halodurans, Bacillus stearothermophilus, Bacillus subtilis, Caulobacter crescentus, Chlorobium tepidum, Clostridium acetobutylicum, Dehalococcoides ethenogenes, Deinococcus radiodurans, Desulfovibrio vulgaris, Geobacter sulfurreducens, Pseudomonas putida, Rhodobacter capsulatus, Thiobacillus ferrooxidans, Streptomyces coelicolor, Synechocystis* sp., *Thermotoga maritima, Bordetella pertussis, Borrelia burgdorferi, Campylobacter jejuni, Clostridium difficile, Helicobacter pylori, Neisseria meningitidis, Neisseria gonorrhoeae, Porphyromonas gingivalis, Pseudomonas aeruginosa, Treponema pallidum, Xylella fastidiosa* and *Mycobacterium tuberculosis*. Further included within the scope of the present invention are CoaX proteins that are encoded bacterial or microbial genes which differ from naturally-occurring bacterial or microbial genes described herein, for example, genes which have nucleic acids that are mutated, inserted or deleted, but which encode proteins substantially similar to the naturally-occurring gene products of the present invention. For example, it is well understood that one of skill in the art can mutate (e.g., substitute) nucleic acids which, due to the degeneracy of the genetic code, encode for an identical amino acid as that encoded by the naturally-occurring gene. Moreover, it is well understood that one of skill in the art can mutate (e.g., substitute) nucleic acids which encode for conservative amino acid substitutions. It is further well understood that one of skill in the art can substitute, add or delete amino acids to a certain degree without substantially affecting the function of a gene product as compared with a naturally-occurring gene product, each instance of which is intended to be included within the scope of the present invention.

In one embodiment, an isolated protein of the present invention is encoded by a coaX gene derived from a microorganism selected from the group consisting of *Aquifex aeolicus, Bacillus anthracis, Bacillus halodurans, Bacillus stearothermophilus, Bacillus subtilis, Caulobacter crescentus, Chlorobium tepidum, Clostridium acetobutylicum, Dehalococcoides ethenogenes, Deinococcus radiodurans, Desulfovibrio vulgaris, Geobacter sulfurreducens, Pseudomonas putida, Rhodobacter capsulatus, Thiobacillus ferrooxidans, Streptomyces coelicolor, Synechocystis* sp., *Thermotoga maritima, Bordetella pertussis, Borrelia burgdorferi, Campylobacter jejuni, Clostridium difficile, Helicobacter pylori, Neisseria meningitidis, Neisseria gonorrhoeae, Porphyromonas gingivalis, Pseudomonas aeruginosa, Treponema pallidum, Xylella fastidiosa* and *Mycobacterium tuberculosis*. In another embodiment, an isolated protein of the present invention is encoded by a coaX gene derived from a microorganism selected from the group consisting of *Bacillus anthracis, Bordetella pertussis, Borrelia burgdorferi, Campylobacter jejuni, Clostridium difficile, Helicobacter pylori, Neisseria meningitidis, Neisseria gonorrhoeae, Porphyromonas gingivalis, Pseudomonas aeruginosa, Legionella pneumophila, Treponema pallidum* and *Xylella fastidiosa* (e.g., is encoded by a coaX gene derived from a pathogenic bacteria). In yet another embodiment, an isolated protein of the present invention is encoded by a coaX gene derived from a microorganism selected from the group consisting of *Bordetella pertussis, Borrelia burgdorferi, Campylobacter jejuni, Clostridium difficile, Helicobacter pylori, Neisseria meningitidis, Pseudomonas aeruginosa, Treponema pallidum* and *Xylella fastidiosa* (e.g., is encoded by a coaX gene derived from a pathogenic bacteria which has coaX as it's sole pantothenate kinase encoding enzyme). In a preferred embodiment, an isolated protein of the present invention (e.g., a CoaX) has an amino acid sequence as set forth in any one of SEQ ID NOs:SEQ ID NO:12, SEQ ID NO:70, SEQ ID NO:45, SEQ ID NO:47, SEQ ID NO:49, SEQ ID NO:2, SEQ ID NO:51, SEQ ID NO:53, SEQ ID NO:3, SEQ ID NO:57, SEQ ID NO:8, SEQ ID NO:59, SEQ ID NO:7, SEQ ID NO:61, SEQ ID NO:6, SEQ ID NO:63, SEQ ID NO:4, SEQ ID NO:13, SEQ ID NO:9, SEQ ID NO:15, SEQ ID NO:11, SEQ ID NO:21, SEQ ID NO:55, SEQ ID NO:14 or SEQ ID NO:67, SEQ ID NO:43 or SEQ ID NO:22, SEQ ID NO:39, SEQ ID NO:41, SEQ ID NO:20, SEQ ID NO:10, SEQ ID NO:65 and SEQ ID NO:5. In other embodiments, an isolated protein of the present invention (e.g., a CoaX) is a homologue of the at least one of the proteins set forth as SEQ ID NOs:SEQ ID NO:12, SEQ ID NO:70, SEQ ID NO:45, SEQ ID NO:47, SEQ ID NO:49, SEQ ID NO:2, SEQ ID NO:51, SEQ ID NO:53, SEQ ID NO:3, SEQ ID NO:57, SEQ ID NO:8, SEQ ID NO:59, SEQ ID NO:7, SEQ ID NO:61, SEQ ID NO:6, SEQ ID NO:63, SEQ ID NO:4, SEQ ID NO:13, SEQ ID NO:9, SEQ ID NO:15, SEQ ID NO:11, SEQ ID NO:21, SEQ ID NO:55, SEQ ID NO:14 or SEQ ID NO:67, SEQ ID NO:43 or SEQ ID NO:22, SEQ ID NO:39, SEQ ID NO:41, SEQ ID NO:20, SEQ ID NO:10, SEQ ID NO:65 and SEQ ID NO:5 (e.g., comprises an amino acid sequence at least about 30-40% identical, preferably about 40-50% identical, more preferably about 50-60% identical, and even more preferably about 60-70%, 70-80%, 80-90%, 90-95% or more identical to the amino acid sequence of SEQ ID NOs:SEQ ID NO:12, SEQ ID NO:70, SEQ ID NO:45, SEQ ID NO:47, SEQ ID NO:49, SEQ ID NO:2, SEQ ID NO:51, SEQ ID NO:53, SEQ ID NO:3, SEQ ID NO:57, SEQ ID NO:8, SEQ ID NO:59, SEQ ID NO:7, SEQ ID NO:61, SEQ ID NO:6, SEQ ID NO:63, SEQ ID NO:4, SEQ ID NO:13, SEQ ID NO:9, SEQ ID NO:15, SEQ ID NO:11, SEQ ID NO:21, SEQ ID NO:55, SEQ ID NO:14 or SEQ ID NO:67, SEQ ID NO:43 or SEQ ID NO:22, SEQ ID NO:39, SEQ ID NO:41, SEQ ID NO:20, SEQ ID NO:10, SEQ ID NO:65 and SEQ ID NO:5, and has an activity that is substantially similar to that of the protein encoded by the amino acid sequence of SEQ ID NOs:SEQ ID NO:12, SEQ ID NO:70, SEQ ID NO:45, SEQ ID NO:47, SEQ ID NO:49, SEQ ID NO:2, SEQ ID NO:51, SEQ ID NO:53, SEQ ID NO:3, SEQ ID NO:57, SEQ ID NO:8, SEQ ID NO:59, SEQ ID NO:7, SEQ ID NO:61, SEQ ID NO:6, SEQ ID NO:63, SEQ ID NO:4, SEQ ID NO:13, SEQ ID NO:9, SEQ ID NO:15, SEQ ID NO:11, SEQ ID NO:21, SEQ ID NO:55, SEQ ID NO:14 or SEQ ID NO:67, SEQ ID NO:43 or SEQ ID NO:22, SEQ ID NO:39, SEQ ID NO:41, SEQ ID NO:20, SEQ ID NO:10, SEQ ID NO:65 and SEQ ID NO:5, respectively.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions×100), preferably taking into account the number of gaps and size of said gaps necessary to produce an optimal alignment.

The comparison of sequences and determination of percent homology between two sequences can be accomplished using a mathematical algorithm. A preferred, non-limiting example of a mathematical algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the NBLAST and XBLAST programs (version 2.0) of Altschul et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Research 25(17):3389-3402. When utilizing BLAST and Gapped BLAST programs, the default parameters of the respective programs (e.g., XBLAST and NBLAST) can be used. See, ncbi.nlm.nih.gov. Another preferred, non-limiting example of a mathematical algorithm utilized for the comparison of sequences is the algorithm of Myers and Miller (1988) Comput Appl Biosci. 4:11-17. Such an algorithm is incorporated into the ALIGN program available, for example, at the GENESTREAM network server, IGH Montpellier, FRANCE (vega.igh.cnrs.fr) or at the ISREC server (ch.embnet.org). When utilizing the ALIGN program for comparing amino acid sequences, a PAM120 weight residue table, a gap length penalty of 12, and a gap penalty of 4 can be used.

In another preferred embodiment, the percent homology between two amino acid sequences can be determined using the GAP program in the GCG software package (available at gcg.com), using either a Blossom 62 matrix or a PAM250 matrix, and a gap weight of 12, 10, 8, 6, or 4 and a length weight of 2, 3, or 4. In yet another preferred embodiment, the percent homology between two nucleic acid sequences can be accomplished using the GAP program in the GCG software package (available at gcg.com), using a gap weight of 50 and a length weight of 3.

VI. Recombinant Nucleic Acid Molecules, Vectors and Microorganisms

The present invention further features recombinant nucleic acid molecules (e.g., recombinant DNA molecules) that include nucleic acid molecules and/or genes described herein (e.g., isolated nucleic acid molecules and/or genes), preferably pantothenate kinase-encoding genes (e.g., coaX genes). The present invention further features vectors (e.g., recombinant vectors) that include nucleic acid molecules (e.g., isolated or recombinant nucleic acid molecules and/or genes) described herein. In particular, recombinant vectors are featured that include nucleic acid sequences that encode bacterial gene products as described herein, preferably bacterial nucleic acid sequences that encode bacterial pantothenate kinase proteins.

The term "recombinant nucleic acid molecule" includes a nucleic acid molecule (e.g., a DNA molecule) that has been altered, modified or engineered such that it differs in nucleotide sequence from the native or natural nucleic acid molecule from which the recombinant nucleic acid molecule was derived (e.g., by addition, deletion or substitution of one or more nucleotides). Preferably, a recombinant nucleic acid molecule (e.g., a recombinant DNA molecule) includes an isolated nucleic acid molecule or gene of the present invention (e.g., an isolated coaX gene) operably linked to regulatory sequences.

The term "recombinant vector" includes a vector (e.g., plasmid, phage, phasmid, virus, cosmid or other purified nucleic acid vector) that has been altered, modified or engineered such that it contains greater, fewer or different nucleic acid sequences than those included in the native or natural nucleic acid molecule from which the recombinant vector was derived. Preferably, the recombinant vector includes a coaX gene or recombinant nucleic acid molecule including such coaX gene, operably linked to regulatory sequences, for example, promoter sequences, terminator sequences and/or artificial ribosome binding sites (RBSs), as defined herein.

The phrase "operably linked to regulatory sequence(s)" means that the nucleotide sequence of the nucleic acid molecule or gene of interest is linked to the regulatory sequence(s) in a manner which allows for expression (e.g., enhanced, increased, constitutive, basal, attenuated, decreased or repressed expression) of the nucleotide sequence, preferably expression of a gene product encoded by the nucleotide sequence (e.g., when the recombinant nucleic acid molecule is included in a recombinant vector, as defined herein, and is introduced into a microorganism).

The term "regulatory sequence" includes nucleic acid sequences which affect (e.g., modulate or regulate) expression of other nucleic acid sequences. In one embodiment, a regulatory sequence is included in a recombinant nucleic acid molecule or recombinant vector in a similar or identical position and/or orientation relative to a particular gene of interest as is observed for the regulatory sequence and gene of interest as it appears in nature, e.g., in a native position and/or orientation. For example, a gene of interest can be included in a recombinant nucleic acid molecule or recombinant vector operably linked to a regulatory sequence which accompanies or is adjacent to the gene of interest in the natural organism (e.g., operably linked to "native" regulatory sequences, for example, to the "native" promoter). Alternatively, a gene of interest can be included in a recombinant nucleic acid molecule or recombinant vector operably linked to a regulatory sequence which accompanies or is adjacent to another (e.g., a different) gene in the natural organism. Alternatively, a gene of interest can be included in a recombinant nucleic acid molecule or recombinant vector operably linked to a regulatory sequence from another organism. For example, regulatory sequences from other microbes (e.g., other bacterial regulatory sequences, bacteriophage regulatory sequences and the like) can be operably linked to a particular gene of interest.

In one embodiment, a regulatory sequence is a non-native or non-naturally-occurring sequence (e.g., a sequence which has been modified, mutated, substituted, derivatized, deleted including sequences which are chemically synthesized). Preferred regulatory sequences include promoters, enhancers, termination signals, anti-termination signals and other expression control elements (e.g., sequences to which repressors or inducers bind and/or binding sites for transcriptional and/or translational regulatory proteins, for example, in the transcribed mRNA). Such regulatory sequences are described, for example, in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. Regulatory sequences include those which direct constitutive expression of a nucleotide sequence in a microorganism (e.g., constitutive promoters and strong constitutive promoters), those which direct inducible expression of a nucleotide sequence in a microorganism (e.g., inducible promoters, for example, xylose inducible promoters) and those which attenuate or repress expression of a nucleotide sequence in a microorganism (e.g., attenuation signals or repressor sequences). It is also within the scope of the present invention to regulate expression of a gene of interest by removing or deleting regulatory sequences. For example, sequences involved in the negative regulation of transcription can be removed such that expression of a gene of interest is enhanced.

In one embodiment, a recombinant nucleic acid molecule or recombinant vector of the present invention includes a nucleic acid sequence or gene that encodes at least one bacterial gene product (e.g., a gene product encoded by coaX) operably linked to a promoter or promoter sequence. Preferred promoters of the present invention include *E. coli* promoters or *Bacillus* promoters and/or bacteriophage promoters (e.g., bacteriophage which infect *E. coli* or *Bacillus*). In one embodiment, a promoter is a *Bacillus* promoter, preferably a strong *Bacillus* promoter (e.g., a promoter associated with a biochemical housekeeping gene in *Bacillus* or a promoter associated with a glycolytic pathway gene in *Bacillus*). In another embodiment, a promoter is a bacteriophage promoter. In a preferred embodiment, the promoter is from the bacteriophage SP01. In a particularly preferred embodiment, a promoter is the $P_{26}$ promoter set forth as SEQ ID NO:18 or the $P_{15}$ promoter set forth as SEQ ID NO:19. Additional preferred promoters include tef(the translational elongation factor (TEF) promoter) and pyc (the pyruvate carboxylase (PYC) promoter), which promote high level expression in *Bacillus* (e.g., *Bacillus subtilis*). Additional preferred promoters, for example, for use in Gram positive microorganisms include, but are not limited to, the amyE promoter or phage SP02 promoters. Additional preferred promoters, for example, for use in Gram negative microorganisms include, but are not limited to tac, trp, tet, trp-tet, lpp, lac, lpp-lac, lacIq, T7, T5, T3, gal, trc, ara, SP6, $\lambda$-$P_R$ or $\lambda$-$P_L$.

In another embodiment, a recombinant nucleic acid molecule or recombinant vector of the present invention includes a terminator sequence or terminator sequences (e.g., transcription terminator sequences). The term "terminator sequences" includes regulatory sequences which serve to terminate transcription of a gene. Terminator sequences (or tandem transcription terminators) can further serve to stabilize mRNA (e.g., by adding structure to mRNA), for example, against nucleases.

In yet another embodiment, a recombinant nucleic acid molecule or recombinant vector of the present invention includes sequences which allow for detection of the vector containing said sequences (i.e., detectable and/or selectable markers), for example, sequences that overcome auxotrophic mutations, for example, trpC or leuB, etc., fluorescent markers, and/or colorimetric markers (e.g., lacZ/β-galactosidase), and/or antibiotic resistance genes (e.g., amp or tet).

In yet another embodiment, a recombinant nucleic acid molecule or recombinant vector of the present invention includes an artificial ribosome binding site (RBS). The term "artificial ribosome binding site (RBS)" includes a site within an MRNA molecule (e.g., coded within DNA) to which a ribosome binds (e.g., to initiate translation) which differs from a native RBS (e.g., a RBS found in a naturally-occurring gene) by at least one nucleotide. Preferred artificial RBSs include about 5-6, 7-8, 9-10, 11-12, 13-14, 15-16, 17-18, 19-20, 21-22, 23-24, 25-26, 27-28, 29-30 or more nucleotides of which about 1-2, 3-4, 5-6, 7-8, 9-10, 11-12, 13-15 or more differ from the native RBS (e.g., the native RBS of a gene of interest). Preferably, nucleotides which differ are substituted such that they are identical to one or more nucleotides of an ideal RBS for a particular gene. Artificial RBSs can be used to replace the naturally-occurring or native RBS associated with a particular gene. Artificial RBSs preferably increase translation of a particular gene.

In another embodiment, a recombinant vector of the present invention includes sequences that enhance replication in bacteria (e.g., replication-enhancing sequences). In one embodiment, replication-enhancing sequences are derived from *E. coli*. In another embodiment, replication-enhancing sequences are derived from pBR322.

In yet another embodiment, a recombinant vector of the present invention includes antibiotic resistance genes. The term "antibiotic resistance genes" includes sequences which promote or confer resistance to antibiotics on the host organism. In one embodiment, the antibiotic resistance genes are selected from the group consisting of cat (chloramphenicol resistance) genes, tet (tetracycline resistance) genes, amp (ampicillin resistence), erm (erythromycin resistance) genes, neo (neomycin resistance) genes and spec (spectinomycin resistance) genes. Recombinant vectors of the present invention can further include homologous recombination sequences (e.g., sequences designed to allow recombination of the gene of interest into the chromosome of the host organism). For example, amyE sequences can be used as homology targets for recombination into the host chromosome.

Figure 8:
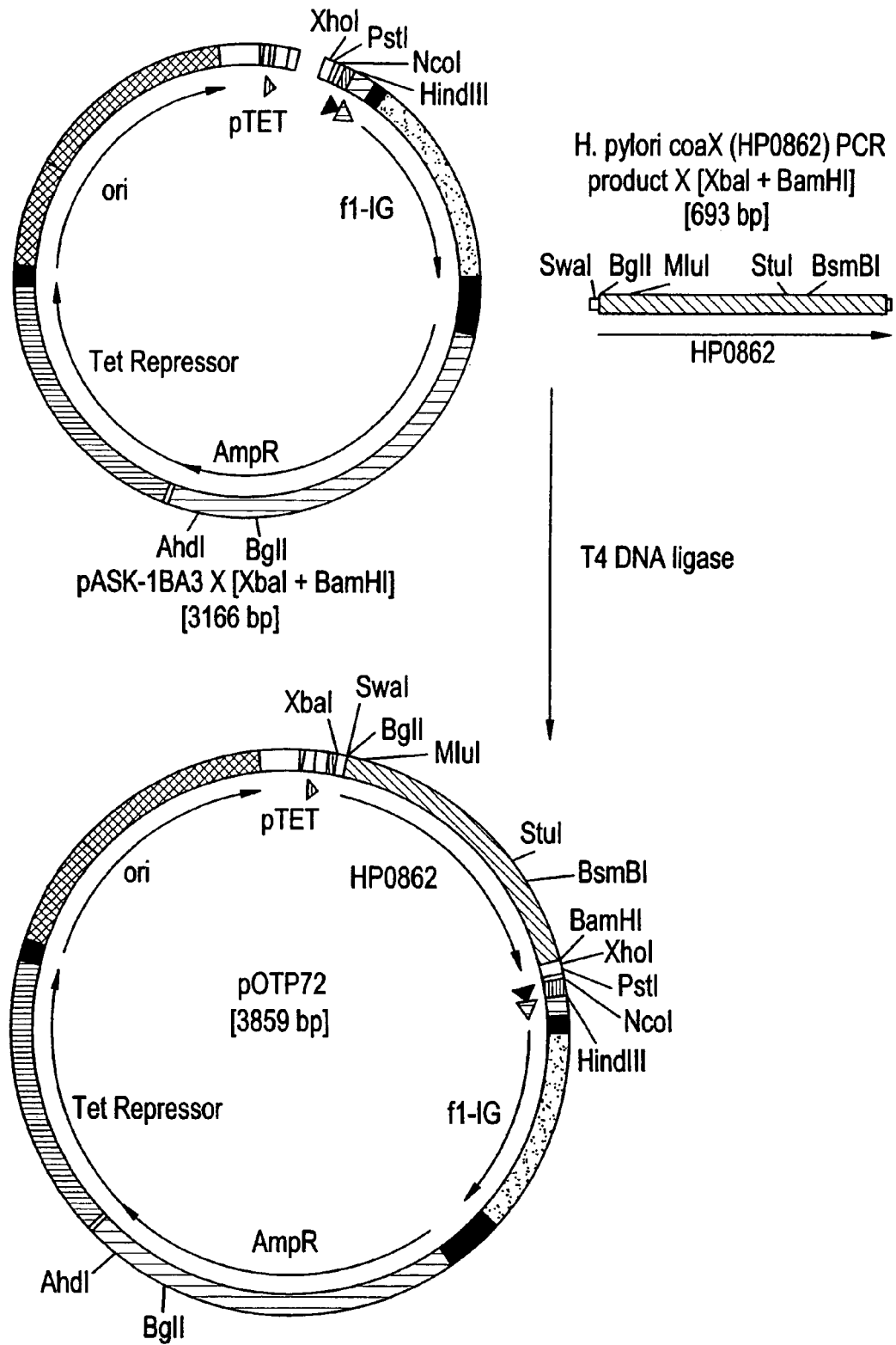
FIG. 8 is a schematic representation of the construction of pOTP72, a plasmid containing the *H. pylori* coaX gene.
Figure 9:
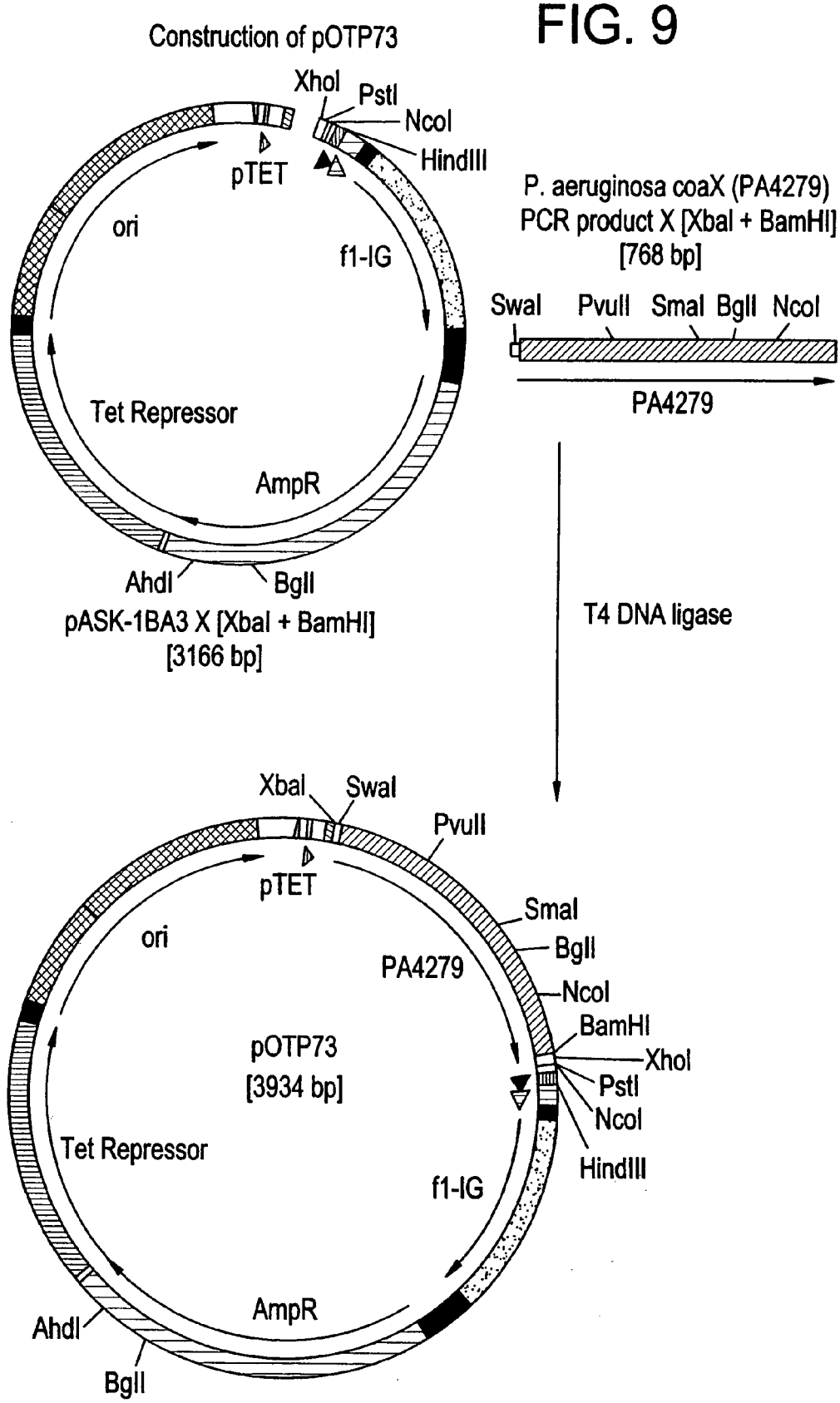
FIG. 9 is a schematic representation of the construction of pOTP73, a plasmid containing the *P. aeruginosa* coaX gene.
Figure 10:
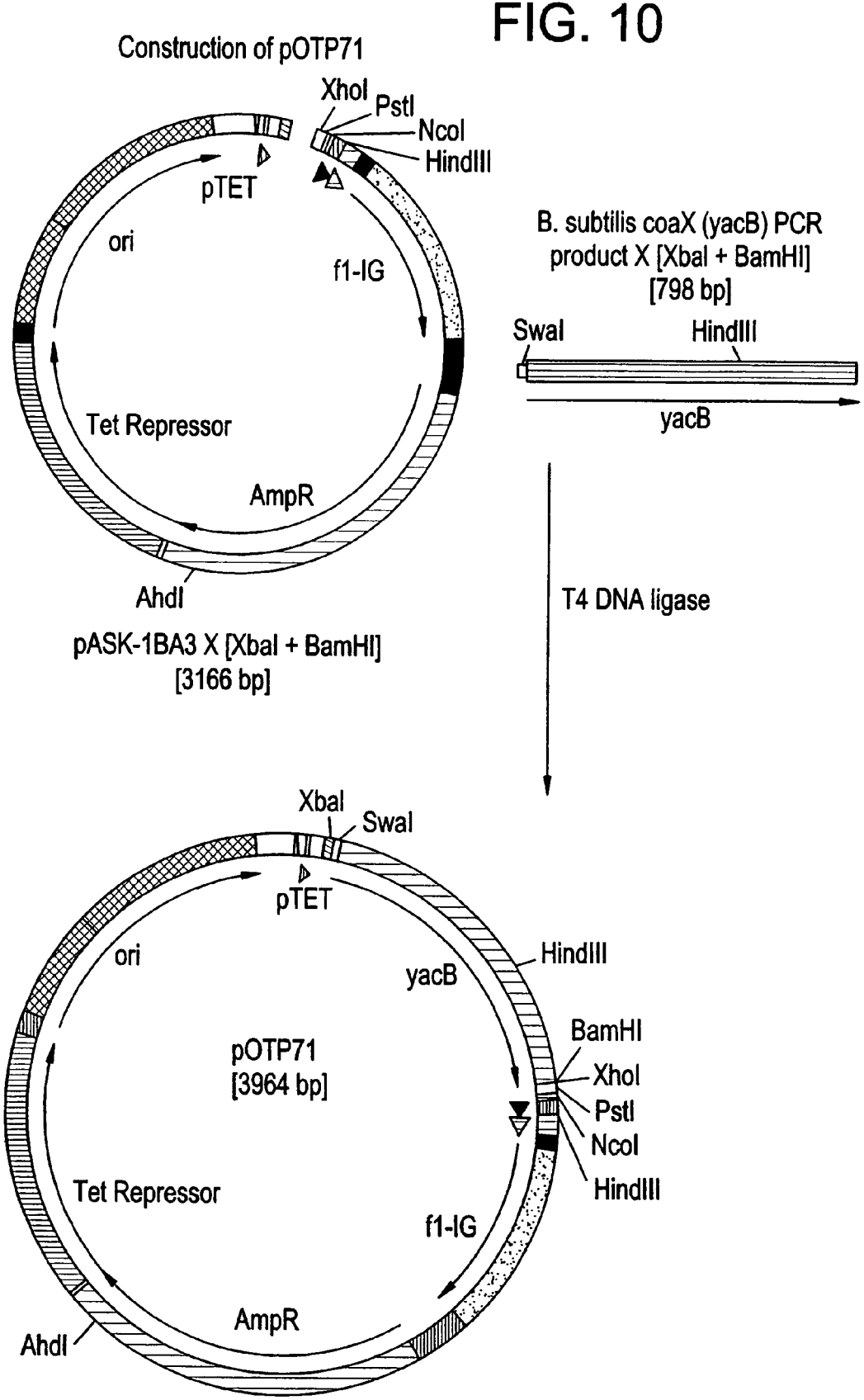
FIG. 10 is a schematic representation of the construction of pOTP71, a plasmid containing the *B. subtilis* coaX gene.

Preferred vectors of the present invention include, but are not limited to, vectors set forth in FIGS. 8-10. It will further be appreciated by one of skill in the art that the design of a vector can be tailored depending on such factors as the choice of microorganism to be genetically engineered, the level of expression of gene product desired and the like.

The methodologies of the present invention feature microorganisms, e.g., recombinant microorganisms, preferably including genes or vectors as described herein, in particular, pantothenate kinase encoding genes or vectos. The term "recombinant" microorganism includes a microorganism (e.g., bacteria, yeast cell, fungal cell, etc.) which has been genetically altered, modified or engineered (e.g., genetically engineered) such that it exhibits an altered, modified or different genotype and/or phenotype (e.g., when the genetic modification affects coding nucleic acid sequences of the microorganism) as compared to the naturally-occurring microorganism from which it was derived. Preferably, a "recombinant" microorganism of the present invention has been genetically engineered such that it overexpresses at least one bacterial gene or gene product (e.g., a pantothenate kinase encoding gene) as described herein, preferably a pantothenate kinase encoding-gene included within a recombinant vector as described herein. The ordinary skilled will appreciate that a microorganism expressing or overexpressing a gene product produces or overproduces the gene product as a result of expression or overexpression of nucleic acid sequences and/or genes encoding the gene product.

The term "overexpressed" or "overexpression" includes expression of a gene product (e.g., a pantothenate kinase) at a level greater than that expressed prior to manipulation of a microorganism or in a comparable microorganism that has not been manipulated. In one embodiment, a microorganism is genetically manipulated (e.g., genetically engineered) to overexpress a level of gene product greater than that expressed prior to manipulation of the microorganism or in a comparable microorganism which has not been manipulated. Genetic manipulation can include, but is not limited to, altering or modifying regulatory sequences or sites associated with expression of a particular gene (e.g., by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site or transcription terminator, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene routine in the art (including but not limited to use of antisense nucleic acid molecules, for example, to block expression of repressor proteins).

In another embodiment, the microorganism can be physically or environmentally manipulated to overexpress a level of gene product greater than that expressed prior to manipulation of the microorganism or in a comparable microorganism which has not been manipulated. For example, a microorganism can be treated with or cultured in the presence of an agent known or suspected to increase transcription of a particular gene and/or translation of a particular gene product such that transcription and/or translation are enhanced or increased. Alternatively, a microorganism can be cultured at a temperature selected to increase transcription of a particular gene and/or translation of a particular gene product such that transcription and/or translation are enhanced or increased.

Still other preferred recombinant microorganisms of the present invention are mutant microorganisms. As used herein, the term "mutant microorganism" includes a recombinant microorganism that has been genetically engineered to express a mutated gene or protein that is normally or naturally expressed by the microorganism. Preferably, a mutant microorganism expresses a mutated gene or protein such that the microorganism exhibits an altered, modified or different phenotype (e.g., has been engineered to express a mutated CoaA biosynthetic enzyme, for example, pantothenate kinase). In one embodiment, a mutant microorganism is designed or engineered such that it includes a mutant coaX gene, as defined herein. In another embodiment, a recombinant microorganism is designed or engineered such that it includes a mutant coaA gene, as defined herein. In another embodiment, a mutant microorganism is designed or engineered such that a coaX gene has been deleted (i.e., the protein encoded by the coaX gene is not produced). In another embodiment, a mutant microorganism is designed or engineered such that a coaA gene has been deleted (i.e., the protein encoded by the coaA gene is not produced). Preferably, a mutant microorganism has a mutant coaX gene or a mutant coaA gene, or has been engineered to have a coaX gene and/or coaA deleted, such that that the mutant microorganism encodes a "reduced pantothenate kinase activity". In the context of a whole microorganism, pantothenate kinase activity can be determined by measuring or assaying for a decrease in an intermediate or product of the CoA biosynthetic pathway, for example, measuring or assaying for 4'-phosphopantothenate, 4'-phosphopantothenylcysteine, 4'-phosphopantetheine, dephosphocoenzyme A, Coenzyme A, apo-acyl carrier protein (apo-ACP) or holo-acyl carrier protein (ACP) in the microorganism (e.g., in a lysate isolated or derived from the microorganism) or in the medium in which the microorganism is cultured. Alternatively, pantothenate kinase or CoaX activity can be determined by measuring or assaying for increased or decreased growth of the microorganism. Alternatively, pantothenate kinase activity can be determined indirectly by measuring or assaying for an increase in pantothenate which is the immediate precursor of pantothenate kinase.

In one embodiment, a recombinant microorganism of the present invention is a Gram negative organism (e.g., a microorganism which excludes basic dye, for example, crystal violet, due to the presence of a Gram-negative wall surrounding the microorganism). In another embodiment, a recombinant microorganism of the present invention is a Gram positive organism (e.g., a microorganism which retains basic dye, for example, crystal violet, due to the presence of a Gram-positive wall surrounding the microorganism). In a preferred embodiment, the recombinant microorganism is a microorganism belonging to a genus selected from the group consisting of *Escherichia, Heliobacter, Pseudomonas, Bordetella* and *Bacillus*. In a more preferred embodiment, the recombinant microorganism is of the genus *Escherichia* or *Bacillus*.

In another embodiment, the recombinant microorganism is a Gram negative (excludes basic dye) organism. In a preferred embodiment, the recombinant microorganism is a microorganism belonging to a genus selected from the group consisting of *Salmonella, Escherichia, Klebsiella, Serratia*, and *Proteus*. In a more preferred embodiment, the recombinant microorganism is of the genus *Escherichia*. In an even more preferred embodiment, the recombinant microorganism is *Escherichia coli*. In another embodiment, the recombinant microorganism is *Saccharomyces* (e.g., *S. cerevisiae*).

V. Screening Assays

Because CoaX is an essential factor in bacteria, proteins (e.g., enzymes) involved in the biosynthesis of CoA provide valuable tools in the search for novel antibiotics. In particular, the CoaX protein is a valuable target for identifying bacteriocidal compounds because it bears no resemblance in primary sequence to mammalian pantothenate kinase enzymes or CoaA's that are essential for beneficial enteric bacteria such as *E. coli*. Accordingly, the present invention also provides a method (also referred to herein as a "screening assay") for identifying modulators, i.e., candidate or test compounds or agents (e.g., peptides, peptidomimetics, small molecules or other drugs) that bind to CoaX, or have a stimulatory or inhibitory effect on, for example, coaX expression or CoaX activity.

In one embodiment, the invention provides assays for screening candidate or test compounds that are capable of binding to CoaX proteins or a biologically active portion thereof. In another embodiment, the invention provides assays for screening candidate or test compounds that modulate the activity of CoaX proteins or biologically active portions thereof. As used herein, the phrase "CoaX" activity includes any detectable or measurable activity of the CoaX protein, i.e., the protein encoded by the coaX gene of the present invention, for example, the coaX gene derived from a microorganism selected from the group consisting of *Aquifex* aeolicus, Bacillus anthracis, Bacillus halodurans, Bacillus stearothermophilus, Bacillus subtilis, Caulobacter crescentus, Chlorobium tepidum, Clostridium acetobutylicum, Dehalococcoides ethenogenes, Deinococcus radiodurans, Desulfovibrio vulgaris, Geobacter sulfurreducens, Pseudomonas putida, Rhodobacter capsulatus, Thiobacillus ferrooxidans, Streptomyces coelicolor, Synechocystis sp., Thermotoga maritima, Bordetella pertussis, Borrelia burgdorferi, Campylobacter jejuni, Clostridium difficile, Helicobacter pylori, Neisseria meningitidis, Neisseria gonorrhoeae, Porphyromonas gingivalis, Pseudomonas aeruginosa, Treponema pallidum, Xylella fastidiosa, Legionella pneumophila, and Mycobacterium tuberculosis. In a preferred embodiment, a CoaX activity is at least one of the following: (1) modulation of at least one step in the CoA biosynthetic pathway; (2) promotion of CoA biosynthesis; (3) phosphorylation of a CoaX substrate; (4) a pantothenate kinase activity; and (4) complementation of a CoaX mutant.

The test compounds of the present invention can be obtained using any of the numerous approaches in chemical compound library methods known in the art, including: natural compound libraries; biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad Sci. U.S.A.* 90:6909; Erb et al. (1994) *Proc. Natl. Acad Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med Chem.* 37:1233. Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In one embodiment, an assay is a microorganism-based assay in which a recombinant microorganism that expresses a CoaX protein or biologically active portion thereof is contacted with a test compound and the ability of the test compound to modulate CoaX activity is determined. Determining the ability of the test compound to modulate CoaX activity can be accomplished by monitoring, for example, growth, intracellular phosphopanthoate or CoA concentrations, or secreted pantothenate concentrations (as compounds that inhibit CoaX will result in a buildup of pantothenate in the test microorganism). CoaX substrate can be labeled with a radioisotope or enzymatic label such that modulation of CoaX activity can be determined by detecting a conversion of labeled substrate to intermediate or product. For example, CoaX substrates can be labeled with $^{32}P$, $^{14}C$, or $^{3}H$, either directly or indirectly, and the radioisotope detected by direct counting of radio emmission or by scintillation counting. Determining the ability of a compound to modulate CoaX activity can alternatively be determined by detecting the induction of a reporter gene (comprising a CoA-responsive regulatory element operatively linked to a nucleic acid encoding a detectable marker, e.g., luciferase), or detecting a CoA-regulated cellular response.

In yet another embodiment, a screening assay of the present invention is a cell-free assay in which a CoaX protein or biologically active portion thereof is contacted with a test compound in vitro and the ability of the test compound to bind to or modulate the activity of the CoaX protein or biologically active portion thereof is determined. In a preferred embodiment, the assay includes contacting the CoaX protein or biologically active portion thereof with known substrates to form an assay mixture, contacting the assay mixture with a test compound, and determining the ability of the test compound to modulate enzymatic activity of the CoaX on its substrates.

Screening assays can be accomplished in any vessel suitable for containing the microorganisms, proteins, and/or reactants. Examples of such vessels include microtiter plates, test tubes, and micro-centrifuge tubes. In more than one embodiment of the above assay methods of the present invention, it may be desirable to immobilize either CoaX protein, CoaX substrate, substrate analogs or a recombinant microorganism expressing CoaX protein to facilitate separation of products, ligands, and/or substrates, as well as to accommodate automation of the assay. For example, glutathione-S-transferase/CoaX fusion proteins can be adsorbed onto glutathione sepharose beads (Sigma Chemical, St. Louis, Mo.) or glutathione derivatized microtiter plates. Other techniques for immobilizing proteins on matrices (e.g., biotin-conjugation and streptavidin immobilization or antibody conjugation) can also be used in the screening assays of the invention.

This invention further pertains to novel agents identified by the above-described screening assays. Accordingly, it is within the scope of this invention to further use an agent identified as described herein in an appropriate animal model. For example, a CoaX modulating agent identified as described herein (e.g., an anti-bactericidal compound) can be used in an infectious animal model to determine the efficacy, toxicity, or side effects of treatment with such an agent.

CoaX modulators can further be designed based on the crystal structure of any one of the CoaX proteins of the present invention. In particular, based at least in part on the discovery of CoaX as an essential bacterial protein, one can produce significant quantities of the CoaX protein, for example using the recombinant methodologies as described herein, purify and crystallize said protein, subject said protein to Xray crystallographic procedures and, based on the determined crystal structure, design modulators (e.g., active site modulators, for example, competitor molecules, active site inhibitors, and the like), and test said designed modulators according to any one of the assays described herein.

This invention is further illustrated by the following examples which should not be construed as limiting. The contents of all references, patents and published patent applications cited throughout this application are incorporated herein by reference.

EXAMPLES

Example I

Assays for CoaX Genes or Activities

Assay for Pantothenate Kinase Genes or In Vivo Pantothenate Kinase Activity

In order to assay for genes encoding pantothenate kinase, the ability of plasmids containing these genes to complement the coaA15(Ts15) mutation in *E. coli* strain YH1 is tested at the non-permissive temperature of 43°-44° C. The defect in *E. coli* coaA15(Ts) has been identified as an S177L mutation that lies in a region that is highly conserved among bacterial pantothenate kinases, including CoaA of *B. subtilis*. Strain YH1 was constructed by P1 transduction from publically available strain DV62 (*Coli* Genetic Stock Center) to publically available strain YMC9 (ATCC), selecting for tetracycline resistance and screening for temperature sensitivity at 43° C.

In Vitro Assay for Pantothenate Kinase Activity

The assay for pantothenate kinase is based on the fact that under appropriate mildly acidic conditions (1% acetic acid in 95% ethanol), the product of the reaction, 4'-phosphopantothenate, binds to positively charged ion exchange paper, while the substrate, pantothenate, does not (see Vallari, D., Jackowski, S., and Rock, C., (1987), Journal of Biological Chemistry, Vol. 262, pp2468-2471, hereby incorporated by reference).

Cells of the strain to be assayed (bacteria, yeast, fungi, animal, or plant cells) are grown to late logarithmic phase or stationary phase, in 200 ml of an appropriate medium, for example Luria Broth or M9 minimal salts plus 0.5% glucose plus any necessary additives (for bacterial cells), at an appropriate temperature (25 to 44° C.). All subsequent steps are carried out at 0 to 40° C. The culture is cooled on ice for 10 minutes and the cells are concentrated by centrifugation at 7,000×g for 10 minutes. The cell pellet is rinsed by resuspending it in ice cold Buffer A (50 mM Tris-HCl, pH 7.4, 2.5 mM $MgCl_2$) and recentrifugation.

The rinsed cells are resuspended in the minimum possible volume (2-5 ml, depending on the size of the pellet) of Buffer A. The cells are then broken open by sonication in an inverted stainless steel test tube cap on ice for four bursts of 15 seconds each with 30 seconds of cooling between each burst. Cell debris is then removed from the lysed cells by centrifugation at 10,000×g for 10 minutes. The supernatant solution is then dialyzed for 12-16 hrs against two changes of one liter of Buffer A with 0.1 mM dithiothreitol added. Dialysis may be necessary to prevent the reaction product from undergoing further reactions catalyzed by the crude cell extract. Protein concentration in the dialyzed extracts is measured with a BCA Protein Assay Kit from BioRad.

The assay mix contains (final amounts or concentrations) about zero to 150 µg protein, 80 µM $^{14}$C-D-pantothenate, specific activity about 60,000 dpm/nmole (purchased from American Radiolabeled Chemicals, Inc.), 2.5 mM ATP (Sigma Chemical Company, sodium salt), 2.5 mM MgCl2, and 100 mM Tris HCl, pH 7.4, in a total volume of 40 µl. The reaction mix, minus the ATP, can be preincubated for about 1 to 10 minutes at an appropriate temperature (25 to 55° C.), in which case the reaction is started by addition of the ATP from a concentrated stock, also preincubated at the assay temperature.

After incubation for 1 to 10 minutes, the reaction is stopped by pipetting 35 µl of the reaction mix into an Eppendorf tube containing 1 ml of 95% ethanol, 1% acetic acid. After thorough mixing, the precipitated protein is pelleted in a microcentrifuge at top speed for one minute. The resulting supernatant solution is then applied to a one inch (or other appropriate size) disk of Whatman DE81 ion exchange filter paper prewetted with distilled water in a vacuum filtration manifold (for example Millipore 1225 Sampling Manifold). Each disk is then rinsed three times with 10 ml of 1% acetic acid in 95% ethanol. The top plate is then removed from the manifold and the completely exposed filter disks are each rinsed once more with 5 ml of the same rinse solution. The rinsed filters are then counted in a scintillation counter appropriatly set for $^{14}$C in 10 ml of Ecolume scintillation fluid. The specific activity of the pantothenate kinase can be calculated by determining the number of moles of substrate converted to product per mg protein per minute under various appropriate conditions of the assay.

Appropriate assay blanks include, but are not limited to, the standard mix except without ATP or without protein extract, or a complete mix incubated on ice for the shortest possible time before pipetting to the filter disk (preferably less than 10 seconds).

The assay should be checked for linearity with time up to 10 minutes, and for linearity with protein between zero and 150 µg. No more than 10% of the input 14C-pantothenate should be converted to phosphorylated product for the most accurate measurement of activity.

Temperature sensitivity of the pantothenate kinase enzyme can be tested by preincubating the reaction mix at various temperatures (25 to 55° C.) for various lengths of time (zero to 60 minutes) before addition of ATP to start the reaction.

For pantothenate kinases other than that encoded by the *E. coli* coaA gene, the optimum temperature, pH, $MgCl_2$ concentration, buffering ion, ATP (or other substrate containing a high energy phosphate donor) concentration, salt type and concentration, total ionic strength, etc., may need to be determined. For accurate determination of enzyme activity, it may be necessary to purify or partially purify the pantothenate kinase enzyme from crude extracts, for example by ammonium sulfate fractionation and/or by column chromatography.

The assay may be adapted for high throughput screening, for example by using γ-thio-ATP instead of ATP and then reacting the transfered thio group with a conveniently detectable signalling molecule (see Jeong, S., and Nikiforov, T., (1999), Biotechniques Vol. 27, pp 1232-1238; and Facemyer, K., and Cremo, C., (1992), Bioconjug. Chem. Vol. 3, pp 408-413, both of which are hereby incorporated by reference).

Example II

Figure 2:
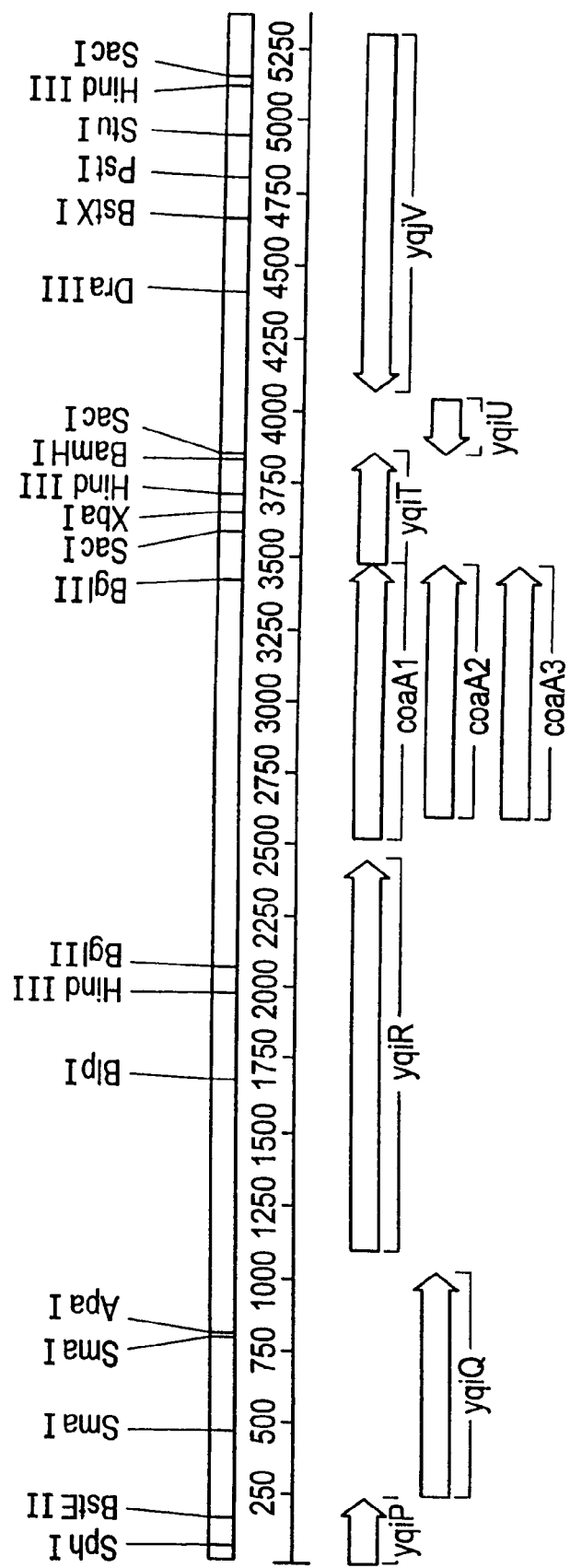
FIG. 2 is a schematic representation of the structure of the *Bacillus subtilis* genome in the region of the coaA gene. The scale is in base pairs and the significant open reading frames are shown by open arrows.

Identification and Characterization of a First *B. subtilis* Gene Encoding Pantothenate Kinase, the coaA Gene The annotated version of the *B. subtilis* genome sequence available on the "Subtilist" web site contained no gene labeled as coaA. However a homology search using the protein sequence of *E. coli* pantothenate kinase as a query sequence gave a good match with *B. subtilis* gene yqjS, which is annotated as "unknown; similar to pantothenate kinase." This gene appears to be the penultimate gene in an operon containing five open reading frames (FIG. 2). Two of the open reading frames encode proteins which are similar to D-serine dehydratase and to "ketoacyl reductase"; the other two have no known homologies. For the open reading frame corresponding to coaA, there are three possible start codons; each having a possible ribosome-binding site (RBS) associated with it. The three potential coaA ORFs were named coaA1, coaA2, and coaA3, from longest to shortest.

All three potential coaA open reading frames were cloned along with their respective RBSs by PCR followed by ligation into expression plasmid pAN229 to form plasmids pAN281, pAN282 and pAN283. pAN229 is a low copy vector in *E. coli* that provides expression from the SP01 phage $P_{15}$ promoter and can integrate by single crossover at bpr with tetracycline selection.

To determine if the cloned putative coaA ORFs actually encode a pantothenate kinase activity, several isolates of all three plasmids were transformed into the *E. coli* strain YH1, that contains the coaA15(Ts) allele. Transformants were streaked to plates incubated at 30° and 43° C. to test for complementation of the temperature sensitive allele. Isolates of all three coaA variants complemented well at 43° C., indicating that all three plasmid constructs encode an active pantothenate kinase. Accordingly, it can be concluded that the *B. subtilis* yqjS open reading frame codes for an active pantothenate kinase.

Example III

Deletion of the coaA Gene From the *B. subtilis* genome

Figure 3:
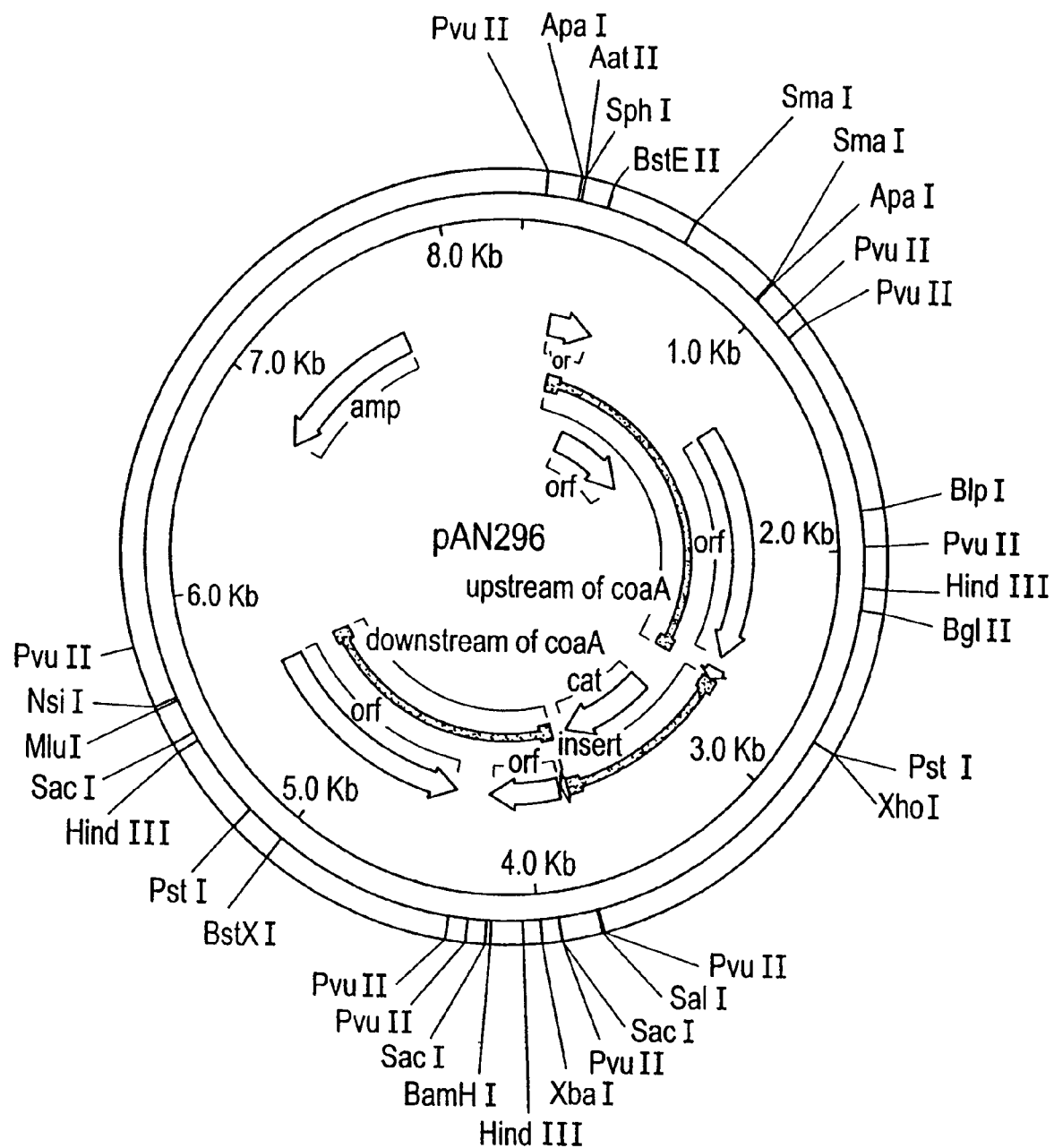
FIG. 3 is a schematic representation of the structure of pAN296, a plasmid designed to delete most of the *B. subtilis* coaA gene and substitute a chloramphenicol resistance gene.

The coaA gene of *B. subtilis* (yqjs) was deleted from the chromosome of a *B. subtilis* strain by conventional means. The majority of the coaA coding sequence was deleted from a plasmid clone and replaced by a chloramphenicol resistance gene (cat), while leaving approximately 1 kb of upstream and downstream sequence to allow homologous recombination with the chromosome, to give plasmid pAN296 (see FIG. 3). pAN296 was then used to transform a *B. subtilis* strain (PY79), selecting for chloramphenicol resistance. The majority of transformants result from a double crossover event that effectively substitutes the cat gene for the coaA gene. The transformed strain containing the coaA deletion—cat insertion, named PA861) grew normally indicating the presence of a second *B. subtilis* pantothenate kinase encoding gene described herein.

Example IV

Identification and Characterization of a Second *B. subtilis* Gene Encoding Pantothenate Kinase Activity, the coaX Gene After finding that deletion of the coaA gene from the chromosome of *B. subtilis* is not a lethal event (see Example III), it was concluded that *B. subtilis* must contain a second gene that encodes an active pantothenate kinase, since pantothenate kinase is an essential enzyme activity.

A second pantothenate kinase-encoding gene was identified by complementing the *E. coli* strain YH1 (coaA15(Ts)) with a *B. subtilis* gene bank and selecting for transformants that were able to grow at 43° C. Found among the transformants were two families of plasmids that had overlapping restriction maps within each family, but not between the families. As expected, the restriction map of one family was identical to that predicted from the *B. subtilis* genome sequence for the homologue of the *E. coli* coaA gene (which we named coaA also, see above) and surrounding sequences. The other family had a restriction map that was completely non-overlapping with the first.

DNA sequencing of the ends of the cloned inserts from the second family showed that the clones came from a region of the *B. subtilis* chromosome that includes the 3' end of the ftsH gene, the 5' end of the sul gene, and all of the yacB, yacC, yacD, cysK, pabB, pabA and pabC genes. None of the open reading frames of these cloned inserts showed homology to any known pantothenate kinase sequences, either prokaryotic or eukaryotic.

Figure 4:
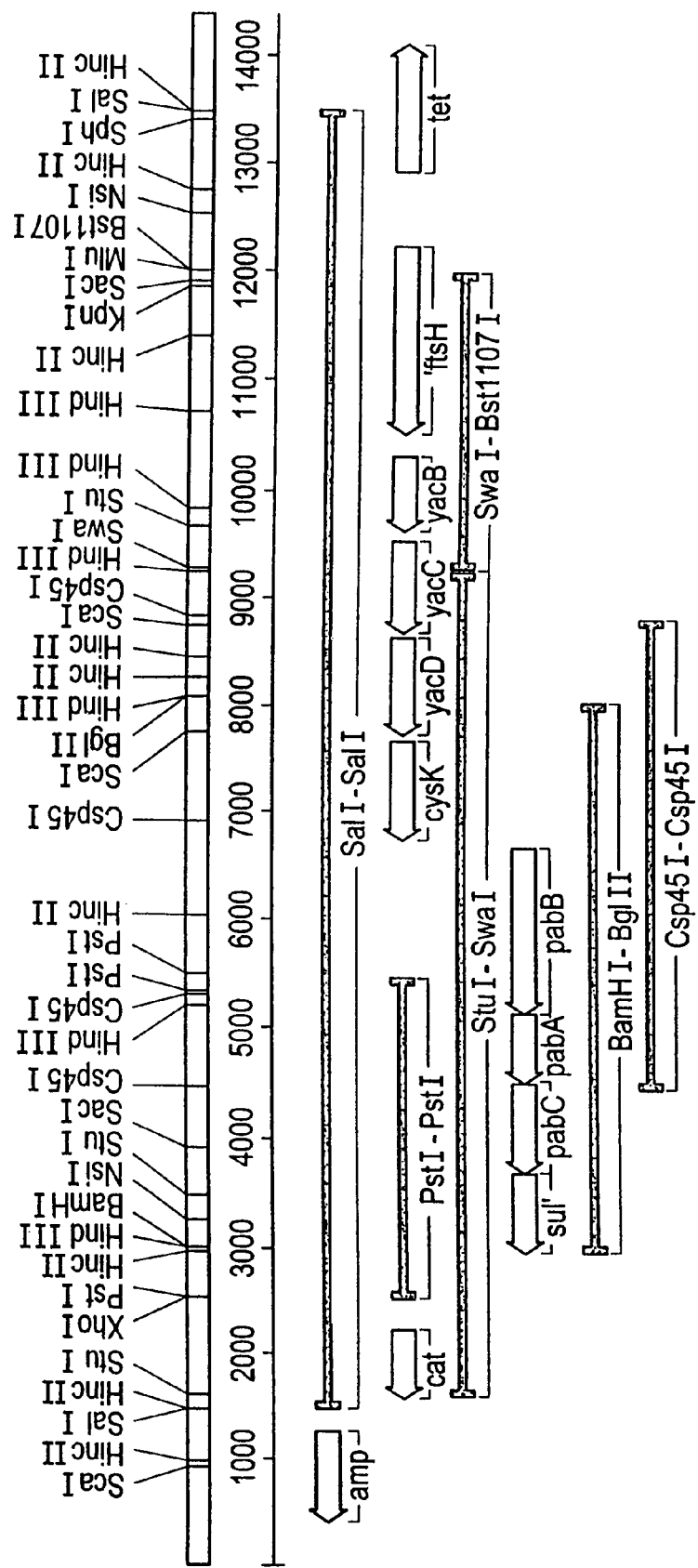
FIG. 4 is a schematic representation of the structure of the *Bacillus subtilis* genome in the region of the coaX (yacB) gene. The scale is in base pairs, the significant open reading frames are shown by open arrows and certain predicted restriction fragments are indicated by thick bars.
Figure 5:
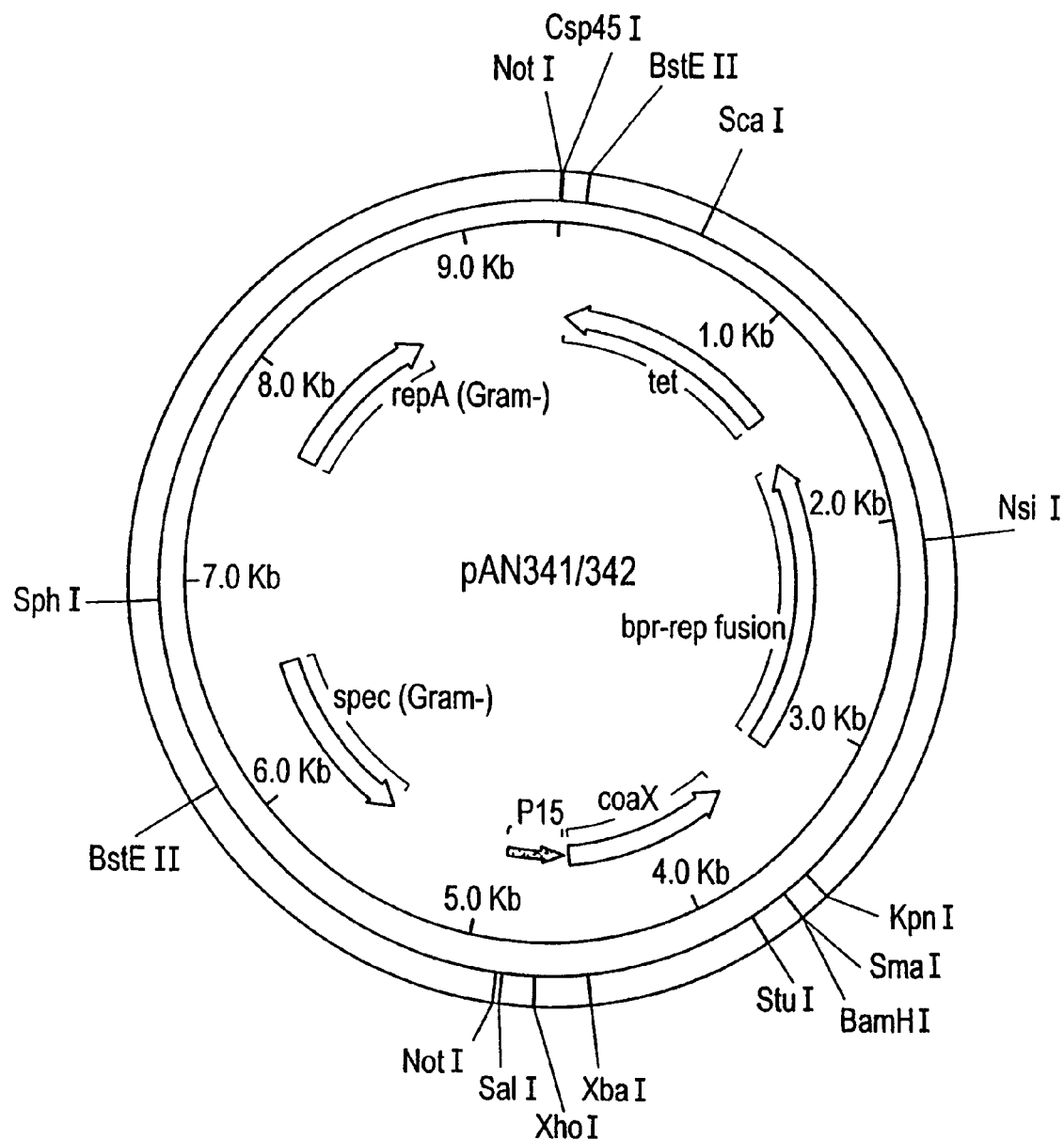
FIG. 5 is a schematic representation of the structure of pAN341 and pAN342, two independent PCR-derived clones of *B. subtilis* yacB (renamed herein as coaX).

Several deletions were created through the *B. subtilis* genomic sequences in the cloned inserts. Each deletion was tested for complementation of the *E. coli* temperature sensitive pantothenate kinase. In particular, a deletion that removed all DNA between a Stu I site in the cloning vector and a Swa I site in the yacC gene, leaves yacB as the only intact open reading frame in the cloned insert (see FIG. 4). This deleted plasmid still complemented the *E. coli* pantothenate kinase mutant. However, another deletion that removed DNA from the Swa I site in yacC through a Bst11071 site in the (already truncated) ftsH gene, could not complement the *E. coli* pantothenate kinase mutant. From these results, it was concluded that the yacB open reading frame was responsible for the complementation activity. To confirm that yacB is a pantothenate kinase gene, the yacB ORF plus 112 base pairs of downstream flanking sequence was amplified by PCR in two independent reactions and cloned downstream of a constitutive promote to give plasmids pAN341 and pAN342 (FIG. 5). Both pAN341 and pAN342 complemented the defect in YH1 at 44° C., while a control plasmid, which has the same backbone, but expresses panBCD instead of yacB did not. This confirmed that the yacB open reading frame was responsible for the complementation of YH1.

As such, a novel gene that encodes pantothenate kinase activity in *B. subtilis* has been discovered that is not related by homology to any previously known pantothenate kinase gene. This gene has been renamed coaX, as a second, alternative gene that encodes an enzyme that catalyzes the first step in the pathway from pantothenate to CoaA. In *B. subtilis* strains deleted for coaA, coaX is an essential gene.

Several homologues of the *B. subtilis* coaX gene were identified by homology searching of various publically available databases using the published yacB (coaX) open reading frame sequence and predicted amino acid sequence (as set forth in SEQ ID NOs:15 and 16 respectively). In two cases (Mycobacterium tuberculosis and *Streptomyces coelicolor*) the homologous coaX genes are adjacent to, or almost adjacent to, pantothenate biosynthetic genes, consistent with these homologs having a role in pantothenate metabolism. The CoaX proteins show no homology to the CoaA family of pantothenate kinases, nor to the eukaryotic family of pantothenate kinases exemplified by PanK of *Saccharomyces cerevisiae*.

Alignment of the amino acid sequences of several bacterial CoaX homologs with the amino acid sequence predicted from translating the *B. subtilis* yacB ORF described in the published *B. subtilis* genome sequence revealed that the CoaX proteins from other bacteria contained additional amino acid residues at their carboxy-terminal ends. Moreover, these extensions beyond the end of the predicted amino acid sequence for the *B. subtilis* gene product contained two relatively well conserved segments of sequence.

Translation of nucleotide sequences just downstream from the stop codon of the *B. subtilis* yacB ORF in a different reading frame revealed the existence of amino acid sequences very similar to the carboxy-terminal extensions of the other bacterial CoaX proteins. It is thus believed that an error exists in the published DNA sequence of the *B. subtilis* yacB ORF sequence that causes a frame shift leading to an artifactual downstream amino acid sequence and premature termination.

The PCR-generated sequences of *B. subtilis* coaX in pAN341 and pAN342 (described above) contain enough downstream flanking sequence to encode the putative carboxy-terminal extension described above, which is consistent with the result that the clones were functional in the complementation assay. However when the 3' PCR primer was positioned to include only the shorter yacB ORF predicted from the published sequence, but not to include the putative carboxy-terminal extension, then the resulting plasmids, pAN329 and pAN330 (similar in structure to pAN341 and pAN342; see FIG. 5), did not complement the defect in YH1. This result supports the notion that the published yacB coding sequence contains a frame-shift error, and that the carboxy-terminal end of CoaX is necessary for pantothenate kinase activity. A predicted correct nucleotide sequence for *B. subtilis* coaX is set forth as SEQ ID NO:1 and the translated amino acid sequence is set forth as SEQ ID NO:2. A multiple sequence alignment of the CoaX amino acid sequences of *B. subtilis* and 11 homologues thereof is set forth in FIG. 6.

Example V

Deleting the Second Pantothenate Kinase Gene, coaX Gene From *B. subtilis*

With the knowledge gained above concerning the existence and nature of coaX, one can create a deletion of the coaX open reading frame from the *B. subtilis* chromosome that will remove the encoded activity, and that will not adversely affect the expression of the genes downstream from coaX. In such a deleted strain, the coaA gene will be the only gene that encodes pantothenate kinase.

Figure 7:
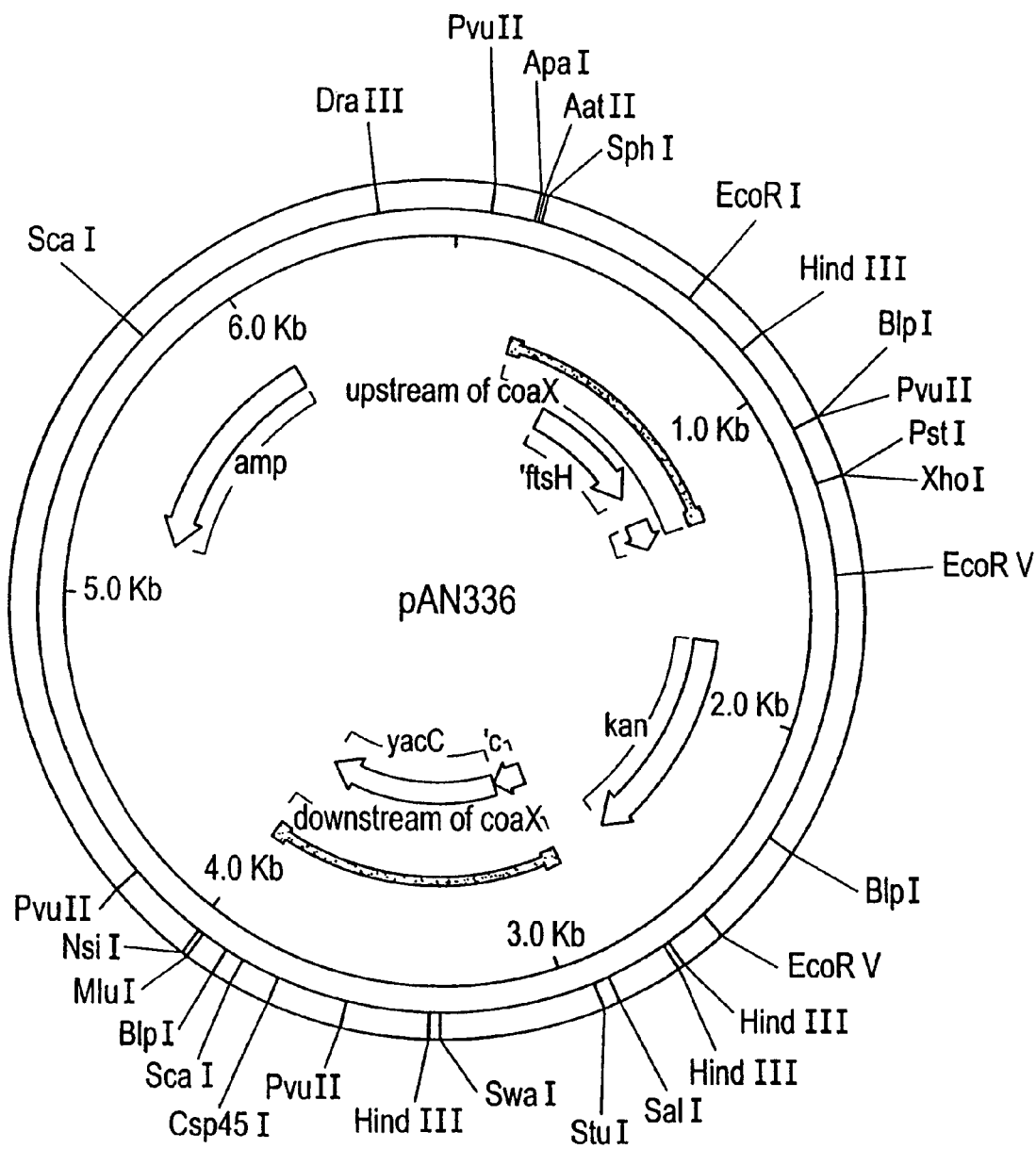
FIG. 7 is a schematic representation of the structure of pAN336, a plasmid designed to delete *B. subtilis* coaX from its chromosomal locus and replace it with a kanamycin resistence gene.

To delete the coaX gene from *B. subtilis*, plasmid pAN336, which contains upstream and downstream homology for double crossover, was constructed with a kanamycin resistance gene replacing most of the coaX ORF (FIG. 7). Strain PY79 was transformed to kanamycin resistance by pAN336, and an isolate confirmed to have resulted from a double crossover by PCR was named PA876. As predicted, deletion of coaX by itself is not lethal for *B. subtilis*. Furthermore, chromosomal DNA from PA876 would not transform competent PA861 (PY79 ΔcoaA::cat) to kanamycin resistance. These results indicate that it is the combination of ΔcoaA::cat and ΔcoaX::kan that is lethal for *B. subtilis*, confirming that *B. subtilis* contains two unlinked genes that encode pantothenate kinase, coaA and coaX, and that either gene alone is capable of supplying sufficient pantothenate kinase for a normal rate of growth.

Example VI

Identification of coaX Homologs in Other Microbes

Database analyses reveal that many bacteria, in addition to *B. subtilis*, contain homologs of the CoaX pantothenate kinase. As shown in Tables 1 and 2, both nonpathogenic and pathogenic bacteria can be found that contain homologs of this novel gene.

TABLE 1

CoaX homologs in Non-Pathogens

| Species | Genome complete | CoaA homolog | CoaX homolog |
|---|---|---|---|
| *Aquifex aeolicus* | Yes | NONE | RAA00700<br>aq_1924<br>AAC07720.1<br>pir\|\|E70465 |
| *Bacillus halodurans* | Yes | BH2875<br>BAB06594.1 | BH0086 |
| *Bacillus stearothermophilus* | No | NONE? | gnl\|UOKNOR_1422\|bstear_.Contig467 |
| *Bacillus subtilis* | Yes | RBS02372 YqjS<br>BAA12625.1<br>CAB14308.1<br>pir\|\|C69965 | RBS00070 YacB<br>BAA05305.1<br>CAB11846.1<br>pir\|\|S66100 |
| *Caulobacter crescentus* | No | NONE? | gnl\|TIGR\|C.crescentus_12574 |
| *Chlorobium tepidum* | No | NONE? | gnl\|TIGR\|C.tepidum_3499 |
| *Clostridium acetobutylicum* | No | NONE? | RCA03301<br>gnl\|GTC\|C.aceto_gnl |
| *Dehalococcoides ethenogenes* | No | NONE? | gnl\|TIGR_61435\|deth_1587 |
| *Deinococcus radiodurans* | Yes | NONE | AAF10040.1<br>pir\|\|E75516 |
| *Desulfovibrio vulgaris* | No | NONE? | BAA21476.1<br>P37564<br>gnl\|TIGR_881\|dvulg_1371 |
| *Geobacter sulfurreducens* | No | NONE? | gnl\|TIGR_35554\|gsulf_121 |
| *Pseudomonas putida* KT2440 | No | NONE? | gnl\|TIGR\|pputida_10724 |
| *Rhodobacter capsulatus* | No | NONE? | RRC02473 |
| *Thiobacillus ferrooxidans* | No | NONE? | gnl\|TIGR\|t_ferrooxidans_6155 |
| *Streptomyces coelicolor* | No | COAA_STRCO<br>g8469186<br>pir\|\|T35567 | SCE94.31c<br>CAB40880.1 |
| *Synechocystis* sp. | Yes | NONE | ORF_ID:slr0812<br>BAA18120 |
| *Thermotoga maritima* | Yes | NONE | TM0883<br>AAD35964.1<br>pir\|\|D72320 |

TABLE 2

CoaX homologs in Pathogens

| Pathogen | Genome complete | CoaA homolog | CoaX homolog | Comments |
|---|---|---|---|---|
| Haemophilus influenzae | Yes | RHI13313 | NONE | |
| Streptococcus pyogenes | No | RST01295 | NONE | |
| Yersinia pestis | No | RYP02180 | NONE | |
| Vibrio cholerae | Yes | VC0320 | NONE | |
| Bacillus anthracis | No | NONE? | YES | |
| Bordetella pertussis | No | NONE? | BAF (BVG ACCESSORY FACTOR) | |
| Borrelia burgdorferi | Yes | NONE | BB0527 | |
| Campylobacter jejuni | Yes | NONE | Cj0394c | |
| Clostridium difficile | No | NONE? | YES | |
| Helicobacter pylori | Yes | NONE | jhp0796 (strain J99) HP0862 (strain 26695) AAD07916.1 | |
| Neisseria meningitidis | Yes | NONE | NMA0357 (strain Z2491) NMB2075 (strain MC58) | CoaX is fused to BirA |
| Neisseria gonorrhoeae | No | NONE? | RNG00193 | CoaX is fused to BirA |
| Porphyromonas gingivalis | No | NONE? | RPG01037 gnl|TIGR|P.gingivalis_GPG.con | |
| Pseudomonas aeruginosa | Yes | NONE | RPA06755 PA4279 AAG07667.1 | |
| Treponema pallidum | Yes | NONE | RTP00155 (TP0431) | |
| Xylella fastidiosa | Yes | NONE | XF1795 | |
| Legionella pneumophila | No | | gnl|CUCGC_446|lpneumo_C030598.2F12.S | |
| Mycobacterium leprae | No | MLCB1222.23 | | |
| Mycobacterium tuberculosis | Yes | RMT04257 | RMT02984 (Rv3600c) | RMT04257 |

Of particular interest are the seven human pathogens *Helicobacter pylori, Borrelia burgdorferi, Pseudomonas aeruginosa, Campylobacter jejuni, Neisseria meningitidis, Treponema pallidum*, and *Bordetella pertussis*, that contain the CoaX pantothenate kinase as their sole pantothenate kinase activity. For these bacteria, the CoaX pantothenate kinase represents an attractive target for screening for new antibiotics effective against one or more of these pathogens. One can overproduce the particular CoaX pantothenate kinase and use the isolated protein, partially purified protein or crude cell extracts to screen in vitro for compounds that modulate (e.g. inhibit) the pantothenate kinase activity. Alternatively, one can isolate compounds that specifically bind to the enzyme and test their ability to block the enzyme's activity. A known kinase activity represents a particularly favorable target for high-throughput screening for compounds that modulate or decrease that activity.

Also of interest are other pathogens which contain a coaX gene, in particular, if it is demonstrated that these other pathogens contain only a single pantothenate kinase encoded by the coaX gene. Examples of such bacteria are *Porphyromonas gingivalis, Neisseria gonorrhoeae, Clostridium difficile*, and *Bacillus anthracis*, all of which have been shown to contain a coaX homolog. Determination whether or not they also contain a second pantothenate kinase encoded by a coaA homolog can be determined according to the methodologies taught in Examples II-IV.

Example VII

Identification of coaX Homologs in Human Pathogens Lacking a Conventional Prokaryotic Pantothenate Kinase Human pathogens *Helicobacter pylori* (agent in gastoenteritus, stomach ulcers, and potentially stomach cancer), *Borrelia burgdorferi* (agent in Lyme's disease), *Bordetella pertussis* (agent in whooping cough), and *Pseudomonas aeruginosa* (opportunistic pathogen in cystic fibrous) all contain homologs of the coaX gene of *B. subtilis* and no homologs of the coaA gene of *E. coli* or *B. subtilis*. This is also true for the pathogens *Treponema pallidum, Campylobacter jejuni*, and *Neisseria meningitidis*. We have shown in *B. subtilis* that in the absence of the coaA gene product ($\Delta$coaA mutant), the coaX gene product is essential, providing the only pantothenate kinase activity required for the synthesis of the essential compound, Coenzyme A. Therefore it can be predicted that the pantothenate kinase encoded by the coaX homolog in the above listed pathogens is an essential enzyme for each mentioned pathogen and is required for the survival and growth of the pathogen. In fact it has been reported that the coaX homolog in *Bordetella pertussis*, called baf, and classified as an auxiliary regulatory factor rather than a critical enzyme, is an essential gene (see Wood, G. E. and R. L. Friedman (2000) FEMS Microbial. Lett. 193(1):25-30).

The CoaX protein is a favorable target for the development and screening of new antibiotics. First, the pantothenate kinase encoded by the coaX gene is an essential enzyme in a group of human pathogens, making it a good target for inactivation. Second, the enzyme activity (kinase) of the isolated CoaX protein or its homologs provides an ideal assay to screen large numbers of compounds (combinatorial libraries, etc.) for their ability to specifically inhibit the pantothenate kinase activity both in vitro and in vivo.

Example VIII

Production of CoaX Proteins From Pathogens for Use in Screening Assays

To provide the pantothenate kinase proteins for screening assays, the coaX gene homolog was obtained by PCR from isolated, whole genome DNA of *Helicobacter pylori* (ATCC 700392), *Borrelia burgdorferi* (ATCC 35210), *Bordetella pertussis* (ATCC 9797), and *Pseudomonas aeruginosa* (ATCC 47085). Coding sequences for proteins with homology to *B. subtilis* CoaX were amplified by PCR using the primers and templates given in Table 3 with Pfx DNA polymerase (Life Technologies) according to the manufacture's specifications. The PCR primers incorporate a XbaI restriction enzyme recognition site at the 5' end of each product and a BamHI restriction enzyme recognition site at the 3' end of each product. PCR products were digested with a mixture of XbaI and BamHI and then purified by preparative agarose gel electrophoresis.

TABLE 3

PCR primers and template DNAs used to amplify coding sequences homologous to *B. subtilis* coaX.

| Organism | coaX homolog | Template DNA | 5' amplification primer | 3' amplification primer |
|---|---|---|---|---|
| *Bacillus subtilis* 168 | yacB | Strain RL-1 genomic DNA | TP175 5'-GGGTCTA GAAAAGGAGG AATTTAAATG TTACTGGTTA TCGATGTGGG GAACACC-3' (SEQ ID NO: 78) | TP176 5'-GGGATCC TTATACACTT CCTACGCGGT TTCTTTCATA AATCAAT TCC-3' (SEQ ID NO: 79) |
| *Bordetella pertussis* | baf | Strain ATCC 9797 genomic DNA | TP177 5'-GGGTCTA GAAAAGGAGG AATTTAAATG ATTATCCTCA TCGACTCCG GC-3' (SEQ ID NO: 80) | TP178 5'-GGGATCC TTAGGCCGTT GGCGCGCCTT GCGCGG CG-3' (SEQ ID NO: 81) |
| *Borrelia burgdorferi* | BB0527 | Strain ATCC 35210 genomic DNA | TP171 5'-GGGTCTA GAAAAGGAGG AATTTAAATG AATAAACCTT TATTATCAGA ATTGATAATT GATATTGGAA ATACCA GC-3' (SEQ ID NO: 82) | TP172 5'-GGGATCC TTAATTAACA AACTTAAAGT CAATAGAATT TCCTAAAATT CTAACGCCTT CTACAG-3' (SEQ ID NO: 83) |
| *Helicobacter pylori* 26695 | HP0862 | Strain ATCC 700392 genomic DNA | TP167 5'-GGGTCTA GAAAAGGAGG AATTTAAATG CCAGCTAGGC AATCTTTTAC AGATTTGAAA AACCTGG-3' (SEQ ID NO: 84) | TP168 5'-GGGATCC TTATTTGCAT TCTAGTATCC CTGCTTTTTT AAGAGCGATT TCCATCCC GTC-3' (SEQ ID NO: 85) |

TABLE 3-continued

PCR primers and template DNAs used to amplify coding sequences homologous to B. subtilis coaX.

| Organism | coaX homolog | Template DNA | 5' amplification primer | 3' amplification primer |
|---|---|---|---|---|
| Pseudomonas aeruginosa PA01 | PA4279 | Strain ATCC 47085 genomic DNA | TP169 5'-GGGTCTA GAAAAGGAGG AATTTAAATG ATTCTTGAGC TCGACTGTGG AAACTCG CTG-3' (SEQ ID NO: 86) | TP170 5'-GGGATCC TTACTCAATC GGGCAAGCCA GTGCCAGCCC TACG-3' (SEQ ID NO: 87) |

The purified PCR products were cloned by ligation with plasmid vector pASK-1BA3 (Sigma-Genosys) which had been digested with XbaI and BamHI followed by transformation into strains LH-1 and XL1-Blue/MRF'kan. Plasmids containing inserts were identified by restriction enzyme digestion of plasmid DNA isolated from selected transformants. Examples of plasmids containing the H. pylori (pOTP72), P. aeruginosa (pOTP73), or B. subtilis (pOTP71) coaX gene are shown in FIGS. 8, 9 and 10, respectively. The identity of inserts in plasmids is confirmed by DNA sequence analysis.

The pantothenate kinase activity of each of the above cloned coaX homologs can be demonstrated by transforming the plasmids described above into E. coli strain YH1 containing the coaA15(Ts) mutation and looking for complementation at the non-permissive temperature of 43°-44° C. For example, as shown in Table 4, transformation of E. coli YH1 containing the coaA15(Ts) with plasmid pOTP72 containing the cloned H. pylori coaX gene (HP0862) or plasmid pOTP73 containing the cloned P. aeruginosa coaX gene (PA4279) enabled the E. coli cells with the temperature sensitive coaA gene product to grow at 44° C. as is also the case when these cells were transformed with the plasmid containing the B. subtilis coaX gene (pOTP71). These experiments confirm that the coaX homologs in H. pylori and P. aeruginosa due indeed each encode an active pantothenate kinase.

TABLE 4

Transformation of YH1 (coaA15(Ts)) with coaX ligation mixtures and control plasmid DNA

| DNA | Number of colonies at 30° C. | Number of colonies at 44° C. |
|---|---|---|
| NONE | zero | zero |
| Ligated, cut vector | 5 | zero |
| Uncut vector (pASK-1BA3) | >500 | zero |
| B. subtilis coaX, pool A ligation | 74 | 67 |
| B. subtilis coaX, pool B ligation | 230 | 160 |
| H. pylori coaX (HP0862) pool A ligation | 53 | 38 |

TABLE 4-continued

Transformation of YH1 (coaA15(Ts)) with coaX ligation mixtures and control plasmid DNA

| DNA | Number of colonies at 30° C. | Number of colonies at 44° C. |
|---|---|---|
| H. pylori coaX (HP0862) pool B ligation | 99 | 56 |
| P. aeruginosa coaX (PA4279) pool A ligation | 366 | 279 |
| P. aeruginosa coaX (PA4279) pool B ligation | 282 | 359 |

Since the coaX homologs cloned in pASK-1BA3 were inserted downstream of a Tet-inducible promoter, enzyme for in vitro screening assays can be obtained by inducing gene expression as described by Sigma-Genosys, and then isolating the overproduced pantothenate kinase by conventional protein purification procedure. Alternatively, the coaX gene can be cloned into any of various protein or peptide fusion expression vectors that facilitate purification of the protein. For example, *Helicobacter pylori, Borrelia burgdorferi, Bordetella pertussis*, and *Pseudomonas aeruginosa* coaX genes can be cloned into protein fusion expression vectors such as those available from companies including but not limited to Qiagen™ or Invitrogen™ to produce a His tagged CoaX fusion proteins or glutathione-S-transferase/CoaX fusion proteins which can be isolated by binding to nickel affinity or glutathione sepharose resins, respectively.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A method for identifying compounds that inhibit pantothenate kinase activity, comprising:
   a) contacting a cell comprising a recombinant expression vector expressing a CoaX protein having pantothenate kinase activity with a test compound, wherein said CoaX protein is encoded by a naturally-occurring, microbial coaX gene; and
   b) determining the ability of the test compound to inhibit pantothenate kinase activity in said cell;
   wherein inhibition of pantothenate kinase activity identifies the compound as an inhibitor of pantothenate kinase activity.

2. The method of claim 1, wherein the recombinant cell is dependent on the CoaX protein for growth.

3. The method of claim 1, wherein the recombinant cell is not dependent on the CoaX protein for growth.

4. The method of claim 1, wherein the recombinant cell further comprises a CoaA protein endoced by a coaA gene.

5. The method of claim 4, wherein the CoaA protein is expressed from a recombinant expression vector.

6. A method for identifying compounds that inhibit CoaX pantothenate kinase activity, comprising:
   a) contacting a cell comprising a recombinant expression vector expressing a CoaX protein having pantothenate kinase activity encoded by a naturally-occurring, microbial coaX gene with a test compound, wherein said cell is dependent on the CoaX protein encoded by the coaX gene for growth;
   b) determining the ability of the test compound to inhibit growth of said cell; and
   c) comparing the ability of the cell comprising the recombinant expression vector expressing the CoaX protein encoded by the coaX gene to grow with the ability of a cell comprising a CoaA protein encoded by a coaA gene to grow;
   wherein the inability of the cell comprising the recombinant expression vector expressing the CoaX protein encoded by the coaX gene to grow and the ability of the cell comprising the CoaA protein encoded by the coaA gene to grow identifies the compound as an inhibitor of CoaX pantothenate kinase activity.

7. The method of claim 4 or 6, wherein the cell comprising the CoaA protein encodes a pantothenate kinase polypeptide with reduced activity.

8. The method of claim 7, wherein said reduced pantothenate kinase activity is due to an environmental manipulation.

9. The method of claim 4 or 6, wherein the CoaA protein is expressed from a recombinant expression vector.

10. The method of claim 1 or 6, wherein said cell comprising the recombinant expression vector expressing the CoaX protein is a Gram negative microorganism.

11. The method of claim 1 or 6, wherein said cell comprising the recombinant expression vector expressing the CoaX protein is a Gram positive microorganism.

12. The method of claim 6, wherein said cell comprising the CoaA protein is a Gram negative microorganism.

13. The method of claim 6, wherein said cell comprising the CoaA protein is a Gram positive microorganism.

14. The method of claim 1 or 6, wherein said cell comprising the recombinant expression vector expressing the CoaX protein is of the genus *Bacillus* or *Escherchia*.

15. The method of claim 1 or 6, wherein said cell comprising the recombinant expression vector expressing the CoaX protein is *Bacillus subtilis* or *Escherchia coli*.

16. The method of claim 6, wherein said cell comprising the CoaA protein is of the genus *Bacillus* or *Escherchia*.

17. The method of claim 6, wherein said cell comprising the CoaA protein is *Bacillus subtilis* or *Escherchia coli*.

18. The method of claim 1 or 6, wherein said cell comprising the recombinant expression vector expressing a CoaX protein is a non-pathogenic bacterium and said coaX gene is derived from a pathogenic bacterium.

19. The method of claim 1 or 6, wherein the recombinant expression vector is selected from the group consisting of pAN296 (SEQ ID NO: 71), pAN336 (SEQ ID NO: 72), pOTP71 (SEQ ID NO: 75), pOTP72 (SEQ ID NO: 76), pOTP73 (SEQ ID NO: 77), and pAN341 (SEQ ID NO: 73).

20. The method of claim 1 or claim 6, wherein the coaX gene is a coaX gene from a pathogenic bacterium selected from the group consisting of *Bordetella pertussis, Borrelia burgdorferi, Campylobacter jejuni, Clostridium difficile, Helicobacter pylori, Neisseria meningitidis, Pseudomonas aeruginosa, Treponema pallidumu* and *Xylella fastidiosa*.

21. The method of claim 1 or 6, wherein the coaX gene is a coaX gene from a pathogenic bacterium selected from the group consisting of *Bacillus anthracis, Bordetella pertussis, Borrelia burgdorferi, Campylobacter jejuni, Clostridium difficile, Helicobacter pylori, Neisseria meningitidis, Neisseria gonorrhoeae, Porphyromonas gingivalis, Pseudomonas aeruginosa, Treponema pallidum* and *Xylella fastidiosa*.

22. The method of claim 1 or claim 6, wherein the coaX gene is a coaX gene from a bacterium selected from the group consisting of *Aquifex aeolicus, Bacillus anthracis, Bacillus halodurans, Bacillus stearothermophilus, Bacillus subtilis, Caulobacter crescentus, Chlorobium tepidum, Clostridium acetobutylicum, Dehalococcoides ethenogenes, Deinococcus radiodurans, Desulfovibrio vulgaris, Geobacter sulfurreducens, Pseudomonas syringae, Pseudomonas putida, Rhodobacter capsulatus, Thiobacillus ferrooxidans, Streptomyces coelicolor, Synechocystis sp., Thermotoga maritima, Bordetella pertussis, Borrelia burgdorferi, Campylobacter jejuni, Clostridium difficile, Helicobacter pylori, Neisseria meningitidis, Neisseria gonorrhoeae, Porphyromonas gingivalis, Pseudomonas aeruginosa, Treponema pallidum, Xylella fastidiosa* and *Mycobacterium tuberculosis*.

* * * * *

SEQUENCE LISTING

<160> NUMBER OF SEQ ID NOS: 87

<210> SEQ ID NO 1
<211> LENGTH: 777
<212> TYPE: DNA
<213> ORGANISM: Bacillus subtilis
<220> FEATURE:
<221> NAME/KEY: CDS
<222> LOCATION: (1)..(774)

<400> SEQUENCE: 1

| | | | | | | | | | | | | | | | | |
|---|---|---|---|---|---|---|---|---|---|---|---|---|---|---|---|---|
| ttg | tta | ctg | gtt | atc | gat | gtg | ggg | aac | acc | aat | act | gta | ctt | ggt | gta | 48 |
| Leu | Leu | Leu | Val | Ile | Asp | Val | Gly | Asn | Thr | Asn | Thr | Val | Leu | Gly | Val | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tat | cat | gat | gga | aaa | tta | gaa | tat | cac | tgg | cgt | ata | gaa | aca | agc | agg | 96 |
| Tyr | His | Asp | Gly | Lys | Leu | Glu | Tyr | His | Trp | Arg | Ile | Glu | Thr | Ser | Arg | |
| | | | 20 | | | | | 25 | | | | | 30 | | | |

| | | | | | | | | | | | | | | | | |
|---|---|---|---|---|---|---|---|---|---|---|---|---|---|---|---|---|
| cat | aaa | aca | gaa | gat | gag | ttt | ggg | atg | att | ttg | cgc | tcc | tta | ttt | gat | 144 |
| His | Lys | Thr | Glu | Asp | Glu | Phe | Gly | Met | Ile | Leu | Arg | Ser | Leu | Phe | Asp | |
| | | 35 | | | | | 40 | | | | | 45 | | | | |

| | | | | | | | | | | | | | | | | |
|---|---|---|---|---|---|---|---|---|---|---|---|---|---|---|---|---|
| cac | tcc | ggg | ctt | atg | ttt | gaa | cag | ata | gat | ggc | att | att | att | tcg | tca | 192 |
| His | Ser | Gly | Leu | Met | Phe | Glu | Gln | Ile | Asp | Gly | Ile | Ile | Ile | Ser | Ser | |
| | 50 | | | | | 55 | | | | | 60 | | | | | |

| | | | | | | | | | | | | | | | | |
|---|---|---|---|---|---|---|---|---|---|---|---|---|---|---|---|---|
| gta | gtg | ccg | cca | atc | atg | ttt | gcg | tta | gaa | aga | atg | tgc | aca | aaa | tac | 240 |
| Val | Val | Pro | Pro | Ile | Met | Phe | Ala | Leu | Glu | Arg | Met | Cys | Thr | Lys | Tyr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ttt | cat | atc | gag | cct | caa | att | gtt | ggt | cca | ggt | atg | aaa | acc | ggt | tta | 288 |
| Phe | His | Ile | Glu | Pro | Gln | Ile | Val | Gly | Pro | Gly | Met | Lys | Thr | Gly | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| aat | ata | aaa | tat | gac | aat | ccg | aaa | gaa | gta | ggg | gca | gac | aga | atc | gta | 336 |
| Asn | Ile | Lys | Tyr | Asp | Asn | Pro | Lys | Glu | Val | Gly | Ala | Asp | Arg | Ile | Val | |
| | | | 100 | | | | | 105 | | | | | 110 | | | |

| | | | | | | | | | | | | | | | | |
|---|---|---|---|---|---|---|---|---|---|---|---|---|---|---|---|---|
| aat | gct | gtc | gct | gcg | ata | cac | ttg | tac | ggc | aat | cca | tta | att | gtt | gtc | 384 |
| Asn | Ala | Val | Ala | Ala | Ile | His | Leu | Tyr | Gly | Asn | Pro | Leu | Ile | Val | Val | |
| | | | 115 | | | | | 120 | | | | | 125 | | | |

| | | | | | | | | | | | | | | | | |
|---|---|---|---|---|---|---|---|---|---|---|---|---|---|---|---|---|
| gat | ttc | gga | acc | gcc | aca | acg | tac | tgc | tat | att | gat | gaa | aac | aaa | caa | 432 |
| Asp | Phe | Gly | Thr | Ala | Thr | Thr | Tyr | Cys | Tyr | Ile | Asp | Glu | Asn | Lys | Gln | |
| | | 130 | | | | | 135 | | | | | 140 | | | | |

| | | | | | | | | | | | | | | | | |
|---|---|---|---|---|---|---|---|---|---|---|---|---|---|---|---|---|
| tac | atg | ggc | ggg | gcg | att | gcc | cct | ggg | att | aca | att | tcg | aca | gag | gcg | 480 |
| Tyr | Met | Gly | Gly | Ala | Ile | Ala | Pro | Gly | Ile | Thr | Ile | Ser | Thr | Glu | Ala | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ctt | tac | tcg | cgt | gca | gca | aag | ctt | cct | cgt | atc | gaa | atc | acc | cgg | ccc | 528 |
| Leu | Tyr | Ser | Arg | Ala | Ala | Lys | Leu | Pro | Arg | Ile | Glu | Ile | Thr | Arg | Pro | |
| | | | 165 | | | | | 170 | | | | | 175 | | | |

| | | | | | | | | | | | | | | | | |
|---|---|---|---|---|---|---|---|---|---|---|---|---|---|---|---|---|
| gac | aat | att | atc | gga | aaa | aac | act | gtt | agc | gcg | atg | caa | tct | gga | att | 576 |
| Asp | Asn | Ile | Ile | Gly | Lys | Asn | Thr | Val | Ser | Ala | Met | Gln | Ser | Gly | Ile | |
| | | | 180 | | | | | 185 | | | | | 190 | | | |

| | | | | | | | | | | | | | | | | |
|---|---|---|---|---|---|---|---|---|---|---|---|---|---|---|---|---|
| tta | ttt | ggc | tat | gtc | ggc | caa | gtg | gaa | gga | atc | gtt | aag | cga | atg | aaa | 624 |
| Leu | Phe | Gly | Tyr | Val | Gly | Gln | Val | Glu | Gly | Ile | Val | Lys | Arg | Met | Lys | |
| | | 195 | | | | | 200 | | | | | 205 | | | | |

| | | | | | | | | | | | | | | | | |
|---|---|---|---|---|---|---|---|---|---|---|---|---|---|---|---|---|
| tgg | cag | gca | aaa | cag | gac | ctc | aag | gtc | att | gcg | aca | gga | ggc | ctg | gcg | 672 |
| Trp | Gln | Ala | Lys | Gln | Asp | Leu | Lys | Val | Ile | Ala | Thr | Gly | Gly | Leu | Ala | |
| | 210 | | | | | 215 | | | | | 220 | | | | | |

| | | | | | | | | | | | | | | | | |
|---|---|---|---|---|---|---|---|---|---|---|---|---|---|---|---|---|
| ccg | ctc | att | gcg | aac | gaa | tca | gat | tgt | ata | gac | atc | gtt | gat | cca | ttc | 720 |
| Pro | Leu | Ile | Ala | Asn | Glu | Ser | Asp | Cys | Ile | Asp | Ile | Val | Asp | Pro | Phe | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| tta | acc | cta | aaa | ggg | ctg | gaa | ttg | att | tat | gaa | aga | aac | cgc | gta | gga | 768 |
| Leu | Thr | Leu | Lys | Gly | Leu | Glu | Leu | Ile | Tyr | Glu | Arg | Asn | Arg | Val | Gly | |
| | | | 245 | | | | | 250 | | | | | 255 | | | |

```
agt gta tag                                                      777
Ser Val
```

<210> SEQ ID NO 2
<211> LENGTH: 258
<212> TYPE: PRT
<213> ORGANISM: Bacillus subtilis

<400> SEQUENCE: 2

```
Leu Leu Leu Val Ile Asp Val Gly Asn Thr Asn Thr Val Leu Gly Val
1               5                   10                  15

Tyr His Asp Gly Lys Leu Glu Tyr His Trp Arg Ile Glu Thr Ser Arg
            20                  25                  30

His Lys Thr Glu Asp Glu Phe Gly Met Ile Leu Arg Ser Leu Phe Asp
        35                  40                  45

His Ser Gly Leu Met Phe Glu Gln Ile Asp Gly Ile Ile Ser Ser
    50                  55                  60

Val Val Pro Pro Ile Met Phe Ala Leu Glu Arg Met Cys Thr Lys Tyr
65                  70                  75                  80

Phe His Ile Glu Pro Gln Ile Val Gly Pro Gly Met Lys Thr Gly Leu
                85                  90                  95

Asn Ile Lys Tyr Asp Asn Pro Lys Glu Val Gly Ala Asp Arg Ile Val
            100                 105                 110

Asn Ala Val Ala Ala Ile His Leu Tyr Gly Asn Pro Leu Ile Val Val
        115                 120                 125

Asp Phe Gly Thr Ala Thr Thr Tyr Cys Tyr Ile Asp Glu Asn Lys Gln
    130                 135                 140

Tyr Met Gly Gly Ala Ile Ala Pro Gly Ile Thr Ile Ser Thr Glu Ala
145                 150                 155                 160

Leu Tyr Ser Arg Ala Ala Lys Leu Pro Arg Ile Glu Ile Thr Arg Pro
                165                 170                 175

Asp Asn Ile Ile Gly Lys Asn Thr Val Ser Ala Met Gln Ser Gly Ile
            180                 185                 190

Leu Phe Gly Tyr Val Gly Gln Val Glu Gly Ile Val Lys Arg Met Lys
        195                 200                 205

Trp Gln Ala Lys Gln Asp Leu Lys Val Ile Ala Thr Gly Gly Leu Ala
    210                 215                 220

Pro Leu Ile Ala Asn Glu Ser Asp Cys Ile Asp Ile Val Asp Pro Phe
225                 230                 235                 240

Leu Thr Leu Lys Gly Leu Glu Leu Ile Tyr Glu Arg Asn Arg Val Gly
                245                 250                 255

Ser Val
```

<210> SEQ ID NO 3
<211> LENGTH: 250
<212> TYPE: PRT
<213> ORGANISM: Clostridium acetobutylicum

<400> SEQUENCE: 3

```
Asn Lys Arg Ala Ala Phe Met Leu Leu Leu Phe Leu Arg Ser Val Leu
1               5                   10                  15

Lys Val Ile Leu Val Leu Asp Val Gly Asn Thr Asn Ile Val Leu Gly
            20                  25                  30

Ile Tyr Asn Asp Thr Lys Leu Thr Ala Glu Trp Arg Leu Ser Thr Asp
        35                  40                  45

Val Leu Arg Ser Ala Asp Glu Tyr Gly Ile Gln Val Met Asn Leu Phe
```

```
                50                   55                  60
Gln Gln Asp Lys Leu Asp Pro Thr Leu Val Glu Gly Val Ile Ile Ser
 65                  70                  75                  80

Ser Val Val Pro Asn Ile Met Tyr Ser Leu Glu His Met Ile Arg Lys
                 85                  90                  95

Tyr Phe Lys Ile Asn Pro Leu Val Val Gly Pro Gly Ile Lys Thr Gly
                100                 105                 110

Ile Asn Ile Lys Tyr Asp Asn Pro Lys Glu Val Gly Ala Asp Arg Ile
                115                 120                 125

Val Asn Ala Val Ala Ala His Glu Ile Tyr Lys Arg Ser Leu Ile Ile
130                 135                 140

Ile Asp Phe Gly Thr Ala Thr Thr Phe Cys Ala Val Arg Glu Asn Gly
145                 150                 155                 160

Asp Tyr Leu Gly Gly Ala Ile Cys Pro Gly Ile Lys Val Ser Ser Glu
                165                 170                 175

Ala Leu Phe Glu Lys Ala Ala Lys Leu Pro Arg Val Glu Leu Ile Lys
                180                 185                 190

Pro Ala Tyr Ala Ile Cys Lys Asn Thr Ile Ser Ser Ile Gln Ser Gly
                195                 200                 205

Ile Val Tyr Arg Tyr Leu Arg Gln Val Lys Tyr Leu Phe Glu Lys Leu
                210                 215                 220

Lys Glu Asn Leu Pro Asp Gly Arg Arg Thr Arg Thr Ser Leu Val Leu
225                 230                 235                 240

Ala Thr Gly Gly Leu Ala Lys Leu Ile Asn
                245                 250

<210> SEQ ID NO 4
<211> LENGTH: 265
<212> TYPE: PRT
<213> ORGANISM: Streptomyces coelicolor

<400> SEQUENCE: 4

Met Leu Leu Thr Ile Asp Val Gly Asn Thr His Thr Val Leu Gly Leu
 1               5                  10                  15

Phe Asp Gly Glu Asp Ile Val Glu His Trp Arg Ile Ser Thr Asp Ser
                20                  25                  30

Arg Arg Thr Ala Asp Glu Leu Ala Val Leu Leu Gln Gly Leu Met Gly
                35                  40                  45

Met His Pro Leu Leu Gly Asp Glu Leu Gly Asp Gly Ile Asp Gly Ile
 50                  55                  60

Ala Ile Cys Ala Thr Val Pro Ser Val Leu His Glu Leu Arg Glu Val
 65                  70                  75                  80

Thr Arg Arg Tyr Tyr Gly Asp Val Pro Ala Val Leu Val Glu Pro Gly
                85                  90                  95

Val Lys Thr Gly Val Pro Ile Leu Thr Asp His Pro Lys Glu Val Gly
                100                 105                 110

Ala Asp Arg Ile Ile Asn Ala Val Ala Ala Val Glu Leu Tyr Gly Gly
                115                 120                 125

Pro Ala Ile Val Val Asp Phe Gly Thr Ala Thr Thr Phe Asp Ala Val
                130                 135                 140

Ser Ala Arg Gly Glu Tyr Ile Gly Gly Val Ile Ala Pro Gly Ile Glu
145                 150                 155                 160

Ile Ser Val Glu Ala Leu Gly Val Lys Gly Ala Gln Leu Arg Lys Ile
                165                 170                 175
```

```
Glu Val Ala Arg Pro Arg Ser Val Ile Gly Lys Asn Thr Val Glu Ala
                180                 185                 190
Met Gln Ser Gly Ile Val Tyr Gly Phe Ala Gly Gln Val Asp Gly Val
            195                 200                 205
Val Asn Arg Met Ala Arg Glu Leu Ala Asp Pro Asp Val Thr
        210                 215                 220
Val Ile Ala Thr Gly Gly Leu Ala Pro Met Val Leu Gly Glu Ser Ser
225                 230                 235                 240
Val Ile Asp Glu His Glu Pro Trp Leu Thr Leu Met Gly Leu Arg Leu
                245                 250                 255
Val Tyr Glu Arg Asn Val Ser Arg Met
                260                 265

<210> SEQ ID NO 5
<211> LENGTH: 272
<212> TYPE: PRT
<213> ORGANISM: Mycobacterium tuberculosis

<400> SEQUENCE: 5

Met Leu Leu Ala Ile Asp Val Arg Asn Thr His Thr Val Val Gly Leu
1               5                   10                  15
Leu Ser Gly Met Lys Glu His Ala Lys Val Val Gln Gln Trp Arg Ile
                20                  25                  30
Arg Thr Glu Ser Glu Val Thr Ala Asp Glu Leu Ala Leu Thr Ile Asp
            35                  40                  45
Gly Leu Ile Gly Glu Asp Ser Glu Arg Leu Thr Gly Thr Ala Ala Leu
        50                  55                  60
Ser Thr Val Pro Ser Val Leu His Glu Val Arg Ile Met Leu Asp Gln
65                  70                  75                  80
Tyr Trp Pro Ser Val Pro His Val Leu Ile Glu Pro Gly Val Arg Thr
                85                  90                  95
Gly Ile Pro Leu Leu Val Asp Asn Pro Lys Glu Val Gly Ala Asp Arg
            100                 105                 110
Ile Val Asn Cys Leu Ala Ala Tyr Asp Arg Phe Arg Lys Ala Ala Ile
        115                 120                 125
Val Val Asp Phe Gly Ser Ser Ile Cys Val Asp Val Val Ser Ala Lys
130                 135                 140
Gly Glu Phe Leu Gly Gly Ala Ile Ala Pro Gly Val Gln Val Ser Ser
145                 150                 155                 160
Asp Ala Ala Ala Arg Ser Ala Leu Arg Arg Val Glu Leu Ala
                165                 170                 175
Arg Pro Arg Ser Val Val Gly Lys Asn Thr Val Glu Cys Met Gln Ala
            180                 185                 190
Gly Ala Val Phe Gly Phe Ala Gly Leu Val Asp Gly Leu Val Gly Arg
        195                 200                 205
Ile Arg Glu Asp Val Ser Gly Phe Ser Val Asp His Asp Val Ala Ile
        210                 215                 220
Val Ala Thr Gly His Thr Ala Pro Leu Leu Pro Glu Leu His Thr
225                 230                 235                 240
Val Asp His Tyr Asp Gln His Leu Thr Leu Gln Gly Leu Arg Leu Val
                245                 250                 255
Phe Glu Arg Asn Leu Glu Val Gln Arg Gly Arg Leu Lys Thr Ala Arg
                260                 265                 270

<210> SEQ ID NO 6
```

-continued

<211> LENGTH: 258
<212> TYPE: PRT
<213> ORGANISM: Rhodobacter capsulatus

<400> SEQUENCE: 6

Met Leu Leu Cys Ile Asp Cys Gly Asn Thr Asn Thr Val Phe Ser Val
1               5                   10                  15

Trp Asp Gly Thr Asp Phe Ala Ala Thr Trp Arg Ile Ala Thr Asp His
            20                  25                  30

Arg Arg Thr Ala Asp Glu Tyr Phe Val Trp Leu Asn Thr Leu Met Gln
        35                  40                  45

Leu Lys Gly Leu Gln Gly Arg Ile Ser Glu Ala Ile Ile Ser Ser Thr
50                  55                  60

Ala Pro Arg Val Val Phe Asn Leu Arg Val Leu Cys Asn Arg Tyr Phe
65                  70                  75                  80

Asp Cys Arg Pro Tyr Val Val Gly Lys Pro Gly Cys Glu Leu Pro Val
                85                  90                  95

Ala Pro Arg Val Asp Pro Gly Thr Thr Val Gly Pro Asp Arg Leu Val
            100                 105                 110

Asn Thr Val Ala Gly Tyr Asp Arg His Gly Gly Asp Leu Ile Val Val
        115                 120                 125

Asp Phe Gly Thr Ala Thr Thr Phe Asp Val Val Ala Pro Asp Gly Ala
130                 135                 140

Tyr Ile Gly Gly Val Ile Ala Pro Gly Val Asn Leu Ser Leu Glu Ala
145                 150                 155                 160

Leu His Met Ala Ala Ala Leu Pro His Val Asp Val Thr Lys Pro
                165                 170                 175

Gln Gly Val Ile Gly Thr Asn Thr Val Ala Cys Ile Gln Ser Gly Val
            180                 185                 190

Tyr Trp Gly Tyr Ile Gly Leu Val Glu Gly Ile Val Arg Gln Ile Arg
        195                 200                 205

Met Glu Arg Asp Arg Pro Met Lys Val Ile Ala Thr Gly Gly Leu Ala
210                 215                 220

Ser Leu Phe Asp Leu Gly Phe Asp Leu Phe Asp Lys Val Glu Asp Asp
225                 230                 235                 240

Leu Thr Met His Gly Leu Arg Leu Ile Phe Asp Tyr Asn Lys Gly Leu
                245                 250                 255

Gly Ala

<210> SEQ ID NO 7
<211> LENGTH: 255
<212> TYPE: PRT
<213> ORGANISM: Geobacter sulfurreducens

<400> SEQUENCE: 7

Met Leu Leu Val Ile Asp Val Gly Asn Thr Asn Ile Val Leu Gly Ile
1               5                   10                  15

Tyr Asp Gly Glu Arg Leu Val Arg Asp Trp Arg Val Ser Thr Asp Lys
            20                  25                  30

Ala Arg Thr Thr Asp Glu Tyr Gly Ile Leu Ile Asn Glu Leu Phe Arg
        35                  40                  45

Leu Ala Gly Leu Gly Leu Asp Gln Ile Arg Ala Val Ile Ile Ser Ser
50                  55                  60

Val Val Pro Pro Leu Thr Gly Val Leu Glu Arg Leu Ser Leu Gly Tyr
65                  70                  75                  80

```
Phe Gly Met Arg Pro Leu Val Val Gly Pro Gly Ile Lys Thr Gly Met
                85                  90                  95

Pro Ile Gln Tyr Asp Asn Pro Arg Glu Val Gly Ala Asp Arg Ile Val
            100                 105                 110

Asn Ala Val Ala Gly Tyr Glu Lys Tyr Arg Thr Ser Leu Ile Ile Val
        115                 120                 125

Asp Phe Gly Thr Ala Thr Thr Phe Asp Tyr Val Asn Arg Lys Gly Glu
    130                 135                 140

Tyr Cys Gly Gly Ala Ile Ala Pro Gly Leu Val Ile Ser Thr Glu Ala
145                 150                 155                 160

Leu Phe Gln Arg Ala Ser Lys Leu Pro Arg Val Asp Ile Ile Arg Pro
                165                 170                 175

Ser Ala Ile Ile Ala Arg Asn Thr Val Asn Ser Met Gln Ala Gly Ile
            180                 185                 190

Tyr Tyr Gly Tyr Val Gly Leu Val Asp Glu Ile Val Thr Arg Met Lys
        195                 200                 205

Ala Glu Ser Lys Asp Ala Pro Arg Val Ile Ala Thr Gly Gly Leu Ala
    210                 215                 220

Ser Leu Ile Ala Pro Glu Ser Lys Thr Ile Glu Ala Val Glu Glu Tyr
225                 230                 235                 240

Leu Thr Leu Glu Gly Leu Arg Ile Leu Tyr Glu Arg Asn Arg Glu
                245                 250                 255

<210> SEQ ID NO 8
<211> LENGTH: 262
<212> TYPE: PRT
<213> ORGANISM: Deinococcus radiodurans

<400> SEQUENCE: 8

Met Pro Ala Phe Pro Leu Leu Ala Val Asp Ile Gly Asn Thr Thr Thr
1               5                   10                  15

Val Leu Gly Leu Ala Asp Ala Ser Gly Ala Leu Thr His Thr Trp Arg
                20                  25                  30

Ile Arg Thr Asn Arg Glu Met Leu Pro Asp Asp Leu Ala Leu Gln Leu
            35                  40                  45

His Gly Leu Phe Thr Leu Ala Gly Ala Pro Ile Pro Arg Ala Ala Val
        50                  55                  60

Leu Ser Ser Val Ala Pro Pro Val Gly Glu Asn Tyr Ala Leu Ala Leu
65                  70                  75                  80

Lys Arg His Phe Met Ile Asp Ala Phe Ala Val Ser Ala Glu Asn Leu
                85                  90                  95

Pro Asp Val Thr Val Glu Leu Asp Thr Pro Gly Ser Val Gly Ala Asp
            100                 105                 110

Arg Leu Cys Asn Leu Phe Gly Ala Glu Lys Tyr Leu Gly Gly Leu Asp
        115                 120                 125

Tyr Ala Val Val Val Asp Phe Gly Thr Ser Thr Asn Phe Asp Val Val
    130                 135                 140

Gly Arg Gly Arg Arg Phe Leu Gly Gly Ile Leu Ala Thr Gly Ala Gln
145                 150                 155                 160

Val Ser Ala Asp Ala Leu Phe Ala Arg Ala Lys Leu Pro Arg Ile
                165                 170                 175

Thr Leu Gln Ala Pro Glu Thr Ala Ile Gly Lys Asn Thr Val His Ala
            180                 185                 190

Leu Gln Ser Gly Leu Val Phe Gly Tyr Ala Glu Met Val Asp Gly Leu
        195                 200                 205
```

Leu Arg Arg Ile Arg Ala Glu Leu Pro Gly Glu Ala Val Ala Val Ala
    210                 215                 220

Thr Gly Gly Phe Ser Arg Thr Val Gln Gly Ile Cys Gln Glu Ile Asp
225                 230                 235                 240

Tyr Tyr Asp Glu Thr Leu Thr Leu Arg Gly Leu Val Glu Leu Trp Ala
                245                 250                 255

Ser Arg Ser Glu Val Arg
            260

<210> SEQ ID NO 9
<211> LENGTH: 246
<212> TYPE: PRT
<213> ORGANISM: Thermotoga maritima

<400> SEQUENCE: 9

Met Tyr Leu Leu Val Asp Val Gly Asn Thr His Ser Val Phe Ser Ile
1               5                   10                  15

Thr Glu Asp Gly Lys Thr Phe Arg Arg Trp Arg Leu Ser Thr Gly Val
            20                  25                  30

Phe Gln Thr Glu Asp Glu Leu Phe Ser His Leu His Pro Leu Leu Gly
        35                  40                  45

Asp Ala Met Arg Glu Ile Lys Gly Ile Gly Val Ala Ser Val Val Pro
    50                  55                  60

Thr Gln Asn Thr Val Ile Glu Arg Phe Ser Gln Lys Tyr Phe His Ile
65                  70                  75                  80

Ser Pro Ile Trp Val Lys Ala Lys Asn Gly Cys Val Lys Trp Asn Val
                85                  90                  95

Lys Asn Pro Ser Glu Val Gly Ala Asp Arg Val Ala Asn Val Val Ala
            100                 105                 110

Phe Val Lys Glu Tyr Gly Lys Asn Gly Ile Ile Ile Asp Met Gly Thr
        115                 120                 125

Ala Thr Thr Val Asp Leu Val Val Asn Gly Ser Tyr Glu Gly Gly Ala
    130                 135                 140

Ile Leu Pro Gly Phe Phe Met Met Val His Ser Leu Phe Arg Gly Thr
145                 150                 155                 160

Ala Lys Leu Pro Leu Val Glu Val Lys Pro Ala Asp Phe Val Val Gly
                165                 170                 175

Lys Asp Thr Glu Glu Asn Ile Arg Leu Gly Val Val Asn Gly Ser Val
            180                 185                 190

Tyr Ala Leu Glu Gly Ile Ile Gly Arg Ile Lys Glu Val Tyr Gly Asp
        195                 200                 205

Leu Pro Val Val Leu Thr Gly Gly Gln Ser Lys Ile Val Lys Asp Met
    210                 215                 220

Ile Lys His Glu Ile Phe Asp Glu Asp Leu Thr Ile Lys Gly Val Tyr
225                 230                 235                 240

His Phe Cys Phe Gly Asp
                245

<210> SEQ ID NO 10
<211> LENGTH: 273
<212> TYPE: PRT
<213> ORGANISM: Treponema pallidum

<400> SEQUENCE: 10

Met Leu Leu Ile Asp Val Gly Asn Ser His Val Val Phe Gly Ile Gln
1               5                   10                  15

-continued

```
Gly Glu Asn Gly Gly Arg Val Cys Val Arg Glu Leu Phe Arg Leu Ala
            20                  25                  30

Pro Asp Ala Arg Lys Thr Gln Asp Glu Tyr Ser Leu Leu Ile His Ala
        35                  40                  45

Leu Cys Glu Arg Ala Gly Val Gly Arg Ala Ser Leu Arg Asp Ala Phe
    50                  55                  60

Ile Ser Ser Val Val Pro Val Leu Thr Lys Thr Ile Ala Asp Ala Val
65                  70                  75                  80

Ala Gln Ile Ser Gly Val Gln Pro Val Val Phe Gly Pro Trp Ala Tyr
                85                  90                  95

Glu His Leu Pro Val Arg Ile Pro Glu Pro Val Arg Ala Glu Ile Gly
            100                 105                 110

Thr Asp Leu Val Ala Asn Ala Val Ala Ala Tyr Val His Phe Arg Ser
        115                 120                 125

Ala Cys Val Val Val Asp Cys Gly Thr Ala Leu Thr Phe Thr Ala Val
    130                 135                 140

Asp Gly Thr Gly Leu Ile Gln Gly Val Ala Ile Ala Pro Gly Leu Arg
145                 150                 155                 160

Thr Ala Val Gln Ser Leu His Thr Gly Thr Ala Gln Leu Pro Leu Val
                165                 170                 175

Pro Leu Ala Leu Pro Asp Ser Val Leu Gly Lys Asp Thr Thr His Ala
            180                 185                 190

Val Gln Ala Gly Val Val Arg Gly Thr Leu Phe Val Ile Arg Ala Met
        195                 200                 205

Ile Ala Gln Cys Gln Lys Glu Leu Gly Cys Arg Cys Ala Ala Val Ile
    210                 215                 220

Thr Gly Gly Leu Ser Arg Leu Phe Ser Ser Glu Val Asp Phe Pro Pro
225                 230                 235                 240

Ile Asp Ala Gln Leu Thr Leu Ser Gly Leu Ala His Ile Ala Arg Leu
                245                 250                 255

Val Pro Thr Ser Leu Leu Pro Pro Ala Thr Val Ser Gly Ser Ser Gly
            260                 265                 270

Asn

<210> SEQ ID NO 11
<211> LENGTH: 262
<212> TYPE: PRT
<213> ORGANISM: Borrelia burgdorferi

<400> SEQUENCE: 11

Met Asn Lys Pro Leu Leu Ser Glu Leu Ile Ile Asp Ile Gly Asn Thr
1               5                   10                  15

Ser Ile Ala Phe Ala Leu Phe Lys Asp Asn Gln Val Asn Leu Phe Ile
            20                  25                  30

Lys Met Lys Thr Asn Leu Met Leu Arg Tyr Asp Glu Val Tyr Ser Phe
        35                  40                  45

Phe Glu Glu Asn Phe Asp Phe Asn Val Asn Lys Val Phe Ile Ser Ser
    50                  55                  60

Val Val Pro Ile Leu Asn Glu Thr Phe Lys Asn Val Ile Phe Ser Phe
65                  70                  75                  80

Phe Lys Ile Lys Pro Leu Phe Ile Gly Phe Asp Leu Asn Tyr Asp Leu
                85                  90                  95

Thr Phe Asn Pro Tyr Lys Ser Asp Lys Phe Leu Leu Gly Ser Asp Val
            100                 105                 110
```

```
Phe Ala Asn Leu Val Ala Ala Ile Glu Asn Tyr Ser Phe Glu Asn Val
            115                 120                 125

Leu Val Val Asp Leu Gly Thr Ala Cys Thr Ile Phe Ala Val Ser Arg
    130                 135                 140

Gln Asp Gly Ile Leu Gly Gly Ile Ile Asn Ser Gly Pro Leu Ile Asn
145                 150                 155                 160

Phe Asn Ser Leu Leu Asp Asn Ala Tyr Leu Ile Lys Lys Phe Pro Ile
                165                 170                 175

Ser Thr Pro Asn Asn Leu Leu Glu Arg Thr Thr Ser Gly Ser Val Asn
            180                 185                 190

Ser Gly Leu Phe Tyr Gln Tyr Lys Tyr Leu Ile Glu Gly Val Tyr Arg
    195                 200                 205

Asp Ile Lys Gln Met Tyr Lys Lys Phe Asn Leu Ile Ile Thr Gly
            210                 215                 220

Gly Asn Ala Asp Leu Ile Leu Ser Leu Ile Glu Ile Glu Phe Ile Phe
225                 230                 235                 240

Asn Ile His Leu Thr Val Glu Gly Val Arg Ile Leu Gly Asn Ser Ile
                245                 250                 255

Asp Phe Lys Phe Val Asn
            260

<210> SEQ ID NO 12
<211> LENGTH: 229
<212> TYPE: PRT
<213> ORGANISM: Aquifex aeolicus

<400> SEQUENCE: 12

Met Arg Phe Leu Thr Val Asp Val Gly Asn Ser Ser Val Asp Ile Ala
1               5                   10                  15

Leu Trp Glu Gly Lys Lys Val Lys Asp Phe Leu Lys Leu Ser His Glu
            20                  25                  30

Glu Phe Leu Lys Glu Glu Phe Pro Lys Leu Lys Ala Leu Gly Ile Ser
        35                  40                  45

Val Lys Gln Ser Phe Ser Glu Lys Val Arg Gly Lys Ile Pro Lys Ile
    50                  55                  60

Lys Phe Leu Lys Lys Glu Asn Phe Pro Ile Gln Val Asp Tyr Lys Thr
65                  70                  75                  80

Pro Glu Thr Leu Gly Thr Asp Arg Val Ala Leu Ala Tyr Ser Ala Lys
                85                  90                  95

Lys Phe Tyr Gly Lys Asn Val Val Ile Ser Ala Gly Thr Ala Leu
            100                 105                 110

Val Ile Asp Leu Val Leu Glu Gly Lys Phe Lys Gly Gly Phe Ile Thr
        115                 120                 125

Leu Gly Leu Gly Lys Lys Leu Lys Ile Leu Ser Asp Leu Ala Glu Gly
    130                 135                 140

Ile Pro Glu Phe Phe Pro Glu Glu Val Glu Ile Phe Leu Gly Arg Ser
145                 150                 155                 160

Thr Arg Glu Cys Val Leu Gly Gly Ala Tyr Arg Glu Ser Thr Glu Phe
                165                 170                 175

Ile Lys Ser Thr Leu Lys Leu Trp Arg Lys Val Phe Lys Arg Lys Phe
            180                 185                 190

Lys Val Val Ile Thr Gly Gly Glu Gly Lys Tyr Phe Ser Lys Phe Gly
        195                 200                 205

Ile Tyr Asp Pro Leu Leu Val His Arg Gly Met Arg Asn Leu Leu Tyr
```

```
                    210                 215                 220
Leu Tyr His Arg Ile
225

<210> SEQ ID NO 13
<211> LENGTH: 257
<212> TYPE: PRT
<213> ORGANISM: Synechocystis sp.

<400> SEQUENCE: 13

Met Glu Thr Ser Lys Pro Gly Cys Gly Leu Ala Leu Asp Asn Asp Lys
1               5                   10                  15

Gln Lys Pro Trp Leu Gly Leu Met Ile Gly Asn Ser Arg Leu His Trp
            20                  25                  30

Ala Tyr Cys Ser Gly Asn Ala Pro Leu Gln Thr Trp Val Thr Asp Tyr
        35                  40                  45

Asn Pro Lys Ser Ala Gln Leu Pro Val Leu Gly Lys Val Pro Leu
    50                  55                  60

Met Leu Ala Ser Val Val Pro Glu Gln Thr Glu Val Trp Arg Val Tyr
65                  70                  75                  80

Gln Pro Lys Ile Leu Thr Leu Lys Asn Leu Pro Val Asn Leu Tyr
                85                  90                  95

Pro Ser Phe Gly Ile Asp Arg Ala Leu Ala Gly Leu Gly Thr Gly Leu
            100                 105                 110

Thr Tyr Gly Phe Pro Cys Leu Val Val Asp Gly Gly Thr Ala Leu Thr
        115                 120                 125

Ile Thr Gly Phe Asp Gln Asp Lys Lys Leu Val Gly Gly Ala Ile Leu
    130                 135                 140

Pro Gly Leu Gly Leu Gln Leu Ala Thr Leu Gly Asp Arg Leu Ala Ala
145                 150                 155                 160

Leu Pro Lys Leu Glu Met Asp Gln Leu Thr Glu Leu Pro Asp Arg Trp
                165                 170                 175

Ala Leu Asp Thr Pro Ser Ala Ile Phe Ser Gly Val Val Tyr Gly Val
            180                 185                 190

Leu Gly Ala Leu Gln Ser Tyr Leu Gln Asp Trp Gln Lys Leu Phe Pro
        195                 200                 205

Gly Ala Ala Met Val Ile Thr Gly Gly Asp Gly Lys Ile Leu His Gly
    210                 215                 220

Phe Leu Lys Glu His Ser Pro Asn Leu Ser Val Ala Trp Asp Asn
225                 230                 235                 240

Leu Ile Phe Leu Gly Met Ala Ala Ile His His Gly Asp Arg Pro Ile
                245                 250                 255

Cys

<210> SEQ ID NO 14
<211> LENGTH: 223
<212> TYPE: PRT
<213> ORGANISM: Helicobacter pylori

<400> SEQUENCE: 14

Met Pro Ala Arg Gln Ser Phe Thr Asp Leu Lys Asn Leu Val Leu Cys
1               5                   10                  15

Asp Ile Gly Asn Thr Arg Ile His Phe Ala Gln Asn Tyr Gln Leu Phe
            20                  25                  30

Ser Ser Ala Lys Glu Asp Leu Lys Arg Leu Gly Ile Gln Lys Glu Ile
        35                  40                  45
```

Phe Tyr Ile Ser Val Asn Glu Glu Asn Glu Lys Ala Leu Leu Asn Cys
    50                  55                  60

Tyr Pro Asn Ala Lys Asn Ile Ala Gly Phe Phe His Leu Glu Thr Asp
65                  70                  75                  80

Tyr Val Gly Leu Gly Ile Asp Arg Gln Met Ala Cys Leu Ala Val Asn
                85                  90                  95

Asn Gly Val Val Val Asp Ala Gly Ser Ala Ile Thr Ile Asp Leu Ile
            100                 105                 110

Lys Glu Gly Lys His Leu Gly Gly Cys Ile Leu Pro Gly Leu Ala Gln
        115                 120                 125

Tyr Ile His Ala Tyr Lys Lys Ser Ala Lys Ile Leu Glu Gln Pro Phe
    130                 135                 140

Lys Ala Leu Asp Ser Leu Glu Val Leu Pro Lys Ser Thr Arg Asp Ala
145                 150                 155                 160

Val Asn Tyr Gly Met Val Leu Ser Val Ile Ala Cys Ile Gln His Leu
                165                 170                 175

Ala Lys Asn Gln Lys Ile Tyr Leu Cys Gly Gly Asp Ala Lys Tyr Leu
            180                 185                 190

Ser Ala Phe Leu Pro His Ser Val Cys Lys Glu Arg Leu Val Phe Asp
        195                 200                 205

Gly Met Glu Ile Ala Leu Lys Lys Ala Gly Ile Leu Glu Cys Lys
    210                 215                 220

<210> SEQ ID NO 15
<211> LENGTH: 267
<212> TYPE: PRT
<213> ORGANISM: Bordetella pertussis

<400> SEQUENCE: 15

Met Ile Ile Leu Ile Asp Ser Gly Asn Ser Arg Leu Lys Val Gly Trp
1               5                   10                  15

Phe Asp Pro Asp Ala Pro Gln Ala Ala Arg Glu Pro Ala Pro Val Ala
                20                  25                  30

Phe Asp Asn Leu Asp Leu Asp Ala Leu Gly Arg Trp Leu Ala Thr Leu
            35                  40                  45

Pro Arg Arg Pro Gln Arg Ala Leu Gly Val Asn Val Ala Gly Leu Ala
    50                  55                  60

Arg Gly Glu Ala Ile Ala Ala Thr Leu Arg Ala Gly Cys Asp Ile
65                  70                  75                  80

Arg Trp Leu Arg Ala Gln Pro Leu Ala Met Gly Leu Arg Asn Gly Tyr
                85                  90                  95

Arg Asn Pro Asp Gln Leu Gly Ala Asp Arg Trp Ala Cys Met Val Gly
            100                 105                 110

Val Leu Ala Arg Gln Pro Ser Val His Pro Pro Leu Leu Val Ala Ser
        115                 120                 125

Phe Gly Thr Ala Thr Thr Leu Asp Thr Ile Gly Pro Asp Asn Val Phe
    130                 135                 140

Pro Gly Gly Leu Ile Leu Pro Gly Pro Ala Met Met Arg Gly Ala Leu
145                 150                 155                 160

Ala Tyr Gly Thr Ala His Leu Pro Leu Ala Asp Gly Leu Val Ala Asp
                165                 170                 175

Tyr Pro Ile Asp Thr His Gln Ala Ile Ala Ser Gly Ile Ala Ala Ala
            180                 185                 190

Gln Ala Gly Ala Ile Val Arg Gln Trp Leu Ala Gly Arg Gln Arg Tyr

```
                195                 200                 205
Gly Gln Ala Pro Glu Ile Tyr Val Ala Gly Gly Trp Pro Glu Val
    210                 215                 220

Arg Gln Glu Ala Glu Arg Leu Leu Ala Val Thr Gly Ala Ala Phe Gly
225                 230                 235                 240

Ala Thr Pro Gln Pro Thr Tyr Leu Asp Ser Pro Val Leu Asp Gly Leu
                245                 250                 255

Ala Ala Leu Ala Ala Gln Gly Ala Pro Thr Ala
            260                 265

<210> SEQ ID NO 16
<211> LENGTH: 702
<212> TYPE: DNA
<213> ORGANISM: Bacillus subtilis
<220> FEATURE:
<221> NAME/KEY: CDS
<222> LOCATION: (1)..(699)

<400> SEQUENCE: 16
```

| | | | | | | | | | | | | | | | | |
|---|---|---|---|---|---|---|---|---|---|---|---|---|---|---|---|---|
| ttg | tta | ctg | gtt | atc | gat | gtg | ggg | aac | acc | aat | act | gta | ctt | ggt | gta | 48 |
| Leu | Leu | Leu | Val | Ile | Asp | Val | Gly | Asn | Thr | Asn | Thr | Val | Leu | Gly | Val | |
| 1 | | | | 5 | | | | | 10 | | | | | 15 | | |
| tat | cat | gat | gga | aaa | tta | gaa | tat | cac | tgg | cgt | ata | gaa | aca | agc | agg | 96 |
| Tyr | His | Asp | Gly | Lys | Leu | Glu | Tyr | His | Trp | Arg | Ile | Glu | Thr | Ser | Arg | |
| | | | 20 | | | | | 25 | | | | | 30 | | | |
| cat | aaa | aca | gaa | gat | gag | ttt | ggg | atg | att | ttg | cgc | tcc | tta | ttt | gat | 144 |
| His | Lys | Thr | Glu | Asp | Glu | Phe | Gly | Met | Ile | Leu | Arg | Ser | Leu | Phe | Asp | |
| | | 35 | | | | | 40 | | | | | 45 | | | | |
| cac | tcc | ggg | ctt | atg | ttt | gaa | cag | ata | gat | ggc | att | att | att | tcg | tca | 192 |
| His | Ser | Gly | Leu | Met | Phe | Glu | Gln | Ile | Asp | Gly | Ile | Ile | Ile | Ser | Ser | |
| | 50 | | | | | 55 | | | | | 60 | | | | | |
| gta | gtg | ccg | cca | atc | atg | ttt | gcg | tta | gaa | aga | atg | tgc | aca | aaa | tac | 240 |
| Val | Val | Pro | Pro | Ile | Met | Phe | Ala | Leu | Glu | Arg | Met | Cys | Thr | Lys | Tyr | |
| 65 | | | | | 70 | | | | | 75 | | | | | 80 | |
| ttt | cat | atc | gag | cct | caa | att | gtt | ggt | cca | ggt | atg | aaa | acc | ggt | tta | 288 |
| Phe | His | Ile | Glu | Pro | Gln | Ile | Val | Gly | Pro | Gly | Met | Lys | Thr | Gly | Leu | |
| | | | | 85 | | | | | 90 | | | | | 95 | | |
| aat | ata | aaa | tat | gac | aat | ccg | aaa | gaa | gta | ggg | gca | gac | aga | atc | gta | 336 |
| Asn | Ile | Lys | Tyr | Asp | Asn | Pro | Lys | Glu | Val | Gly | Ala | Asp | Arg | Ile | Val | |
| | | | 100 | | | | | 105 | | | | | 110 | | | |
| aat | gct | gtc | gct | gcg | ata | cac | ttg | tac | ggc | aat | cca | tta | att | gtt | gtc | 384 |
| Asn | Ala | Val | Ala | Ala | Ile | His | Leu | Tyr | Gly | Asn | Pro | Leu | Ile | Val | Val | |
| | | 115 | | | | | 120 | | | | | 125 | | | | |
| gat | ttc | gga | acc | gcc | aca | acg | tac | tgc | tat | att | gat | gaa | aac | aaa | caa | 432 |
| Asp | Phe | Gly | Thr | Ala | Thr | Thr | Tyr | Cys | Tyr | Ile | Asp | Glu | Asn | Lys | Gln | |
| | 130 | | | | | 135 | | | | | 140 | | | | | |
| tac | atg | ggc | ggg | gcg | att | gcc | cct | ggg | att | aca | att | tcg | aca | gag | gcg | 480 |
| Tyr | Met | Gly | Gly | Ala | Ile | Ala | Pro | Gly | Ile | Thr | Ile | Ser | Thr | Glu | Ala | |
| 145 | | | | | 150 | | | | | 155 | | | | | 160 | |
| ctt | tac | tcg | cgt | gca | gca | aag | ctt | cct | cgt | atc | gaa | atc | acc | cgg | ccc | 528 |
| Leu | Tyr | Ser | Arg | Ala | Ala | Lys | Leu | Pro | Arg | Ile | Glu | Ile | Thr | Arg | Pro | |
| | | | | 165 | | | | | 170 | | | | | 175 | | |
| gac | aat | att | atc | gga | aaa | aac | act | gtt | agc | gcg | atg | caa | tct | gga | att | 576 |
| Asp | Asn | Ile | Ile | Gly | Lys | Asn | Thr | Val | Ser | Ala | Met | Gln | Ser | Gly | Ile | |
| | | | 180 | | | | | 185 | | | | | 190 | | | |
| tta | ttt | ggc | tat | gtc | ggc | caa | gtg | gaa | gga | atc | gtt | aag | cga | atg | aaa | 624 |
| Leu | Phe | Gly | Tyr | Val | Gly | Gln | Val | Glu | Gly | Ile | Val | Lys | Arg | Met | Lys | |
| | | 195 | | | | | 200 | | | | | 205 | | | | |
| tgg | cag | gca | aaa | cag | gac | cca | agg | tca | ttg | cga | cag | gag | gcc | tgg | cgc | 672 |
| Trp | Gln | Ala | Lys | Gln | Asp | Pro | Arg | Ser | Leu | Arg | Gln | Glu | Ala | Trp | Arg | |

```
                210               215               220
cgc tca ttg cga acg aat cag att gta tag                              702
Arg Ser Leu Arg Thr Asn Gln Ile Val
225                 230

<210> SEQ ID NO 17
<211> LENGTH: 233
<212> TYPE: PRT
<213> ORGANISM: Bacillus subtilis

<400> SEQUENCE: 17

Leu Leu Leu Val Ile Asp Val Gly Asn Thr Asn Thr Val Leu Gly Val
1               5                   10                  15

Tyr His Asp Gly Lys Leu Glu Tyr His Trp Arg Ile Glu Thr Ser Arg
            20                  25                  30

His Lys Thr Glu Asp Glu Phe Gly Met Ile Leu Arg Ser Leu Phe Asp
        35                  40                  45

His Ser Gly Leu Met Phe Glu Gln Ile Asp Gly Ile Ile Ile Ser Ser
    50                  55                  60

Val Val Pro Pro Ile Met Phe Ala Leu Glu Arg Met Cys Thr Lys Tyr
65                  70                  75                  80

Phe His Ile Glu Pro Gln Ile Val Gly Pro Gly Met Lys Thr Gly Leu
                85                  90                  95

Asn Ile Lys Tyr Asp Asn Pro Lys Glu Val Gly Ala Asp Arg Ile Val
            100                 105                 110

Asn Ala Val Ala Ala Ile His Leu Tyr Gly Asn Pro Leu Ile Val Val
        115                 120                 125

Asp Phe Gly Thr Ala Thr Thr Tyr Cys Tyr Ile Asp Glu Asn Lys Gln
    130                 135                 140

Tyr Met Gly Gly Ala Ile Ala Pro Gly Ile Thr Ile Ser Thr Glu Ala
145                 150                 155                 160

Leu Tyr Ser Arg Ala Ala Lys Leu Pro Arg Ile Glu Ile Thr Arg Pro
                165                 170                 175

Asp Asn Ile Ile Gly Lys Asn Thr Val Ser Ala Met Gln Ser Gly Ile
            180                 185                 190

Leu Phe Gly Tyr Val Gly Gln Val Glu Gly Ile Val Lys Arg Met Lys
        195                 200                 205

Trp Gln Ala Lys Gln Asp Pro Arg Ser Leu Arg Gln Glu Ala Trp Arg
    210                 215                 220

Arg Ser Leu Arg Thr Asn Gln Ile Val
225                 230

<210> SEQ ID NO 18
<211> LENGTH: 163
<212> TYPE: DNA
<213> ORGANISM: Artificial Sequence
<220> FEATURE:
<223> OTHER INFORMATION: Description of Artificial Sequence:promoter
      sequence
<220> FEATURE:
<221> NAME/KEY: -35_signal
<222> LOCATION: (113)..(118)
<220> FEATURE:
<221> NAME/KEY: -10_signal
<222> LOCATION: (136)..(141)

<400> SEQUENCE: 18
gcctacctag cttccaagaa agatatccta acagcacaag agcggaaaga tgttttgttc       60
tacatccaga acaacctctg ctaaaattcc tgaaaaattt tgcaaaaagt tgttgacttt     120
```
atctacaagg tgtggtataa taatcttaac aacagcagga cgc      163

<210> SEQ ID NO 19
<211> LENGTH: 194
<212> TYPE: DNA
<213> ORGANISM: Artificial Sequence
<220> FEATURE:
<223> OTHER INFORMATION: Description of Artificial Sequence:promoter
      sequence
<220> FEATURE:
<221> NAME/KEY: -35_signal
<222> LOCATION: (136)..(141)
<220> FEATURE:
<221> NAME/KEY: -10_signal
<222> LOCATION: (159)..(164)

<400> SEQUENCE: 19
gctattgacg acagctatgg ttcactgtcc accaaccaaa actgtgctca gtaccgccaa      60
tatttctccc ttgaggggta caaagaggtg tccctagaag agatccacgc tgtgtaaaaa     120
ttttacaaaa aggtattgac tttccctaca gggtgtgtaa taatttaatt acaggcgggg     180
gcaaccccgc ctgt      194

<210> SEQ ID NO 20
<211> LENGTH: 248
<212> TYPE: PRT
<213> ORGANISM: Pseudomonas aeruginosa

<400> SEQUENCE: 20

Met Ile Leu Glu Leu Asp Cys Gly Asn Ser Leu Ile Lys Trp Arg Val
1               5                   10                  15

Ile Glu Gly Ala Ala Arg Ser Val Ala Gly Gly Leu Ala Glu Ser Asp
            20                  25                  30

Asp Ala Leu Val Glu Gln Leu Thr Ser Gln Gln Ala Leu Pro Val Arg
        35                  40                  45

Ala Cys Arg Leu Val Ser Val Arg Ser Glu Gln Glu Thr Ser Gln Leu
    50                  55                  60

Val Ala Arg Leu Glu Gln Leu Phe Pro Val Ser Ala Leu Val Ala Ser
65                  70                  75                  80

Ser Gly Lys Gln Leu Ala Gly Val Arg Asn Gly Tyr Leu Asp Tyr Gln
                85                  90                  95

Arg Leu Gly Leu Asp Arg Trp Leu Ala Leu Val Ala Ala His His Leu
            100                 105                 110

Ala Lys Lys Ala Cys Leu Val Ile Asp Leu Gly Thr Ala Val Thr Ser
        115                 120                 125

Asp Leu Val Ala Ala Asp Gly Val His Leu Gly Gly Tyr Ile Cys Pro
    130                 135                 140

Gly Met Thr Leu Met Arg Ser Gln Leu Arg Thr His Thr Arg Arg Ile
145                 150                 155                 160

Arg Tyr Asp Asp Ala Glu Ala Arg Arg Ala Leu Ala Ser Leu Gln Pro
                165                 170                 175

Gly Gln Ala Thr Ala Glu Ala Val Glu Arg Gly Cys Leu Leu Met Leu
            180                 185                 190

Arg Gly Phe Val Arg Glu Gln Tyr Ala Met Ala Cys Glu Leu Leu Gly
        195                 200                 205

Pro Asp Cys Glu Ile Phe Leu Thr Gly Gly Asp Ala Glu Leu Val Arg
    210                 215                 220

Asp Glu Leu Ala Gly Ala Arg Ile Met Pro Asp Leu Val Phe Val Gly

```
                225                 230                 235                 240

Leu Ala Leu Ala Cys Pro Ile Glu
                245

<210> SEQ ID NO 21
<211> LENGTH: 209
<212> TYPE: PRT
<213> ORGANISM: Campylobacter jejuni

<400> SEQUENCE: 21

Met Leu Leu Cys Asp Ile Gly Asn Ser Asn Ala Asn Phe Leu Asp Asp
1               5                   10                  15

Asn Lys Tyr Phe Thr Leu Asn Ile Asp Gln Phe Leu Glu Phe Lys Asn
            20                  25                  30

Glu Gln Lys Ile Phe Tyr Ile Asn Val Asn Glu His Leu Lys Glu His
        35                  40                  45

Leu Lys Asn Gln Lys Asn Phe Ile Asn Leu Glu Pro Tyr Phe Leu Phe
    50                  55                  60

Asp Thr Ile Tyr Gln Gly Leu Gly Ile Asp Arg Ile Ala Ala Cys Tyr
65                  70                  75                  80

Thr Ile Glu Asp Gly Val Val Asp Ala Gly Ser Ala Ile Thr Ile
            85                  90                  95

Asp Ile Ile Ser Asn Ser Ile His Leu Gly Gly Phe Ile Leu Pro Gly
        100                 105                 110

Ile Ala Asn Tyr Lys Lys Ile Tyr Ser His Ile Ser Pro Arg Leu Lys
    115                 120                 125

Ser Glu Phe Asn Thr Gln Val Ser Leu Asp Ala Phe Pro Gln Lys Thr
130                 135                 140

Met Asp Ala Leu Ser Tyr Gly Val Phe Lys Gly Ile Tyr Leu Leu Ile
145                 150                 155                 160

Lys Asp Ala Ala Gln Asn Lys Lys Leu Tyr Phe Thr Gly Gly Asp Gly
            165                 170                 175

Gln Phe Leu Ala Asn Tyr Phe Asp His Ala Ile Tyr Asp Lys Leu Leu
        180                 185                 190

Ile Phe Arg Gly Met Lys Lys Ile Ile Lys Glu Asn Pro Asn Leu Leu
    195                 200                 205

Tyr

<210> SEQ ID NO 22
<211> LENGTH: 592
<212> TYPE: PRT
<213> ORGANISM: Neisseria meningitidis

<400> SEQUENCE: 22

Met Thr Val Leu Lys Pro Ser His Trp Arg Val Leu Ala Glu Leu Ala
1               5                   10                  15

Asp Gly Leu Pro Gln His Val Ser Gln Leu Ala Arg Met Ala Asp Met
            20                  25                  30

Lys Pro Gln Gln Leu Asn Gly Phe Trp Gln Met Pro Ala His Ile
        35                  40                  45

Arg Gly Leu Leu Arg Gln His Asp Gly Tyr Trp Arg Leu Val Arg Pro
    50                  55                  60

Leu Ala Val Phe Asp Ala Glu Gly Leu Arg Glu Leu Gly Glu Arg Ser
65                  70                  75                  80

Gly Phe Gln Thr Ala Leu Lys His Glu Cys Ala Ser Ser Asn Asp Glu
            85                  90                  95
```

```
Ile Leu Glu Leu Ala Arg Ile Ala Pro Asp Lys Ala His Lys Thr Ile
            100                 105                 110

Cys Val Thr His Leu Gln Ser Lys Gly Arg Gly Arg Gln Gly Arg Lys
        115                 120                 125

Trp Ser His Arg Leu Gly Glu Cys Leu Met Phe Ser Phe Gly Trp Val
    130                 135                 140

Phe Asp Arg Pro Gln Tyr Glu Leu Gly Ser Leu Ser Pro Val Ala Ala
145                 150                 155                 160

Val Ala Cys Arg Arg Ala Leu Ser Arg Leu Gly Leu Lys Thr Gln Ile
                165                 170                 175

Lys Trp Pro Asn Asp Leu Val Val Gly Arg Asp Lys Leu Gly Gly Ile
            180                 185                 190

Leu Ile Glu Thr Val Arg Thr Gly Gly Lys Thr Val Ala Val Val Gly
        195                 200                 205

Ile Gly Ile Asn Phe Val Leu Pro Lys Glu Val Glu Asn Ala Ala Ser
    210                 215                 220

Val Gln Ser Leu Phe Gln Thr Ala Ser Arg Arg Gly Asn Ala Asp Ala
225                 230                 235                 240

Ala Val Leu Leu Glu Thr Leu Leu Ala Glu Leu Asp Ala Val Leu Leu
                245                 250                 255

Gln Tyr Ala Arg Asp Gly Phe Ala Pro Phe Val Ala Glu Tyr Gln Ala
            260                 265                 270

Ala Asn Arg Asp His Gly Lys Ala Val Leu Leu Arg Asp Gly Glu
        275                 280                 285

Thr Val Phe Glu Gly Thr Val Lys Gly Val Asp Gly Gln Gly Val Leu
    290                 295                 300

His Leu Glu Thr Ala Glu Gly Lys Gln Thr Val Ser Gly Glu Ile
305                 310                 315                 320

Ser Leu Arg Ser Asp Asp Arg Pro Val Ser Val Pro Lys Arg Arg Asp
                325                 330                 335

Ser Glu Arg Phe Leu Leu Leu Asp Gly Gly Asn Ser Arg Leu Lys Trp
            340                 345                 350

Ala Trp Val Glu Asn Gly Thr Phe Ala Thr Val Gly Ser Ala Pro Tyr
        355                 360                 365

Arg Asp Leu Ser Pro Leu Gly Ala Glu Trp Ala Glu Lys Val Asp Gly
    370                 375                 380

Asn Val Arg Ile Val Gly Cys Ala Val Cys Gly Glu Phe Lys Lys Ala
385                 390                 395                 400

Gln Val Gln Glu Gln Leu Ala Arg Lys Ile Glu Trp Leu Pro Ser Ser
                405                 410                 415

Ala Gln Ala Leu Gly Ile Arg Asn His Tyr Arg His Pro Glu Glu His
            420                 425                 430

Gly Ser Asp Arg Trp Phe Asn Ala Leu Gly Ser Arg Arg Phe Ser Arg
        435                 440                 445

Asn Ala Cys Val Val Ser Cys Gly Thr Ala Val Thr Val Asp Ala
    450                 455                 460

Leu Thr Asp Asp Gly His Tyr Leu Gly Gly Thr Ile Met Pro Gly Phe
465                 470                 475                 480

His Leu Met Lys Glu Ser Leu Ala Val Arg Thr Ala Asn Leu Asn Arg
                485                 490                 495

His Ala Gly Lys Arg Tyr Pro Phe Pro Thr Thr Thr Gly Asn Ala Val
            500                 505                 510
```

```
Ala Ser Gly Met Met Asp Ala Val Cys Gly Ser Val Met Met Met His
        515                 520                 525
Gly Arg Leu Lys Glu Lys Thr Gly Ala Gly Lys Pro Val Asp Val Ile
    530                 535                 540
Ile Thr Gly Gly Gly Ala Ala Lys Val Ala Glu Ala Leu Pro Pro Ala
545                 550                 555                 560
Phe Leu Ala Glu Asn Thr Val Arg Val Ala Asp Asn Leu Val Ile His
                565                 570                 575
Gly Leu Leu Asn Leu Ile Ala Ala Glu Gly Gly Glu Ser Glu His Thr
            580                 585                 590
```

<210> SEQ ID NO 23
<211> LENGTH: 753
<212> TYPE: DNA
<213> ORGANISM: Clostridium acetobutylicum

<400> SEQUENCE: 23

```
aataagagag cagcttttat gctgctctta tttttaagga gtgtattaaa agtgatttta      60
gttttagatg ttggcaatac taatatagtg ttaggaatat acaatgatac gaaacttaca     120
gctgaatgga gactatcaac agatgtatta agatctgctg acgaatatgg aattcaagta     180
atgaacttat ttcaacaaga taagctcgat ccaacattag ttgagggagt aataatatcc     240
tctgttgtac taatatcat gtattcttta gaacatatga taagaaagta ctttaagata     300
aatccattag ttgttggacc tggaataaaa acaggaatta atattaaata cgataatcct     360
aaagaagttg gagccgacag aattgtaaat gctgtagcag cacatgaaat ttataaaaga     420
tctcttataa taatagattt tggaacagca actacatttt gtgcagtaag agaaaatgga     480
gattatcttg gtggagcaat atgccctgga attaaagttt catcagaggc tcttttttgaa     540
aaggcagcta agcttccaag agtagagctc ataaaaccag cgtatgctat ttgtaaaaat     600
actatttcaa gtatacaatc tggaattgtt tatcgatacc tacgtcaggt aaaaatactta     660
tttgaaaaat tgaaagaaaa cctgccggac ggaaggagaa caaggacctc cttggtattg     720
gccacaggtg gtcttgccaa acttattaat tga                                   753
```

<210> SEQ ID NO 24
<211> LENGTH: 798
<212> TYPE: DNA
<213> ORGANISM: Streptomyces coelicolor

<400> SEQUENCE: 24

```
atgctgctga cgatcgacgt aaggaacacg cacaccgtcc tcggcctctt cgacggcgag      60
gacatcgtcg agcactggcg catctccacg gactcgcgcc gcacggccga cgaactggcg     120
gtgctcctcc agggcctcat gggcatgcat cccctcctcg gcgacgaact gggcgacggc     180
atcgacggca tcgccatctg cgcgacggtc ccctccgtcc tccacgaact gcgcgaggtc     240
acccgccgct actacggcga cgtccccgcg gtcctcgtcg aaccgggcgt caagaccggc     300
gtcccgatcc tcaccgacca ccccaaggag gtcggcgccg accgcatcat caacgcggta     360
gcggccgtgg agctctacgg cggcccggcg atcgtcgtgg acttcggcac ggcgacgacg     420
ttcgacgcgg tcagcgcgcg cggggagtac atcggcggcg tcatcgcccc cggcatcgag     480
atctcggtcg aggcgctggg cgtcaagggc gcccagctcc gcaagatcga ggtggcgcgc     540
ccccgcagcg tgatcggcaa gaacacggtc gaggcgatgc agtccggcat cgtgtacggc     600
ttcgccggcc aggtcgacgg cgtcgtcaac cgcatggcgc gggagctggc cgacgacccg     660
```

```
gacgacgtga cggtcatcgc gacgggcggg ctggcgccga tggtcctggg cgagtcctcg    720
gtcatcgacg agcacgagcc gtggctgacg ctgatgggtc tgcgcctggt gtacgagcgc    780
aacgtgtcgc gcatgtag                                                  798
```

```
<210> SEQ ID NO 25
<211> LENGTH: 819
<212> TYPE: DNA
<213> ORGANISM: Mycobacterium tuberculosis

<400> SEQUENCE: 25
gtgctgctgg cgattgacgt ccgcaacacc cacaccgttg tgggcctgct gtccggaatg     60
aaagagcacg caaaggtcgt gcagcagtgg cggatacgca ccgaatccga agtcaccgcc    120
gacgaactgg cactgacgat cgacgggctg atcggcgagg attccgagcg gctcaccggt    180
accgccgcct tgtccacggt cccgtccgtg ctgcacgagg tgcggataat gctcgaccag    240
tactggccgt cggtgccgca cgtgctgatc gagcccggag tacgcaccgg gatccctttg    300
ctcgtcgaca acccgaagga agtgggcgca gaccgcatcg tgaactgttt ggccgcctat    360
gaccggttcc ggaaggccgc catcgtcgtt gactttggat cctcgatctg tgttgatgtt    420
gtatcggcca agggtgaatt tcttggcggc gccatcgcgc ccggggtgca ggtgtcttcc    480
gatgccgcgg cggcccgctc ggcggcattg cgccgcgttg aacttgcccg ccacgttcg    540 gtggttggca agaacaccgt cgaatgcatg caagccggtg cggtgttcgg cttcgccggg    600
ctggtagacg ggttggtagg ccgcatccgc gaggacgtgt ccggtttctc cgtcgaccac    660
gatgtcgcga tcgtggctac cgggcatacc gcgccctgc tgctgccgga attgcacacc    720
gtcgaccatt acgaccagca cctgaccttg cagggtctgc ggctggtgtt cgagcgtaac    780
ctcgaagtcc agcgcggccg gctcaagacg gcgcgctga                           819
```

```
<210> SEQ ID NO 26
<211> LENGTH: 777
<212> TYPE: DNA
<213> ORGANISM: Rhodobacter capsulatus

<400> SEQUENCE: 26
atgcttttgt gcatcgactg cggcaacacc aacaccgtgt tttcggtctg ggacgggacg     60
gatttcgccg ccacctggcg catcgccacc gatcatcgcc gcaccgccga cgaatatttc    120
gtctggctga acacgctgat gcaactgaag ggcctgcagg gccggatctc cgaggcgatc    180
atctcctcga ccgcgccgcg ggtggtgttc aacctgcgcg ttctgtgcaa ccgctatttc    240
gactgccgcc cctatgtcgt cggcaaaccg ggctgcgagc tgccggtggc gccgcgcgtc    300
gatccgggca ccaggtcgg gccggaccgg ctggtcaata cggtggcggg ctatgaccgt    360
catggcggcg atctgatcgt cgtcgatttc ggcaccgcca ccacctttga cgtggtggcc    420
cccgatggcg cctatatcgg cggggtgatc gcgcccgggg tgaacctgag ccttgaggcg    480
ctgcatatgg cggcggccgc gctgccgcat gtcgacgtca cgaaaccgca aggggtgatc    540
ggcacgaata cggtggcctg catccaatcc ggggtgtatt ggggctatat cggccttgtc    600
gaaggcatcg tgcggcagat ccggatggaa cgtgaccgtc cgatgaaggt gattgccacc    660
gggggtcttg cctcgctctt cgatctgggt ttcgatctgt tcgacaaggt cgaggatgac    720
ctgaccatgc atggtctgcg tctgatcttc gattacaaca agggacttgg ggcgtga       777
```

```
<210> SEQ ID NO 27
<211> LENGTH: 768
```

<212> TYPE: DNA
<213> ORGANISM: Geobacter sulfurreducens

<400> SEQUENCE: 27

```
gtgcttcttg ttatagacgt gggtaatacc aatatcgtgc tcgggattta cgatggcgag      60
cgcctggtga gggattggcg ggtctccacg acaaggccc gtactaccga cgagtacggt     120
attctcataa atgagttgtt ccgcttggcg ggccttgggc tcgatcagat ccgcgcggtg     180
atcatctcct cggtggtgcc gccctcacc ggcgtgctgg agcgtctttc cctggggtat     240
ttcgggatgc gtcccctggt ggtgggaccg ggcatcaaga caggcatgcc aatccagtac     300
gacaacccc gggaggtggg ggccgaccgg atcgtgaacg cggtggcggg gtacgagaag     360
taccgcacct ctctcattat cgtcgatttc ggcaccgcta ccacgttcga ctacgtgaac     420
cgcaagggag agtactgcgg aggggccatc gcgccgggac tcgtcatttc caccgaggcc     480
ctgttccagc gggccagcaa gctgcccagg gttgatatca tacgtccgtc cgcgatcatt     540
gccaggaaca cggtcaattc gatgcaggcg ggaatttact atggttacgt ggggctcgta     600
gacgagatcg tcacccggat gaaggccgag agcaaggatg cgccccgggt tatcgctacc     660
ggagggttgg cgtccctcat agcgccggag tccaagacca tcgaagccgt cgaggaatat     720
ctgacactgg agggattgcg catactgtac gaacgaaaca gggagtga                  768
```

<210> SEQ ID NO 28
<211> LENGTH: 789
<212> TYPE: DNA
<213> ORGANISM: Deinococcus radiodurans

<400> SEQUENCE: 28

```
gtgcccgctt ttcccctgct cgccgtggac atcggcaaca ccaccaccgt cctgggtctg      60
gccgacgcct cgggcgccct gacccacacc tggcggattc ggaccaaccg cgagatgctg     120
cccgacgacc tcgcgctgca actgcacggg ctctttaccc tcgccggggc gccgattccc     180
cgcgccgccg tgctgagcag cgtggcgccc ccggtgggcg aaaactacgc gctcgcgctc     240
aagcggcact tcatgatcga cgcttttgcc gtgagtgccg agaacctgcc cgacgtgacg     300
gtggaactcg acacgccggg ctcggtgggt gcggaccgcc tgtgcaacct cttcggcgcc     360
gaaaagtacc tggggggggct ggactacgcg gtggtagtgg atttcgggac ctccaccaac     420
tttgacgtgg tggggcgggg gcggcgtttc ctcggcggca tcctcgccac cggagcgcag     480
gtcagcgccg acgccctgtt cgccgcgcc gccaaactgc cgcgcatcac cctgcaagcg     540
cccgagacgg ccatcggcaa aaacaccgtc cacgcgctgc aatcgggcct ggtcttcggc     600
tacgccgaga tgtggacgg cctgctgcgc cgcatccgcg ccgagttgcc gggcgaagcg     660
gtcgccgtcg ccactggcgg cttctcgcgc accgtgcagg ggatttgcca ggaaatcgac     720
tactacgacg aaacgctgac gttgcgcggg ttggtggagc tgtgggcgag ccgttcggag     780
gtccgctga                                                             789
```

<210> SEQ ID NO 29
<211> LENGTH: 741
<212> TYPE: DNA
<213> ORGANISM: Thermotoga maritima

<400> SEQUENCE: 29

```
ttgtacctcc tcgtggacgt gggtaacacg cattctgtct tctctatcac cgaagatggt      60
aaaactttca gaaggtggag gctgtccacc ggtgtgtttc agacggaaga cgaactcttt     120
```

-continued

```
tcacaccttc atcctcttct gggcgatgct atgcgtgaga taaagggat aggagtggcc      180 tccgtcgttc ccactcagaa cacagtcata gagcgttttt ctcaaaagta tttccacata    240
tcaccgatat gggtgaaggc gaaaaacgga tgtgtgaaat ggaacgtgaa gaatccctcg    300
gaagtgggtg ctgatagggt ggccaacgtt gtcgctttcg tcaaggaata cggtaaaaac    360
ggaatcatca tcgacatggg aacggcaacc accgtggatc ttgttgtgaa cggatcttac    420
gaaggaggag ccattttgcc tggattcttc atgatggttc actcgctctt cggggaacg    480 gcaaaacttc cgctcgttga ggtaaaacca gcggattttg ttgtaggaaa ggatacggag    540
gaaaacatca ggctgggtgt ggtgaacgga agtgtctacg ctcttgaggg gataataggg    600
cgaataaagg aagtttacgg tgatttaccg gtggttctca cgggaggtca gtcgaagatc    660
gtgaaagata tgataaaaca cgagattttc gatgaggacc tcacgatcaa ggggtgtac    720 catttctgct cggagattg a                                                741

<210> SEQ ID NO 30
<211> LENGTH: 822
<212> TYPE: DNA
<213> ORGANISM: Treponema pallidum

<400> SEQUENCE: 30
atgcttttga tagacgtagg gaactcgcac gtagtgttcg gaatccaagg cgagaatggt     60
ggccgtgtgt gcgtgcgtga gttgtttcgc cttgcgcctg acgcgcgtaa acccaagat    120 gagtactcgc ttctcatcca tgcgctttgc gaacgtgcgg gggtcggccg tgcttctctc    180
cgtgatgcgt ttatttcctc cgtcgtgcct gtgttgacaa agaccattgc agatgcggtc    240
gctcagatta gcggcgtcca gccggttgtc tttggcccgt gggcgtacga gcacttgccg    300
gtgcgcatac cagagccagt gcgcgcggaa attggcactg acttggtagc caacgcggtg    360
gcggcctatg tgcatttccg ttctgcttgc gtggtagtgg attgtggaac agcgctcacc    420
tttacggcgg tggatggcac ggggttgatt caaggggtgg caattgcgcc tggtctgcgc    480
actgcggtgc agtctctcca tacaggaacg cacaattac cacttgttcc tcttgccctg    540
cctgattccg ttctgggcaa ggatactacg catgcggtgc aggcgggtgt ggtgcggggc    600
acgctctttg ttattcgcgc tatgattgca cagtgtcaga agagttagg gtgccgctgt    660 gcagcggtga taacgggggg gctttcgcgt cttttctcgt cagaggtgga ctttcctcct    720
atcgatgcac agctgacgct tcaggtcttt gcacatattg cgcggctggt gccgacatct    780
ctcctgccac ctgctacagt gtcaggttca tcggggaatt ga                       822

<210> SEQ ID NO 31
<211> LENGTH: 789
<212> TYPE: DNA
<213> ORGANISM: Borrelia burgdorferi

<400> SEQUENCE: 31
atgaataaac ctttattatc agaattgata attgatattg aaataccag cattgctttt      60 gccttattta aagataatca agttaattta tttattaaaa tgaaaacaaa tcttatgtta    120
aggtatgatg aggtttatag cttttttgaa gaaaattttg attttaatgt aaataaagtt    180
tttataagca gcgttgttcc tattcttaat gaaacattta aaaatgtcat ttttctcttt    240
tttaagataa agcctttgtt tattggtttt gatttgaatt atgatttgac atttaatcct    300
tacaaaagcg ataaattttt gctaggttca gacgttttttg ccaatcttgt tgcagccatt    360
gaaaattatt catttgaaaa tgttttagta gtagaccttg aactgcttg caccattttt    420
```

```
gctgttagca ggcaagatgg aatactcggt ggtattataa attctggtcc tttgataaat      480
tttaattctt tattagataa tgcctatctt atcaaaaaat tccccattag cactccaaat      540
aatcttttag agagaacgac atctgggagt gtaaacagcg gttattttta tcaatataag      600
tatttaatag aaggtgttta tcgtgatatt aagcagatgt ataaaaaaaa atttaattta      660
ataattactg ggggtaatgc ggacctaatt ttgtcattaa ttgagataga gtttattttt      720
aatattcatt taactgtaga aggcgttaga attttaggaa attctattga ctttaagttt      780
gttaattga                                                              789

<210> SEQ ID NO 32
<211> LENGTH: 690
<212> TYPE: DNA
<213> ORGANISM: Aquifex aeolicus

<400> SEQUENCE: 32
atgaggtttt tgacggtaga cgtagggaat tcctccgttg atatcgccct atgggaaggg       60
aagaaagtaa aagattttct gaaactttca cacgaagaat ttttaaagga agaatttcct      120
aaattaaaag cgctcggaat atccgtaaaa cagagtttta gcgaaaaagt aaggggaaaa      180
ataccgaaga taaagttttt aaagaaggaa aactttccta tacaggttga ttacaaaact      240
cctgaaacgc tgggcacgga cagggtagca cttgcttact ccgccaaaaa gttttacgga      300
aagaatgttg tagtaatcag tgcgggtact gcccttgtaa ttgacctagt tcttgagggc      360
aaatttaagg gagggtttat taccttagga cttggaaaga agttaaaaat tctttccgac      420
ctggcggagg gaattcccga ttttttccc gaagaggtag aaattttct tgggcgttct      480 acacgagagt gcgtcctggg aggggcttac agggagagca cagaatttat taaaagtaca      540
ctgaaactct ggagaaaagt atttaaaaga aagttcaaag tggttataac gggcggagag      600
gggaagtact tttccaagtt cggtatttac gaccccactcc ttgttcacag gggcatgaga      660
aatttacttt acctctatca caggatttaa                                      690

<210> SEQ ID NO 33
<211> LENGTH: 774
<212> TYPE: DNA
<213> ORGANISM: Synechocystis sp.

<400> SEQUENCE: 33
gtggaaacat caaagccggg ttgtggttta gccctggata tgacaagca aaaaccttgg       60 ttaggcctaa tgataggcaa ctcccgtctg cactgggcat attgtagcgg caatgctccc      120
ctgcaaacct gggttacaga ttacaacccc aagtcagctc agttgccggt tttgttgggg      180
aaagttcctc tgatgttggc atcggtggta ccggaacaaa ccgaagtttg gcgagtatat      240
cagcctaaaa ttttgaccct gaagaatctt ccctggtca atctttaccc cagctttggc      300
attgaccggg ccctggctgg tttagggacg gggctgacct acggctttcc ctgtctagtg      360
gttgatggag gcactgcttt gaccattaca gggtttgacc aagataaaaa actggtgggg      420
ggagcgatct tgcccggttt gggattgcag ttagcaaccc ttggcgatcg cctggcggcc      480
ctaccgaagt tagaaatgga tcaattaacc gagttgcctg accgttgggc tttagatacc      540
cccagcgcca tttttagtgg tgttgtctat ggcgtgttgg gggcattgca gagttatctc      600
caggattggc aaaagctttt tcctggtgcc gccatggtta tcaccggggg agacggcaag      660
atattacatg gcttcctaaa agagcattct cctaatcttt cggtgccctg ggatgacaat      720
```

```
ttgatcttcc tcggtatggc ggccatacac cacggcgatc gccccatctg ttag         774
```

<210> SEQ ID NO 34
<211> LENGTH: 672
<212> TYPE: DNA
<213> ORGANISM: Helicobacter pylori

<400> SEQUENCE: 34

```
atgccagcta ggcaatcttt caaggattta aaagacttga ttttatgcga tataggcaac    60
acacgcatcc atttcgcgca aaactaccag ctcttttcaa gcgctaaaga agatttaaag   120
cgtttgggta ttcaaaagga aattttttac attagtgtga atgaagaaaa tgaaaaagct   180
cttttaaatt gttaccctaa cgctaaaaat atcgcagggt tttttcattt agaaaccgac   240
tatatagggc ttgggataga ccggcaaatg gcatgtttag cggtggttaa tggggttata   300
gtggatgctg ggagcgcgat tacgattgat ttagtcaaag agggcaagca tttaggaggg   360
tgtattttgc ccggtttagc ccaatatgtc catgcgtata aaaaaagcgc gaaaatctta   420
gagcaacctt tcaaagcctt agattcttta aagtttttac ccaaaaacac cagagacgct   480
gtgaattacg gcatgatttt gagtatcatc tcttgtatcc aacatttagc taaagatcaa   540
aaaatctatc tttgtggggg cgatgcgaaa tatttgagcg cgttttttacc tcattctgtt   600
tgcaaggagc gtttggtttt tgacgggatg gaaatcgctc ttaaaaaagc agggatacta   660
gaatgcaaat ga                                                       672
```

<210> SEQ ID NO 35
<211> LENGTH: 747
<212> TYPE: DNA
<213> ORGANISM: Pseudomonas aeruginosa

<400> SEQUENCE: 35

```
atgattcttg agctcgactg tggaaactcg ctgatcaagt ggcgggtcat cgagggggcg    60
gcgcggtcgg tcgccggtgg ccttgcggag tccgatgatg ccctggtcga acagttaacg   120
tcgcagcaag cgctgccagt gcgagcctgt cgcctggtga cgttcgcag cgagcaggaa   180
acctcgcaac tggtcgcacg gttggagcag ctgttcccgg tttcggcgct ggttgcatca   240
tccggcaagc agttggcggg tgtgcgcaac ggctatctcg attaccagcg cctggggctc   300
gaccgctggc tggccctcgt cgcggctcat cacctggcta agaaggcctg cctggtcatt   360
gatctgggga ccgcggtcac ctctgacctg gtcgcggcgg atggagtgca tctgggggc   420
tacatatgcc cgggcatgac cctgatgaga agccagttgc gcacccatac ccgacgtatc   480
cgctacgacg atgcagaggc ccggcgggcg cttgccagtc tccagccagg caggccacg   540
gccgaggcgg ttgagcgggg ttgtctgctc atgctcaggg ggttcgttcg tgagcagtac   600
gccatggcgt gcgagctgct cggtccggat tgtgaaatat tcctgacggg tggggatgcc   660
gaactggttc gcgacgaact ggctggcgcc cggatcatgc cggacctggt tttcgtaggg   720
ctggcactgg cttgcccgat tgagtga                                       747
```

<210> SEQ ID NO 36
<211> LENGTH: 630
<212> TYPE: DNA
<213> ORGANISM: Campylobacter jejuni

<400> SEQUENCE: 36

```
atgttgctct gtgatattgg gaattcaaat gctaatttcc tagatgataa caaatatttt    60
actcttaata tagatcagtt tttagaattt aaaaatgaac aaaaaatttt ttatatcaat   120
```

```
gtcaatgaac atctcaaaga acatttaaaa aatcaaaaaa attttatcaa tcttgaacct      180 tatttttat ttgatacaat ttatcaagga ttaggaatcg atcgcatagc agcttgttat       240
actattgaag atggagttgt tgtagatgca ggtagtgcta ttacaattga tattatttct      300
aattctatac atcttggtgg ttttatcttg ccaggtattg caaattataa aaaaatttat     360
agccatattt caccacgatt aaaaagtgaa tttaacactc aagttagtct tgatgcattc      420
ccacaaaaaa ccatggatgc tttaagttat ggtgttttta aaggaattta cctactgata     480
aaagatgccg ctcaaaataa aaagctttat ttcactggtg agatgggca atttttagca      540 aattatttcg atcacgcaat ttatgataaa cttttaatct ttcgaggaat gaaaaagatt     600
ataaaagaaa atcccaattt actttattaa                                      630

<210> SEQ ID NO 37
<211> LENGTH: 1779
<212> TYPE: DNA
<213> ORGANISM: Neisseria meningitidis

<400> SEQUENCE: 37
atgacggttt tgaagccttc gcactggcgg gtgttggcgg agcttgccga cggtttgccg       60
caacacgtct cgcaactggc gcgtatggcg gatatgaagc cgcagcagct caacggtttt     120
tggcagcaga tgccggcgca catacgcggg ctgttgcgcc aacacgacgg ctattggcgg     180
ctggtgcgcc cattggcggt tttcgatgcc gaaggtttgc gcgagctggg ggaaaggtcg     240
ggttttcaga cggcattgaa gcacgagtgc gcgtccagca acgacgagat actggaattg     300
gcgcggattg cgccggacaa ggcgcacaaa accatatgtg tgacccacct gcaaagtaag     360 ggcaggggc ggcaggggcg gaagtggtcg caccgtttgg gcgagtgtct gatgttcagt      420
tttggctggg tgtttgaccg gccgcagtat gagttgggtt cgctgtcgcc tgttgcggca     480
gtggcgtgcc ggcgcgcctt gtcgcgtttg ggtttgaaaa cgcaaatcaa gtggccaaac    540
gatttggtcg tcggacgcga caaattgggc ggcattctga ttgaaacggt caggacgggc     600
ggcaaaacgg ttgccgtggt cggtatcggc atcaatttcg tgctgcccaa ggaagtggaa     660
aacgccgctt ccgtgcaatc gctgtttcag acggcatcgc ggcggggaaa tgccgatgcc     720
gccgtgttgc tggaaacgct gttggcggaa cttgatgcgg tgttgttgca atatgcgcgg    780
gacggatttg cgccttttgt ggcggaatat caggctgcca accgcgacca cggcaaggcg    840
gtattgctgt tgcgcgacgg cgaaaccgtg ttcgaaggca cggttaaagg cgtggacgga    900
caaggcgttc tgcacttgga aacggcagag ggcaaacaga cggtcgtcag cggcgaaatc   960
agcctgcggt ccgacgacag gccggtttcc gtgccgaagc ggcgggattc ggaacgtttt   1020
ctgctgttgg acggcggcaa cagccggctc aagtgggcgt gggtggaaaa cggcacgttc   1080
gcaaccgtcg gtagcgcgcc gtaccgcgat ttgtcgcctt gggcgcgga gtgggcggaa    1140 aaggtggatg gaaatgtccg catcgtcggt tgcgccgtgt gcggagaatt caaaaaggca   1200
caagtgcagg aacagctcgc ccgaaaaatc gagtggctgc cgtcttccgc acaggctttg   1260
ggcatacgca accactaccg ccacccgaa gaacacggtt ccgaccgctg gttcaacgcc     1320
ttgggcagcc gccgcttcag ccgcaacgcc tgcgtcgtcg tcagttgcgg cacggcggta    1380
acggttgacg cgctcaccga tgacggacat tatctcgggg gaaccatcat gcccggtttc   1440
cacctgatga agaatcgct cgccgtccga accgccaacc tcaaccggca cgccggtaag    1500
cgttatcctt tcccgaccac aacgggcaat gccgtcgcca gcggcatgat ggatgcggtt   1560
```

```
tgcggctcgg ttatgatgat gcacgggcgt ttgaaagaaa aaaccggggc gggcaagcct      1620
gtcgatgtca tcattaccgg cggcggcgcg gcaaaagttg ccgaagccct gccgcctgca      1680
tttttggcgg aaaataccgt gcgcgtggcg gacaacctcg tcattcacgg gctgctgaac      1740
ctgattgccg ccgaaggcgg ggaatcggaa catacttaa                             1779
```

<210> SEQ ID NO 38
<211> LENGTH: 804
<212> TYPE: DNA
<213> ORGANISM: Bordetella pertussis

<400> SEQUENCE: 38

```
atgattatcc tcatcgactc cggcaacagc cgcctcaaag tcggctggtt tgacccggac       60
gcgccgcagg cggcgcgcga gcccgccccc gtcgccttcg acaatctcga cctggacgcg      120
ctgggccgct ggctggccac cctgcccagg cgcccgcaac gggcgctggg cgtgaacgtc      180
gccgggcttg cccgcggcga agccattgcc gccacgctgc gcgcgggcgg ttgcgacatc      240
cggtggctgc gggcccagcc cctggccatg gggctgcgca acggctatcg caatcccgac      300
caactgggcg ccgaccgctg ggcgtgcatg gtgggcgtgc tggcgcgcca gccgtccgtg      360
cacccgccgc tgctggtggc cagtttcggc acggccacca cgctggacac catcgggccc      420
gacaatgtct ttcccggcgg gctgatcctg cccggccccg ccatgatgcg cggcgcgctg      480
gcctacggca ccgcccacct gccctggcc gacggcctgg tggccgacta ccccatcgac      540
acccatcagg ccatcgccag cggcatcgcc gccgcccagg ccggcgcgat cgtgcggcaa      600
tggctggccg ccgccaacg ctacggccag cgccggaga tctatgtcgc cggcggcggg      660
tggcccgaag tgcggcagga agccgagcgc ctgctggcgg tcaccggcgc cgccttcggc      720
gccacgccgc agcccactta cctcgacagc cccgtgctcg acggcctggc ggcgctcgcc      780
gcgcaaggcg cgccaacggc ctga                                             804
```

<210> SEQ ID NO 39
<211> LENGTH: 460
<212> TYPE: PRT
<213> ORGANISM: Neisseria gonorrhoeae

<400> SEQUENCE: 39

```
Met Gly Glu Cys Leu Met Phe Ser Phe Gly Trp Ala Phe Asp Arg Pro
1               5                   10                  15

Gln Tyr Glu Leu Gly Ser Leu Ser Pro Val Ala Ala Leu Ala Cys Arg
            20                  25                  30

Arg Ala Leu Gly Cys Leu Gly Leu Glu Thr Gln Ile Lys Trp Pro Asn
        35                  40                  45

Asp Leu Val Val Gly Arg Asp Lys Leu Gly Gly Ile Leu Ile Glu Thr
    50                  55                  60

Val Arg Ala Gly Gly Lys Thr Val Ala Val Gly Ile Gly Ile Asn
65                  70                  75                  80

Phe Val Leu Pro Lys Glu Val Glu Asn Ala Ala Ser Val Gln Ser Leu
            85                  90                  95

Phe Gln Thr Ala Ser Arg Arg Gly Asn Ala Asp Ala Ala Val Leu Leu
        100                 105                 110

Glu Thr Leu Leu Ala Glu Leu Gly Ala Val Leu Glu Gln Tyr Ala Glu
    115                 120                 125

Glu Gly Phe Ala Pro Phe Leu Asn Glu Tyr Glu Thr Ala Asn Arg Asp
    130                 135                 140
```

His Gly Lys Ala Val Leu Leu Arg Asp Gly Glu Thr Val Cys Glu
145                 150                 155                 160

Gly Thr Val Lys Gly Val Asp Gly Arg Gly Val Leu His Leu Glu Thr
            165                 170                 175

Ala Glu Gly Glu Gln Thr Val Val Ser Gly Glu Ile Ser Leu Arg Pro
        180                 185                 190

Asp Asn Arg Ser Val Ser Val Pro Lys Arg Pro Asp Ser Glu Arg Phe
    195                 200                 205

Leu Leu Leu Glu Gly Gly Asn Ser Arg Leu Lys Trp Ala Trp Val Glu
    210                 215                 220

Asn Gly Thr Phe Ala Thr Val Gly Ser Ala Pro Tyr Arg Asp Leu Ser
225                 230                 235                 240

Pro Leu Gly Ala Glu Trp Ala Glu Lys Ala Asp Gly Asn Val Arg Ile
                245                 250                 255

Val Gly Cys Ala Val Cys Gly Glu Ser Lys Lys Ala Gln Val Lys Glu
            260                 265                 270

Gln Leu Ala Arg Lys Ile Glu Trp Leu Pro Ser Ser Ala Gln Ala Leu
        275                 280                 285

Gly Ile Arg Asn His Tyr Arg His Pro Glu Glu His Gly Ser Asp Arg
    290                 295                 300

Trp Phe Asn Ala Leu Gly Ser Arg Arg Phe Ser Arg Asn Ala Cys Val
305                 310                 315                 320

Val Val Ser Cys Gly Thr Ala Val Thr Val Asp Ala Leu Thr Asp Asp
                325                 330                 335

Gly His Tyr Leu Gly Gly Thr Ile Met Pro Gly Phe His Leu Met Lys
            340                 345                 350

Glu Ser Leu Ala Val Arg Thr Ala Asn Leu Asn Arg Pro Ala Gly Lys
        355                 360                 365

Arg Tyr Pro Phe Pro Thr Thr Thr Gly Asn Ala Val Ala Ser Gly Met
    370                 375                 380

Met Asp Ala Val Cys Gly Ser Ile Met Met His Gly Arg Leu Lys
385                 390                 395                 400

Glu Lys Asn Gly Ala Gly Lys Pro Val Asp Val Ile Thr Gly Gly
                405                 410                 415

Gly Ala Ala Lys Val Ala Glu Ala Leu Pro Pro Ala Phe Leu Ala Glu
            420                 425                 430

Asn Thr Val Arg Val Ala Asp Asn Leu Val Ile His Gly Leu Leu Asn
        435                 440                 445

Leu Ile Ala Ala Glu Gly Gly Glu Ser Glu His Ala
    450                 455                 460

<210> SEQ ID NO 40
<211> LENGTH: 1383
<212> TYPE: DNA
<213> ORGANISM: Neisseria gonorrhoeae

<400> SEQUENCE: 40
ttgggcgagt gcctgatgtt cagtttcgga tgggcgtttg accgcccgca gtatgagttg      60
ggttcgctgt cgcctgttgc ggcacttgcg tgccggcgcg ctttggggtg tttgggtttg     120
gaaacgcaaa tcaagtggcc aaacgatttg gtcgtcggac gcgacaaatt gggcggcatt     180
ctgattgaaa cagtcagggc gggcggtaaa acggttgccg tggtcggtat cggcatcaat     240
ttcgtgctgc ccaaggaagt ggaaaacgcc gcttccgtgc agtcgctgtt tcagacggca     300
tcgcggcggg gcaatgccga tgccgccgta ttgctggaaa cattgcttgc ggaactgggc     360

-continued

```
gcggtgttgg aacaatatgc ggaagaaggg ttcgcgccat ttttaaatga gtatgaaacg      420
gccaaccgcg accacggcaa ggcggtattg ctgttgcgcg acggcgaaac cgtgtgcgaa      480
ggcacggtta aaggcgtgga cggacgaggc gttctgcact ggaaacggc agaaggcgaa       540 cagacggtcg tcagcggcga aatcagcctg cggcccgaca caggtcggt ttccgtgccg       600 aagcggccgg attcggaacg ttttttgctg ttggaaggcg ggaacagccg gctcaagtgg      660
gcgtgggtgg aaaacggcac gttcgcaacc gtgggcagcg cgccgtaccg cgatttgtcg      720
cctttgggcg cggagtgggc ggaaaaggcg gatggaaatg tccgcatcgt cggttgcgcc      780
gtgtgcggag aatccaaaaa ggcacaagtg aaggaacagc tcgcccgaaa aatcgagtgg      840
ctgccgtctt ccgcacaggc tttgggcata cgcaaccact accgccaccc cgaagaacac      900
ggttccgacc gttggttcaa cgccttgggc agccgccgct tcagccgcaa cgcctgcgtc      960
gtcgtcagtt gcggcacggc ggtaacggtt gacgcgctca ccgatgacgg acattatctc     1020
ggcggaacca tcatgcccgg cttccacctg atgaaagaat cgctcgccgt ccgaaccgcc     1080
aacctcaacc gccccgccgg caaacgttac cctttcccga ccacaacggg caacgccgtc     1140
gcaagcggca tgatggacgc ggtttgcggc tcgataatga tgatgcacgg ccgtttgaaa     1200
gaaaaaaacg gcgcgggcaa gcctgtcgat gtcatcatta ccggcggcgg cgcggcgaaa     1260
gtcgccgaag ccctgccgcc tgcatttttg gcggaaaata ccgtgcgcgt ggcggacaac     1320
ctcgtcatcc acgggctgct gaacctgatt gccgccgaag gcggggaatc ggaacacgct     1380
taa                                                                   1383
```

<210> SEQ ID NO 41
<211> LENGTH: 244
<212> TYPE: PRT
<213> ORGANISM: Porphyromonas gingivalis

<400> SEQUENCE: 41

```
Met Ser Phe Asn Leu Ile Val Asp Gln Gly Asn Ser Ala Cys Lys Val
1               5                   10                  15

Ala Phe Val Arg Asn Asn Ser Ile Glu Ser Ile Ser Phe Leu Pro Gly
            20                  25                  30

Lys Ala Gly Gln Ala Leu Ser His Leu Val Ala Pro His Arg Phe Asp
        35                  40                  45

Lys Ala Ile Tyr Ser Ser Val Gly Leu Pro Asp Glu Glu Ala Glu Ala
    50                  55                  60

Ile Val Arg Ser Cys Ala Ala Ser Leu Met Met Gly Thr Glu Thr
65                  70                  75                  80

Pro Val Pro Leu Arg Leu Gln Tyr Asp Arg Arg Thr Leu Gly Ala Asp
                85                  90                  95

Arg Leu Ala Ala Val Val Gly Ala His Ser Leu Tyr Pro Asn Thr Glu
            100                 105                 110

Leu Leu Val Ile Asp Ala Gly Thr Ala Ile Thr Tyr Glu Arg Val Ser
        115                 120                 125

Ala Glu Gly Ile Tyr Leu Gly Gly Asn Ile Ser Pro Gly Leu His Leu
    130                 135                 140

Arg Phe Lys Ala Leu His Leu Phe Thr Gly Arg Leu Pro Leu Ile Asp
145                 150                 155                 160

Pro Ser Gly Ile Ser Pro Lys Ile Ala Glu Tyr Gly Ser Ser Thr Glu
                165                 170                 175

Glu Ala Ile Thr Ala Gly Val Ile His Gly Leu Ala Gly Glu Ile Asp
```

```
                       180             185             190
Arg Tyr Ile Asp Asp Leu His Ala Lys Glu Gly Arg Ser Ala Val Ile
            195                 200                 205

Leu Thr Gly Gly Asp Ala Asn Tyr Leu Ala Arg Ile Ile Arg Ser Gly
            210                 215                 220

Ile Leu Ile His Pro Asp Leu Val Leu Leu Gly Leu Asn Arg Ile Leu
225                 230                 235                 240

Glu Tyr Asn Val

<210> SEQ ID NO 42
<211> LENGTH: 735
<212> TYPE: DNA
<213> ORGANISM: Porphyromonas gingivalis

<400> SEQUENCE: 42
atgtccttca atctgatcgt cgatcaaggc aattctgcct gtaaggttgc tttcgtccga      60 ataatagta tagagagcat ttcctttctg ccgggaaaag ccggacaggc actcagccat     120
ctcgtcgctc ctcaccgttt cgacaaggct atctactcat ctgtggggct ccccgacgaa    180
gaggctgaag ctattgtgag aagttgtgca gctgcttcct tgatgatggg gactgagacc    240
cccgtacccc ttcgcctgca atatgatcgc gcactttgg gtgccgaccg actggctgcg     300
gtggtcggag cgcatagtct ctatccgaat accgaattgc tggtgatcga cgccggtact    360
gccatcactt atgaacgagt atccgctgaa gggatctatc tcggtggcaa tatatcgccc    420
ggtctccact tgcgcttcaa ggctcttcat ctctttacgg gcaggctccc cctgattgat    480
ccttccggta tctctccgaa aatagccgag tatggctcct cgaccgaaga agcgatcaca    540
gccggagtaa ttcatggcct ggcagggag atagacagat atattgacga tctgcacgct     600
aaagaggggc ggtctgccgt tatactgacc ggaggagatg ccaactattt ggcacggatt    660
ataagaagcg gaatactaat tcatcccgat ttagtacttt tgggcctaaa tagaatttta    720
gaatataatg tataa                                                     735

<210> SEQ ID NO 43
<211> LENGTH: 592
<212> TYPE: PRT
<213> ORGANISM: Neisseria meningitidis

<400> SEQUENCE: 43

Met Thr Val Leu Lys Leu Ser His Trp Arg Val Leu Ala Glu Leu Ala
1               5                   10                  15

Asp Gly Leu Pro Gln His Val Ser Gln Leu Ala Arg Met Ala Asp Met
            20                  25                  30

Lys Pro Gln Gln Leu Asn Gly Phe Trp Gln Met Pro Ala His Ile
            35                  40                  45

Arg Gly Leu Leu Arg Gln His Asp Gly Tyr Trp Arg Leu Val Arg Pro
        50                  55                  60

Leu Ala Val Phe Asp Ala Glu Gly Leu Arg Glu Leu Gly Glu Arg Ser
65                  70                  75                  80

Gly Phe Gln Thr Ala Leu Lys His Glu Cys Ala Ser Ser Asn Asp Glu
                85                  90                  95

Ile Leu Glu Leu Ala Arg Ile Ala Pro Asp Lys Ala His Lys Thr Ile
            100                 105                 110

Cys Val Thr His Leu Gln Ser Lys Gly Arg Gly Arg Gln Gly Arg Lys
            115                 120                 125
```

```
Trp Ser His Arg Leu Gly Glu Cys Leu Met Phe Ser Phe Gly Trp Val
    130                 135                 140

Phe Asp Arg Pro Gln Tyr Glu Leu Gly Ser Leu Ser Pro Val Ala Ala
145                 150                 155                 160

Val Ala Cys Arg Arg Ala Leu Ser Arg Leu Gly Leu Asp Val Gln Ile
                165                 170                 175

Lys Trp Pro Asn Asp Leu Val Val Gly Arg Asp Lys Leu Gly Gly Ile
            180                 185                 190

Leu Ile Glu Thr Val Arg Thr Gly Gly Lys Thr Val Ala Val Val Gly
        195                 200                 205

Ile Gly Ile Asn Phe Val Leu Pro Lys Glu Val Glu Asn Ala Ala Ser
210                 215                 220

Val Gln Ser Leu Phe Gln Thr Ala Ser Arg Arg Gly Asn Ala Asp Ala
225                 230                 235                 240

Ala Val Leu Leu Glu Thr Leu Leu Val Glu Leu Asp Ala Val Leu Leu
                245                 250                 255

Gln Tyr Ala Arg Asp Gly Phe Ala Pro Phe Val Ala Glu Tyr Gln Ala
                260                 265                 270

Ala Asn Arg Asp His Gly Lys Ala Val Leu Leu Leu Arg Asp Gly Glu
            275                 280                 285

Thr Val Phe Glu Gly Thr Val Lys Gly Val Asp Gly Gln Gly Val Leu
        290                 295                 300

His Leu Glu Thr Ala Glu Gly Lys Gln Thr Val Val Ser Gly Glu Ile
305                 310                 315                 320

Ser Leu Arg Ser Asp Asp Arg Pro Val Ser Val Pro Lys Arg Arg Asp
                325                 330                 335

Ser Glu Arg Phe Leu Leu Leu Asp Gly Gly Asn Ser Arg Leu Lys Trp
                340                 345                 350

Ala Trp Val Glu Asn Gly Thr Phe Ala Thr Val Gly Ser Ala Pro Tyr
            355                 360                 365

Arg Asp Leu Ser Pro Leu Gly Ala Glu Trp Ala Glu Lys Ala Asp Gly
        370                 375                 380

Asn Val Arg Ile Val Gly Cys Ala Val Cys Gly Glu Phe Lys Lys Ala
385                 390                 395                 400

Gln Val Gln Glu Gln Leu Ala Arg Lys Ile Glu Trp Leu Pro Ser Ser
                405                 410                 415

Ala Gln Ala Leu Gly Ile Arg Asn His Tyr Arg His Pro Glu Glu His
                420                 425                 430

Gly Ser Asp Arg Trp Phe Asn Ala Leu Gly Ser Arg Arg Phe Ser Arg
            435                 440                 445

Asn Ala Cys Val Val Ser Cys Gly Thr Ala Val Thr Val Asp Ala
450                 455                 460

Leu Thr Asp Asp Gly His Tyr Leu Gly Thr Ile Met Pro Gly Phe
465                 470                 475                 480

His Leu Met Lys Glu Ser Leu Ala Val Arg Thr Ala Asn Leu Asn Arg
                485                 490                 495

His Ala Gly Lys Arg Tyr Pro Phe Pro Thr Thr Thr Gly Asn Ala Val
            500                 505                 510

Ala Ser Gly Met Met Asp Ala Val Cys Gly Ser Val Met Met Met His
        515                 520                 525

Gly Arg Leu Lys Glu Lys Thr Gly Ala Gly Lys Pro Val Asp Val Ile
530                 535                 540

Ile Thr Gly Gly Gly Ala Ala Lys Val Ala Glu Ala Leu Pro Pro Ala
```

```
                545             550             555             560
            Phe Leu Ala Glu Asn Thr Val Arg Val Ala Asp Asn Leu Val Ile Tyr
                            565             570             575
            Gly Leu Leu Asn Met Ile Ala Ala Glu Gly Arg Glu Tyr Glu His Ile
                        580             585             590

<210> SEQ ID NO 44
<211> LENGTH: 1779
<212> TYPE: DNA
<213> ORGANISM: Neisseria meningitidis

<400> SEQUENCE: 44
atgacggttt tgaagctttc gcactggcgg gtgttggcgg agcttgccga cggtttgccg      60
caacacgtct cgcaactggc gcgtatggcg gatatgaagc cgcagcagct caacggtttt     120
tggcagcaga tgccggcgca catacgcggg ctgttgcgcc aacacgacgg ctattggcgg     180
ctggtgcgcc cattggcggt tttcgatgcc gaaggtttgc gcgagctggg ggaaaggtcg     240
ggttttcaga cggcattgaa gcacgagtgc gcgtccagca acgacgagat actggaattg     300
gcgcggattg cgccggacaa ggcgcacaaa accatatgcg tgacccacct gcaaagtaag     360 ggcaggggc ggcaggggcg gaagtggtcg caccgtttgg gcgagtgtct gatgttcagt     420
tttggctggg tgtttgaccg gccgcagtat gagttgggtt cgctgtcgcc tgttgcggca     480
gtggcgtgtc ggcgcgcctt gtcgcgttta ggtttggatg tgcagattaa gtggcccaat     540
gatttggttg tcggacgcga caaattgggc ggcattctga ttgaaacggt caggacgggc     600
ggcaaaacgg ttgccgtggt cggtatcggc atcaattttg tcctgcccaa ggaagtagaa     660
aatgccgctt ccgtgcaatc gctgtttcag acggcatcgc ggcggggcaa tgccgatgcc     720
gccgtgctgc tggaaacgct gttggtggaa ctggacgcgg tgttgttgca atatgcgcgg     780
gacggatttg cgccttttgt ggcggaatat caggctgcca accgcgacca cggcaaggcg     840
gtattgctgt tgcgcgacgg cgaaaccgtg ttcgaaggca cggttaaagg cgtggacgga     900
caaggcgttt tgcacttgga aacgcgagag ggcaaacaga cggtcgtcag cggcgaaatc     960
agcctgcggt ccgacgacag gccggtttcc gtgccgaagc ggcgggattc ggaacgtttt    1020
ctgctgttgg acggcggcaa cagccggctc aagtgggcgt gggtggaaaa cggcacgttc    1080
gcaaccgtcg gtagcgcgcc gtaccgcgat ttgtcgccct tgggcgcgga gtgggcggaa    1140
aaggcggatg gaaatgtccg catcgtcggt tgcgctgtgt gcggagaatt caaaaaggca    1200
caagtgcagg aacagctcgc ccgaaaaatc gagtggctgc cgtcttccgc acaggctttg    1260
ggcatacgca accactaccg ccaccccgaa gaacacggtt ccgaccgctg gttcaacgcc    1320
ttgggcagcc gccgcttcag ccgcaacgcc tgcgtcgtcg tcagttgcgg cacggcggta    1380
acggttgacg cgctcaccga tgacggacat tatctcgggg gaaccatcat gcccggtttc    1440
cacctgatga agaatcgct cgccgtccga accgccaacc tcaaccggca cgccggtaag    1500
cgttatcctt tcccgaccac aacgggcaat gccgtcgcca gcggcatgat ggatgcggtt    1560
tgcggctcgg ttatgatgat gcacgggcgt ttgaaagaaa aaccggggc gggcaagcct    1620 gtcgatgtca tcattaccgg cggcggcgcg gcaaaagttg ccgaagccct gccgcctgca    1680
tttttggcgg aaaataccgt gcgcgtggcg gacaacctcg tcatttacgg gttgttgaac    1740
atgattgccg ccgaaggcag ggaatatgaa catatttaa                          1779

<210> SEQ ID NO 45
<211> LENGTH: 262
```

<212> TYPE: PRT
<213> ORGANISM: Bacillus anthracis

<400> SEQUENCE: 45

```
Met Ile Phe Val Leu Asp Val Gly Asn Thr Asn Ala Val Leu Gly Val
1               5                   10                  15

Phe Glu Glu Gly Glu Leu Arg Gln His Trp Arg Met Glu Thr Asp Arg
            20                  25                  30

His Lys Thr Glu Asp Glu Tyr Gly Met Leu Val Lys Gln Leu Leu Glu
        35                  40                  45

His Glu Gly Leu Ser Phe Glu Asp Val Lys Gly Ile Ile Val Ser Ser
    50                  55                  60

Val Val Pro Pro Ile Met Phe Ala Leu Glu Arg Met Cys Glu Lys Tyr
65                  70                  75                  80

Phe Lys Ile Lys Pro Leu Val Val Gly Pro Gly Ile Lys Thr Gly Leu
                85                  90                  95

Asn Ile Lys Tyr Glu Asn Pro Arg Glu Val Gly Ala Asp Arg Ile Val
            100                 105                 110

Asn Ala Val Ala Gly Ile His Leu Tyr Gly Ser Pro Leu Ile Ile Val
        115                 120                 125

Asp Phe Gly Thr Ala Thr Thr Tyr Cys Tyr Ile Asn Glu Glu Lys His
    130                 135                 140

Tyr Met Gly Gly Val Ile Thr Pro Gly Ile Met Ile Ser Ala Glu Ala
145                 150                 155                 160

Leu Tyr Ser Arg Ala Ala Lys Leu Pro Arg Ile Glu Ile Thr Lys Pro
                165                 170                 175

Ser Ser Val Val Gly Lys Asn Thr Val Ser Ala Met Gln Ser Gly Ile
            180                 185                 190

Leu Tyr Gly Tyr Val Gly Gln Val Glu Gly Ile Val Lys Arg Met Lys
        195                 200                 205

Glu Glu Ala Lys Gln Glu Pro Lys Val Ile Ala Thr Gly Gly Leu Ala
    210                 215                 220

Lys Leu Ile Ser Glu Glu Ser Asn Val Ile Asp Val Val Asp Pro Phe
225                 230                 235                 240

Leu Thr Leu Lys Gly Leu Tyr Met Leu Tyr Glu Arg Asn Ala Asn Leu
                245                 250                 255

Gln His Glu Lys Gly Glu
            260
```

<210> SEQ ID NO 46
<211> LENGTH: 789
<212> TYPE: DNA
<213> ORGANISM: Bacillus anthracis

<400> SEQUENCE: 46

```
atgattttg tattggatgt agggaacaca aatgctgtac tgggcgtgtt tgaagagggg      60
gaacttcgtc aacattggcg catggaaaca gatcgtcata agacagaaga tgaatatgga    120
atgcttgtga agcagttgct tgagcatgag ggtctttcgt ttgaagatgt gaaaggtatt    180
atcgtatctt cagtcgtgcc accaattatg tttgctttag agcgcatgtg tgaaaagtat    240
tttaaaatta gccgcttgt agtaggtcct ggaataaaaa cggggctaaa tattaaatat    300
gaaaatccac gtgaagtagg tgcggatcga atcgtaaatg cagtagcagg gatccactta    360
tatggaagtc cgcttattat tgtcgatttt ggtacggcta ctacatattg ttatattaac    420
gaagaaaagc attatatggg tggagttatt acaccgggaa ttatgatttc agcagaggct    480
```

```
ttatatagta gagccgcaaa acttcctcgt attgaaatta caaaaccaag cagtgtagtt      540
gggaagaata cggtaagtgc gatgcaatct ggtattcttt atggttatgt tggacaagtg      600
gaaggtattg ttaagcgcat gaaagaggaa gctaaacaag aaccgaaagt tattgcaaca      660
ggtggattgg cgaaattaat ttcagaagaa tcgaatgtga ttgatgttgt agatccattt      720
ttaacattaa aaggtttgta tatgttatac gagcggaatg caaatttaca gcatgagaaa      780
ggtgaataa                                                              789
```

<210> SEQ ID NO 47
<211> LENGTH: 254
<212> TYPE: PRT
<213> ORGANISM: Bacillus halodurans

<400> SEQUENCE: 47

```
Met Ile Leu Val Ile Asp Val Gly Asn Thr Asn Thr Val Leu Gly Val
1               5                   10                  15

Tyr Gln Asp Glu Thr Leu Val His His Trp Arg Leu Ala Thr Ser Arg
            20                  25                  30

Gln Lys Thr Glu Asp Glu Tyr Ala Met Thr Val Arg Ser Leu Phe Asp
        35                  40                  45

His Ala Gly Leu Gln Phe Gln Asp Ile Asp Gly Ile Val Ile Ser Ser
    50                  55                  60

Val Val Pro Pro Met Met Phe Ser Leu Glu Gln Met Cys Lys Lys Tyr
65                  70                  75                  80

Phe His Val Thr Pro Met Ile Ile Gly Pro Gly Ile Lys Thr Gly Leu
                85                  90                  95

Asn Ile Lys Tyr Asp Asn Pro Lys Glu Val Gly Ala Asp Arg Ile Val
            100                 105                 110

Asn Ala Val Ala Ala Ile Glu Leu Tyr Gly Tyr Pro Ala Ile Val Val
        115                 120                 125

Asp Phe Gly Thr Ala Thr Thr Tyr Cys Leu Ile Asn Glu Lys Lys Gln
    130                 135                 140

Tyr Ala Gly Gly Val Ile Ala Pro Gly Ile Met Ile Ser Thr Glu Ala
145                 150                 155                 160

Leu Tyr His Arg Ala Ser Lys Leu Pro Arg Ile Glu Ile Ala Lys Pro
                165                 170                 175

Lys Gln Val Val Gly Thr Asn Thr Ile Asp Ser Met Gln Ser Gly Ile
            180                 185                 190

Phe Tyr Gly Tyr Val Ser Gln Val Asp Gly Val Val Lys Arg Met Lys
        195                 200                 205

Ala Gln Ala Glu Ser Glu Pro Lys Val Ile Ala Thr Gly Gly Leu Ala
    210                 215                 220

Lys Leu Ile Gly Thr Glu Ser Glu Thr Ile Asp Val Ile Asp Ser Phe
225                 230                 235                 240

Leu Thr Leu Lys Gly Leu Gln Leu Ile Tyr Lys Lys Asn Val
                245                 250
```

<210> SEQ ID NO 48
<211> LENGTH: 765
<212> TYPE: DNA
<213> ORGANISM: Bacillus halodurans

<400> SEQUENCE: 48

```
atgatacttg tcattgatgt tggaaataca aatactgtgt tagggtctta ccaagatgaa       60
```

```
acgttagtgc atcattggcg gctagcgacg agtaggcaaa agaccgagga tgagtatgca      120
atgacggtgc gttctctctt tgatcatgca ggtctacagt ttcaagacat agacggcatt      180
gtcatttcat ctgttgtccc accgatgatg ttttccttag agcaaatgtg caaaaaatac      240
tttcatgtca ctcctatgat tattgggcct ggaattaaga caggcttaaa tattaagtat      300
gacaatccaa agagggttgg ggccgatcga atcgttaatg cagttgcagc gattgagtta      360
tatggctacc ctgccattgt cgttgatttt ggaacagcaa caacatattg cttaattaat      420 gaaaaaaac aatatgcagg gggagtcatt gctcctggaa tcatgatctc aacagaagcg       480
ttgtatcatc gcgcatcaaa attgccacgg attgaaatag cgaagccgaa acaagtcgta      540
gggacaaata cgattgattc gatgcaatca ggaatcttct acgggtatgt gagccaagtc      600
gatggtgttg tgaaacgaat gaaggctcaa gcagaaagtg aaccgaaagt cattgcaact      660
ggtgggcttg cgaagttaat cggaaccgag tcggaaacca ttgatgtaat cgattcgttt      720
ttaacattaa aaggattgca actcattat  aagaagaatg tctga                      765
```

<210> SEQ ID NO 49
<211> LENGTH: 258
<212> TYPE: PRT
<213> ORGANISM: Bacillus stearothermophilus

<400> SEQUENCE: 49

```
Met Ile Phe Val Leu Asp Val Gly Asn Thr Asn Thr Val Leu Gly Val
1               5                   10                  15

Tyr Asp Gly Asp Glu Leu Lys His His Trp Arg Ile Glu Thr Ser Arg
            20                  25                  30

Ser Lys Thr Glu Asp Glu Tyr Gly Met Met Ile Lys Ala Leu Leu Asn
        35                  40                  45

His Val Gly Leu Gln Phe Ser Asp Ile Arg Gly Ile Ile Ser Ser
    50                  55                  60

Val Val Pro Pro Ile Met Phe Ala Leu Glu Arg Met Cys Leu Lys Tyr
65                  70                  75                  80

Phe His Ile Lys Pro Leu Ile Val Gly Pro Gly Ile Lys Thr Gly Leu
                85                  90                  95

Asp Ile Lys Tyr Asp Asn Pro Arg Glu Val Gly Ala Asp Arg Ile Val
            100                 105                 110

Asn Ala Val Ala Gly Ile His Leu Tyr Gly Ser Pro Leu Ile Ile Val
        115                 120                 125

Asp Phe Gly Thr Ala Thr Thr Tyr Cys Tyr Ile Asn Glu His Lys Gln
    130                 135                 140

Tyr Met Gly Gly Ala Ile Ala Pro Gly Ile Met Ile Ser Thr Glu Ala
145                 150                 155                 160

Leu Phe Ala Arg Ala Ala Lys Leu Pro Arg Ile Glu Ile Ala Arg Pro
                165                 170                 175

Asp Asp Ile Ile Gly Lys Asn Thr Val Ser Ala Met Gln Ala Gly Ile
            180                 185                 190

Leu Tyr Gly Tyr Val Gly Gln Val Glu Gly Ile Val Ser Arg Met Lys
        195                 200                 205

Ala Lys Ser Lys Ile Pro Pro Lys Val Ile Ala Thr Gly Gly Leu Ala
    210                 215                 220

Pro Leu Ile Ala Ser Glu Ser Asp Ile Ile Asp Val Val Asp Pro Phe
225                 230                 235                 240

Leu Thr Leu Thr Gly Leu Lys Leu Leu Tyr Glu Lys Asn Thr Glu Lys
                245                 250                 255
```

Lys Gly

<210> SEQ ID NO 50
<211> LENGTH: 777
<212> TYPE: DNA
<213> ORGANISM: Bacillus stearothermophilus

<400> SEQUENCE: 50

```
atgattttg tattggacgt cggcaataca aacacggtgt aggggtgta tgacggggac      60
gaactgaaac atcattggcg cattgaaaca agccgctcga aacggaaga cgaatacggc    120
atgatgatca aagcgctctt gaaccatgtc ggcttgcagt tttccgacat tcgaggcatc   180
atcatttcct cggtcgtgcc gccgattatg tttgctcttg aacgcatgtg tctaaaatat   240
ttccatatca aaccgctcat cgtcggtccg ggcattaaaa ccgggctcga catcaaatat   300
gacaatccgc gtgaggtggg cgccgaccgg attgtcaacg cggttgccgg catccatttg   360
tacggcagtc cgctgattat cgtcgatttt ggcacggcga cgacgtattg ttatattaat   420
gaacataaac aatatatggg aggggccatt gccccgggaa ttatgatctc gacagaggct   480
ctgtttgcgc gggcggcgaa attgccgcgc attgaaatcg cccgcccgga tgatatcatc   540
ggcaaaaata cggtcagcgc catgcaagcc ggtattttat acggttatgt cggacaagtg   600
gaaggcatcg tgtcgcgaat gaaggcgaaa agcaaaatcc cgccgaaggt gattgctact   660
ggcggtttgg ctccgctcat tgccagcgaa tcggacatca tcgatgtcgt tgatccgttt   720
ttgacgctga ctggcttaaa attgttgtac gagaaaaaca ccgagaaaaa aggatga      777
```

<210> SEQ ID NO 51
<211> LENGTH: 260
<212> TYPE: PRT
<213> ORGANISM: Caulobacter crescentus

<400> SEQUENCE: 51

Met Leu Leu Ala Ile Glu Gln Gly Asn Thr Asn Thr Met Phe Ala Ile
1               5                   10                  15

His Asp Gly Ala Ser Trp Val Ala Gln Trp Arg Ser Ala Thr Glu Ser
            20                  25                  30

Thr Arg Thr Ala Asp Glu Tyr Val Val Trp Leu Ser Gln Leu Leu Ser
        35                  40                  45

Met Gln Gly Leu Gly Phe Arg Ala Ile Asp Ala Val Ile Ile Ser Ser
    50                  55                  60

Val Val Pro Gln Ser Ile Phe Asn Leu Arg Asn Leu Ser Arg Arg Tyr
65                  70                  75                  80

Phe Asn Val Glu Pro Leu Val Ile Gly Glu Asn Ala Lys Leu Gly Ile
                85                  90                  95

Asp Val Arg Ile Glu Lys Pro Ser Glu Ala Gly Ala Asp Arg Leu Val
            100                 105                 110

Asn Ala Ile Gly Ala Ala Met Val Tyr Pro Gly Pro Leu Val Val Ile
        115                 120                 125

Asp Ser Gly Thr Ala Thr Thr Phe Asp Ile Val Ala Ala Asp Gly Ala
    130                 135                 140

Phe Glu Gly Gly Ile Ile Ala Pro Gly Ile Asn Leu Ser Met Gln Ala
145                 150                 155                 160

Leu His Glu Ala Ala Lys Leu Pro Arg Ile Ala Ile Gln Arg Pro
                165                 170                 175

Ala Gly Asn Arg Ile Val Gly Thr Asp Thr Val Ser Ala Met Gln Ser

```
                    180                 185                 190
Gly Val Phe Trp Gly Tyr Ile Ser Leu Ile Glu Gly Leu Val Ala Arg
            195                 200                 205
Ile Lys Ala Glu Arg Gly Glu Pro Met Thr Val Ile Ala Thr Gly Gly
            210                 215                 220
Val Ala Ser Leu Phe Glu Gly Ala Thr Asp Ser Ile Asp His Phe Asp
225                 230                 235                 240
Ser Asp Leu Thr Ile Arg Gly Leu Leu Glu Ile Tyr Arg Arg Asn Thr
                245                 250                 255
Ile Ala Glu Ser
            260

<210> SEQ ID NO 52
<211> LENGTH: 783
<212> TYPE: DNA
<213> ORGANISM: Caulobacter crescentus

<400> SEQUENCE: 52
atgctgctgg ccattgagca gggcaacacc aacaccatgt tcgccattca tgatggcgca      60
tcgtgggtcg cgcagtggcg gtcagcgacc gaaagcacgc gcacggccga tgagtacgtc     120
gtctggcttt cgcaactgct gtcgatgcag gggcttggct ccgggcgat cgacgccgtg      180 atcatttcca gcgtcgtgcc gcagtcgatc ttcaatctgc gcaacctgag ccgccgctac     240
ttcaacgtcg agcctctggt catcggtgag aacgccaagc tgggcattga tgtccgcatc     300
gagaaaccct ccgaggccgg cgccgaccgc ctggtcaacg ccattggcgc ggcgatggtc     360
tatccgggtc gctggtcgt gatcgacagc ggcaccgcga cgacgttcga catcgtggcc     420
gccgacggcg ccttcgaggg cggattatc gcgcccggta tcaacctgtc gatgcaggct     480
ctgcacgagg cggcggcgaa gctgccgcgc atcgccatcc agcgtcccgc cggtaacagg     540
atcgtgggca cggacacggt ctccgccatg cagtccggcg tcttctgggg ctatatttcg     600
ctgatcgaag gcctcgtcgc gcggatcaag gccgagcgcg gcgagcctat gaccgttatc     660
gccacgggtg gcgtcgcctc gctgttcgag ggcgcgaccg acagcattga ccacttcgac     720
tctgatctga cgatccgggg tcttctcgaa atctaccgcc gaaacaccat cgccgagtcc     780
tga                                                                   783

<210> SEQ ID NO 53
<211> LENGTH: 257
<212> TYPE: PRT
<213> ORGANISM: Chlorobium tepidum

<400> SEQUENCE: 53

Met Arg Leu Val Val Asp Ile Gly Asn Thr Ser Thr Thr Leu Ala Ile
1               5                   10                  15

Phe Thr Gly Asp Glu Glu Pro Ser Val Glu Ser Val Pro Ser Ala Leu
            20                  25                  30

Phe Ala Asp Ser Ser Thr Met Arg Glu Val Phe Gly Asn Met Ala Arg
        35                  40                  45

Lys His Gly Glu Pro Gln Ala Ile Ala Ile Cys Ser Val Val Pro Ser
    50                  55                  60

Ala Thr Ala Val Gly Ser Ala Leu Leu Glu Ser Leu Phe Ser Val Pro
65                  70                  75                  80

Val Leu Thr Ile Cys Cys Lys Leu Arg Phe Pro Phe Arg Leu Asp Tyr
                85                  90                  95
```

```
Ala Thr Pro His Thr Phe Gly Ala Asp Arg Leu Ala Leu Cys Ala Trp
            100                 105                 110

Ser Arg His Leu Phe Ser Glu Lys Pro Val Ile Ala Val Asp Ile Gly
            115                 120                 125

Thr Ala Ile Thr Phe Asp Val Leu Asp Thr Val Gly Asn Tyr Arg Gly
            130                 135                 140

Gly Leu Ile Met Pro Gly Ile Asp Met Met Ala Gly Ala Leu His Ser
145                 150                 155                 160

Arg Thr Ala Gln Leu Pro Gln Val Arg Ile Asp Arg Pro Glu Ser Leu
                165                 170                 175

Leu Gly Arg Ser Thr Thr Glu Cys Ile Lys Ser Gly Val Phe Trp Gly
            180                 185                 190

Val Val Lys Gln Ile Gly Gly Leu Val Asp Ala Ile Arg Gly Asp Leu
            195                 200                 205

Val Arg Asp Phe Gly Glu Ser Thr Val Glu Val Ile Val Thr Gly Gly
            210                 215                 220

Asn Ser Arg Ile Ile Val Pro Glu Ile Gly Pro Val Ser Val Ile Asp
225                 230                 235                 240

Glu Leu Ala Val Leu Arg Gly Ser Asp Leu Leu Leu Arg Met Asn Met
                245                 250                 255

Pro

<210> SEQ ID NO 54
<211> LENGTH: 774
<212> TYPE: DNA
<213> ORGANISM: Chlorobium tepidum

<400> SEQUENCE: 54
gtgcggctgg tcgttgacat cggcaatacc agcacgacgt tggcgatttt caccggtgat    60
gaagagccgt cggtcgagtc ggtaccgagt gcgttgtttg ccgattccag cacaatgcgc   120
gaagtgtttg caacatggcc ccggaagcac ggcgagccac aggccatcgc catttgcagc   180
gtggtgcctt ccgctaccgc cgtcggttcg gcgcttctcg aatcacttt ctccgtaccg   240 gtgctgacca tctgctgtaa gctccgtttt cctttcgtc tcgactacgc aaccccgcac   300
accttcggcg cggatcgcct tgccctgtgc catggagcc gacatctctt ttctgaaaaa   360
ccggttatcg ccgtcgatat cggcacggcc atcaccttcg acgtgctcga cacggtgggg   420
aattatcgcg gtggtctcat catgccgggt atcgacatga tggccggagc gcttcattcg   480
agaaccgccc agcttcccca ggtgcgcatc gacaggccgg agagccttct cgggcgctcg   540
acgaccgaat gcatcaaaag cggagttttc tggggagtgg tcaaacagat cggcggcctc   600
gtggacgcca ttcgcggcga ccttgtacgc gactttggcg agtcaacggt cgaagtgatt   660
gtcaccggcg gcaatagcag gattatcgtt ccggagatcg gccctgtcag tgttatcgac   720
gaactcgctg tcctgcgcgg cagcgatctt ttgctgcgga tgaatatgcc gtga         774

<210> SEQ ID NO 55
<211> LENGTH: 256
<212> TYPE: PRT
<213> ORGANISM: Clostridium difficile

<400> SEQUENCE: 55

Met Leu Leu Val Phe Asp Val Gly Asn Thr Asn Met Val Leu Gly Ile
1               5                   10                  15

Tyr Lys Gly Asp Lys Leu Val Asn Tyr Trp Arg Ile Lys Thr Asp Arg
            20                  25                  30
```

Glu Lys Thr Ser Asp Glu Tyr Gly Ile Leu Ile Ser Asn Leu Phe Asp
                35                  40                  45

Tyr Asp Asn Val Asn Ile Ser Asp Ile Asp Asp Val Ile Ile Ser Ser
 50                  55                  60

Val Val Pro Asn Val Met His Ser Leu Glu Asn Phe Cys Ile Lys Tyr
 65                  70                  75                  80

Cys Lys Lys Gln Pro Leu Ile Val Gly Pro Gly Ile Lys Thr Gly Leu
                 85                  90                  95

Asn Ile Lys Tyr Asp Asn Pro Lys Gln Val Gly Ala Asp Arg Ile Val
                100                 105                 110

Asn Ala Val Ala Gly Ile Glu Lys Tyr Gly Ala Pro Ser Ile Leu Val
                115                 120                 125

Asp Phe Gly Thr Ala Thr Thr Phe Cys Ala Ile Ser Glu Lys Gly Glu
                130                 135                 140

Tyr Leu Gly Gly Thr Ile Ala Pro Gly Ile Lys Ile Ser Ser Glu Ala
145                 150                 155                 160

Leu Phe Gln Ser Ala Ser Lys Leu Pro Arg Val Glu Leu Ala Lys Pro
                165                 170                 175

Gly Met Thr Ile Cys Lys Ser Thr Val Ser Ala Met Gln Ser Gly Ile
                180                 185                 190

Ile Tyr Gly Tyr Val Gly Leu Val Asp Lys Ile Ser Ile Met Lys
                195                 200                 205

Lys Glu Leu Asn Cys Asp Asp Val Lys Val Ile Ala Thr Gly Gly Leu
210                 215                 220

Ala Lys Leu Ile Ala Ser Glu Thr Lys Ser Ile Asp Tyr Val Asp Gly
225                 230                 235                 240

Phe Leu Thr Leu Glu Gly Leu Arg Ile Ile Tyr Glu Lys Asn Gln Glu
                245                 250                 255

<210> SEQ ID NO 56
<211> LENGTH: 771
<212> TYPE: DNA
<213> ORGANISM: Clostridium difficile

<400> SEQUENCE: 56
atgcttctag tatttgatgt tggaaatact aatatggttt taggtatata taaaggtgac      60
aaattagtta attactggag aattaaaaca gatagggaaa aaacgtctga tgaatatgga     120
atcctgataa gtaacctatt tgattatgat aatgtgaata agtgatat tgatgatgtt     180
ataatatcat ctgtagttcc gaatgttatg cattctcttg aaaacttttg tataaagtac     240
tgtaaaaaac agccattaat agtaggtcca ggcataaaaa caggtctaaa tataaaatat     300
gataatccaa acaagttggg gcagataga atagttaatg ctgtagcagg atagaaaag     360
tatggagcac caagtatact tgttgatttt ggaacagcaa ctacattttg tgctatctct     420
gaaaaaggtg aatatttggg tggaacaata gcaccaggaa taaaaatatc tagtgaggcg     480
ttatttcaaa gtgcgtctaa attacctaga gtagaattag ctaagccagg tatgactatt     540
tgtaagagta ctgtatcagc catgcaatct ggaataattt atggatatgt tggtttagtt     600
gacaaaataa taagtattat gaagaaagaa ttgaattgtg atgatgttaa ggttatagct     660
acaggtggat tagctaaact gattgcttca gagacgaaaa gtatagatta tgtagatggt     720
tttttaacac tagaaggatt gagaataata tatgaaaaaa accaagaata a            771

<210> SEQ ID NO 57

```
<211> LENGTH: 219
<212> TYPE: PRT
<213> ORGANISM: Dehalococcoides ethenogenes

<400> SEQUENCE: 57

Met Ser Glu Lys Leu Val Ala Val Asp Ile Gly Asn Thr Ser Val Asn
1               5                   10                  15

Ile Gly Ile Phe Glu Gly Glu Lys Leu Leu Ala Asn Trp His Leu Gly
            20                  25                  30

Ser Val Ala Gln Arg Met Ala Asp Glu Tyr Ala Ser Leu Leu Leu Gly
        35                  40                  45

Leu Leu Gln His Ala Gly Ile His Pro Glu Glu Leu Asn Arg Val Ile
    50                  55                  60

Met Cys Ser Val Val Pro Pro Leu Thr Thr Thr Phe Glu Glu Val Phe
65                  70                  75                  80

Lys Ser Tyr Phe Lys Ala Ala Pro Leu Val Val Gly Ala Gly Ile Lys
                85                  90                  95

Ser Gly Val Lys Val Arg Met Asp Asn Pro Arg Glu Val Gly Ala Asp
            100                 105                 110

Arg Ile Val Asn Ala Ala Ala Ala Arg Val Leu Tyr Pro Gly Ala Cys
        115                 120                 125

Ile Ile Val Asp Met Gly Thr Ala Thr Thr Phe Asp Thr Leu Ser Glu
    130                 135                 140

Gly Gly Ala Tyr Ile Gly Gly Ala Ile Ala Pro Gly Ile Ala Thr Ser
145                 150                 155                 160

Ala Gln Ala Ile Ala Glu Lys Thr Ser Lys Leu Pro Lys Ile Glu Ile
                165                 170                 175

Ile Arg Pro Ala Lys Val Ile Gly Ser Asn Thr Val Ser Ala Met Gln
            180                 185                 190

Ser Gly Ile Tyr Phe Gly Tyr Ile Gly Leu Val Glu Glu Leu Val Arg
        195                 200                 205

Arg Ile Gln Thr Glu Leu Gly Gln Lys Thr Arg
    210                 215

<210> SEQ ID NO 58
<211> LENGTH: 659
<212> TYPE: DNA
<213> ORGANISM: Dehalococcoides ethenogenes

<400> SEQUENCE: 58
atgtctgaaa aactggtggc ggtagatatc ggcaatacca gcgtaaatat aggtatattt      60
gagggcgaaa aactgctggc aaactggcat ctgggttcgg ttgcccagcg tatggctgat     120
gaatatgcca gtctgctctt aggcctgttg cagcacgccg gtatacaccc ggaagagcta     180
aacagggtaa tcatgtgcag tgttgtgccg cccctgacca ctactttga agaggtattt     240 aaaagctatt tcaaggctgc tcctctggta gtgggtgcag gtataaagag cggggttaag     300
gtgcgcatgg ataacccccg tgaggttggg gctgaccgca tagtaaatgc cgctgccgcc     360
agggtgcttt atccggggc gtgcataata gtggacatgg gtacggccac tacctttgat     420 acccttttccg agggtggggc atatataggc ggggcgattg cacccggtat tgccacctca     480
gcccaggcta ttgcggaaaa gacttcaaaa ctgcccaaga ttgagataat ccgtcctgcc     540
aaagttatcg gctctaatac tgtgtcggct atgcagtcag gtatatactt cggttatatc     600
gggctggtgg aagagctggt caggcggatt caaactgaat tggggcagaa aaccagagt     659
```

<210> SEQ ID NO 59
<211> LENGTH: 212
<212> TYPE: PRT
<213> ORGANISM: Desulfovibrio vulgaris

<400> SEQUENCE: 59

```
Met Thr Gln His Phe Leu Leu Phe Asp Ile Gly Asn Thr Asn Val Lys
1               5                   10                  15

Ile Gly Ile Ala Val Glu Thr Ala Val Leu Thr Ser Tyr Val Leu Pro
            20                  25                  30

Thr Asp Pro Gly Gln Thr Thr Asp Ser Ile Gly Leu Arg Leu Leu Glu
        35                  40                  45

Val Leu Arg His Ala Gly Leu Gly Pro Ala Asp Val Gly Ala Cys Val
    50                  55                  60

Ala Ser Ser Val Val Pro Gly Val Asn Pro Leu Ile Arg Arg Ala Cys
65                  70                  75                  80

Glu Arg Tyr Leu Tyr Arg Lys Leu Leu Phe Ala Pro Gly Asp Ile Ala
                85                  90                  95

Ile Pro Leu Asp Asn Arg Tyr Glu Arg Pro Ala Glu Val Gly Ala Asp
            100                 105                 110

Arg Leu Val Ala Ala Tyr Ala Ala Arg Arg Leu Tyr Pro Gly Pro Arg
        115                 120                 125

Ser Leu Val Ser Val Asp Phe Gly Thr Ala Thr Thr Phe Asp Cys Val
    130                 135                 140

Glu Gly Gly Ala Tyr Leu Gly Gly Leu Ile Cys Pro Gly Val Leu Ser
145                 150                 155                 160

Ser Ala Gly Ala Leu Ser Ser Arg Thr Ala Lys Leu Pro Arg Ile Ser
                165                 170                 175

Leu Glu Val Glu Glu Asp Ser Pro Val Ile Gly Arg Ser Thr Thr Thr
            180                 185                 190

Ser Leu Asn His Gly Phe Ile Phe Gly Phe Ala Ala Met Thr Glu Gly
        195                 200                 205

Val Leu Ala Ala
    210
```

<210> SEQ ID NO 60
<211> LENGTH: 639
<212> TYPE: DNA
<213> ORGANISM: Desulfovibrio vulgaris

<400> SEQUENCE: 60

```
atgacccagc atttcctgct gttcgacatc ggcaacacca acgtcaagat cggcatcgcg      60
gtggaaaccg ccgtgctgac ttcgtacgtg ctgcccacag accccggcca gacgaccgac     120
tccatcgggc tgcgcctgct ggaggtgctg cgccatgccg gctgggaccg gcggacgtg     180
ggggcctgcg tggccagttc ggtggtgccc ggcgtcaacc cgctgatccg ccgcgcctgc     240
gaacgttacc tgtatcgcaa gctgctgttc gccccggcg acatcgccat tccgctggac     300
aaccgctacg aacggcccgc cgaagtgggc gcggaccggc tggtggcggc ctatgccgcc     360
cggcggctgt accccggccc ccggtcgctg gtatccgtgg atttcggcac cgccaccacg     420
tttgactgcg tggaagggg tgcgtatctt ggtggtttga tctgtcccgg cgtgctgtcg     480
tccgccgggg cgttgtcgtc gcgcacggcc aagctgccgc gcatcagtct ggaagtggaa     540
gaggattcgc cggtcatcgg cggtccacc accaccagcc tgaaccacgg cttcatttc     600
ggctttgccg ccatgaccga aggggtgctg gccgcctga                           639
```

<210> SEQ ID NO 61
<211> LENGTH: 249
<212> TYPE: PRT
<213> ORGANISM: Pseudomonas putida

<400> SEQUENCE: 61

Met Ile Leu Glu Leu Asp Cys Gly Asn Ser Phe Ile Lys Trp Arg Val
1               5                   10                  15

Ile His Val Ala Asp Ala Val Ile Glu Gly Gly Ile Val Asp Ser
                20                  25                  30

Asp Gln Ala Leu Val Ala Glu Val Ala Ala Leu Ala Ser Val Arg Leu
        35                  40                  45

Thr Gly Cys Arg Ile Val Ser Val Arg Ser Glu Glu Thr Asp Ala
    50                  55                  60

Leu Cys Ala Leu Ile Ala Gln Ala Phe Ala Val Gln Ala Lys Val Ala
65                  70                  75                  80

His Pro Val Arg Glu Met Ala Gly Val Arg Asn Gly Tyr Asp Asp Tyr
                85                  90                  95

Gln Arg Leu Gly Met Asp Arg Trp Leu Ala Ala Leu Gly Ala Phe His
            100                 105                 110

Leu Ala Lys Gly Ala Cys Leu Val Ile Asp Leu Gly Thr Ala Ala Lys
        115                 120                 125

Ala Asp Phe Val Ser Ala Asp Gly Glu His Leu Gly Gly Tyr Ile Cys
    130                 135                 140

Pro Gly Met Pro Leu Met Arg Ser Gln Leu Arg Thr His Thr Arg Arg
145                 150                 155                 160

Ile Arg Tyr Asp Asp Ala Ser Ala Glu Arg Ala Leu Ser Ser Leu Ser
                165                 170                 175

Pro Gly Arg Ser Thr Val Glu Ala Val Glu Arg Gly Cys Val Leu Met
            180                 185                 190

Leu Gln Gly Phe Ala Tyr Thr Gln Leu Glu Gln Ala Arg Val Leu Trp
        195                 200                 205

Gly Glu Glu Phe Thr Val Phe Leu Thr Gly Gly Asp Ala Pro Leu Val
    210                 215                 220

Arg Ala Ala Leu Pro Gln Ala Arg Val Val Pro Asp Leu Val Phe Val
225                 230                 235                 240

Gly Leu Ala Met Ala Cys Pro Leu Asp
                245

<210> SEQ ID NO 62
<211> LENGTH: 750
<212> TYPE: DNA
<213> ORGANISM: Pseudomonas putida

<400> SEQUENCE: 62
atgattcttg agctcgattg cggtaacagc ttcatcaagt ggcgggtgat ccatgttgcc    60
gatgctgtga ttgaaggtgg tgggatcgtc gattccgatc aggcgctggt ggcggaagtg   120
gctgcgctcg cttcagtgcg tctcacgggt tgccgtattg tcagtgtgcg cagcgaagaa   180
gagaccgatg cgctttgcgc gttgattgct caggcatttg ccgtgcaggc gaaggttgcc   240
caccctgtcc gtgaaatggc aggtgtgcgc aatggctatg acgactatca gcgcctgggt   300
atggatcgtt ggctggcggc gttgggggca tttcacctgg ccaagggcgc gtgcctggtg   360
attgacctgg gtaccgcggc aaaagcggac ttcgtttctg cagatggcga gcatcttggg   420
ggctacatct gcccaggtat gccattgatg cgtagccagc tgcgcactca cacccgtcgg   480

```
atccgctatg acgatgcctc cgcggagcgc gcattgagca gcttgtcacc aggtcgctcg      540
actgtcgaag cggtagagcg cggttgcgta ttgatgctcc agggctttgc ctacacccag      600
cttgagcagg ctcgtgtgct atggggtgag gagttcaccg tgttcctcac tggcggtgat      660
gcgccactgg tgagggcggc cctgccacag gcgcgggtcg tgcctgacct ggttttcgtt      720
ggcctggcaa tggcttgtcc attggattga                                       750
```

<210> SEQ ID NO 63
<211> LENGTH: 241
<212> TYPE: PRT
<213> ORGANISM: Thiobacillus ferrooxidans

<400> SEQUENCE: 63

```
Met Ile Phe Ile Ala Val Gly Asn Thr Arg Thr Leu Leu Ala His Thr
1               5                   10                  15

His Asp Gly Val His Phe Asp Ser Val Ser Val Ala Thr Ser Leu Pro
            20                  25                  30

Pro Thr Glu Ile Leu Gln Gln Pro Gly Leu Thr Trp Leu Ser Ala Pro
        35                  40                  45

Asn Arg Glu Pro Val Ala Leu Gly Gly Val Val Pro Ala Ala Leu Ala
    50                  55                  60

Ala Trp Arg Glu Ala Leu Ala Thr Ala Glu Val Arg Glu Pro Asp Pro
65                  70                  75                  80

Gly Phe Phe Arg Arg Ala Val Pro His Asp Tyr His Pro Pro Glu Ser
                85                  90                  95

Leu Gly Phe Asp Arg Arg Cys Cys Leu Leu Ala Ala Ala Met Asp Tyr
            100                 105                 110

Pro Gly Gln Asp Ser Ile Val Ile Asp Met Gly Thr Ala Ile Thr Ile
        115                 120                 125

Asp Leu Leu Ala Gly Gly His Phe Arg Gly Gly Arg Ile Leu Pro Gly
    130                 135                 140

Ile Ala Met Ser Leu Arg Gly Leu His Glu Gly Thr Ala Leu Leu Pro
145                 150                 155                 160

Glu Val Val Leu Asn Ala Pro Ala Glu Met Leu Gly Asn Asp Thr Ser
                165                 170                 175

Asn Ala Ile Gln Ala Gly Val Ile His Leu Phe Ala Asp Ala Leu Arg
            180                 185                 190

Gly Ala Ile Thr Asp Phe Arg Gln Tyr Ser Pro Gln Ala Arg Ile Leu
        195                 200                 205

Ile Thr Gly Gly Asp Ala Glu Arg Trp Gln Pro Gly Ile Ala Gly Ser
    210                 215                 220

Leu Tyr Gln Pro His Leu Leu Leu Arg Gly Phe Tyr Leu Trp Ile Arg
225                 230                 235                 240

Gly
```

<210> SEQ ID NO 64
<211> LENGTH: 726
<212> TYPE: DNA
<213> ORGANISM: Thiobacillus ferrooxidans

<400> SEQUENCE: 64

```
atgatcttca tcgccgtcgg caataccgc accctgctgg cacacaccca cgatggcgtg      60
catttcgaca gcgtcagcgt ggccacttcg ctgccaccca cggaaatcct gcagcagccc     120
ggcttgacat ggctcagcgc gccgaaccgg gaacccgtcg cgctgggcgg cgtcgtacct     180
```

-continued

```
gcggcgcttg ccgcctggcg ggaagccttg gccacggcag aggtccgcga acccgacccc    240
ggcttttttc gccgcgccgt gccgcacgac tatcatccgc cggaaagcct cggctttgac    300
cgccgttgct gcctgctcgc cgccgccatg gactaccccg gccaggacag catcgtcatc    360
gacatgggca ccgccatcac catcgacctg ctggctggcg gacatttccg gggcggacgc    420
attctgccgg gtatcgccat gagcctgcgc ggtctgcatg aaggcacggc actccttcct    480
gaagtcgtcc tgaacgcccc agcggaaatg ctgggcaatg acaccagcaa cgccattcag    540
gccggggtca tccacctctt tgccgatgcc ctgcgcggcg ccattaccga ctttcgccag    600
tacagccccc aggcacggat actgatcacc ggtggcgatg ccgaacgttg gcaacccggc    660
atcgctggta gcctgtacca gccccatctg cttctgcgcg gcttttatct gtggatacgg    720
ggatga                                                                726
```

<210> SEQ ID NO 65
<211> LENGTH: 242
<212> TYPE: PRT
<213> ORGANISM: Xylessa fastidiosa

<400> SEQUENCE: 65

```
Met Asn Asp Trp Leu Phe Asp Leu Gly Asn Ser Arg Phe Lys Cys Ala
1               5                   10                  15

Ser Leu Arg Glu Gly Val Ile Gly Pro Val Thr Val Leu Pro Tyr Leu
            20                  25                  30

Thr Glu Thr Met Asp Ala Phe Ala Leu Gln Glu Leu Pro Arg Gly Arg
        35                  40                  45

Val Ala Tyr Leu Ala Ser Val Ala Ala Pro Ala Ile Thr Thr His Val
    50                  55                  60

Leu Glu Val Leu Lys Ile His Phe Glu Gln Val Gln Val Ala Ala Thr
65                  70                  75                  80

Val Ala Ala Cys Ala Gly Val Arg Ile Ala Tyr Ala His Pro Glu Arg
                85                  90                  95

Phe Gly Val Asp Arg Phe Leu Ala Leu Leu Gly Ser Tyr Gly Glu Gly
            100                 105                 110

Asn Val Leu Val Val Gly Val Gly Thr Ala Leu Thr Ile Asp Leu Leu
        115                 120                 125

Ala Ala Asn Gly Cys His Leu Gly Gly Arg Ile Ser Ala Ser Pro Thr
    130                 135                 140

Leu Met Arg Gln Ala Leu His Ala Arg Ala Glu Gln Leu Pro Leu Ser
145                 150                 155                 160

Gly Gly Asn Tyr Leu Glu Phe Ala Glu Asp Thr Glu Asp Ala Leu Val
                165                 170                 175

Ser Gly Cys Asn Gly Ala Ala Val Ala Leu Ile Glu Arg Ser Leu Tyr
            180                 185                 190

Glu Ala His Gln Arg Leu Asp Gln Ser Val Arg Leu Leu Leu His Gly
        195                 200                 205

Gly Gly Val Ala Ser Leu Leu Pro Trp Leu Gly Asp Val Val His Arg
    210                 215                 220

Pro Thr Leu Val Leu Asp Gly Leu Ala Ile Trp Ala Ala Val Ala Ala
225                 230                 235                 240

Asn Val
```

<210> SEQ ID NO 66
<211> LENGTH: 729

-continued

<212> TYPE: DNA
<213> ORGANISM: Xylella fastidiosa

<400> SEQUENCE: 66
atgaatgatt ggttattcga tctaggtaat tcgcgtttta aatgtgcatc gctcagggaa 60
ggtgtgattg gtcctgtaac ggttttgccg tacttaacag agaccatgga cgcgtttgcg 120
ttacaggagc taccacgtgg tcgtgtggct tacttggcga gtgtcgctgc tccggctatt 180
actacacatg tgctcgaagt attaaaaatc cacttcgagc aagtccaggt ggctgcaacc 240
gtcgctgcat gtgccggagt acgaattgcc tatgctcacc cggaacgttt tggagtggat 300
aggttcttag cgttgcttgg ttcgtatggt gagggcaatg tcctggtagt gggtgtcggg 360
acagcattga ctattgattt gttggctgcc aatggttgtc atctcggagg gcgtatcagt 420
gcttcaccga cattgatgcg ccaagcgttg catgcacgcg cggagcaact ccccctcagt 480
ggtgggaact acttggagtt tgcggaagat acagaggatg cgttggtgtc agggtgcaat 540
ggtgcagcgg tggcattgat cgaacgtagc ctgtatgagg cacatcaacg tttggaccag 600
tcggttcgat tattgttgca tggtggaggt gtagcatctt tattgccttg gttgggcgac 660
gtggtacatc gtcctacatt agtattggat ggcctggcga tctgggctgc cgttgcagct 720
aacgtttag 729

<210> SEQ ID NO 67
<211> LENGTH: 223
<212> TYPE: PRT
<213> ORGANISM: Helicobacter pylori

<400> SEQUENCE: 67

Met Pro Ala Arg Gln Ser Phe Thr Asp Leu Lys Asn Leu Val Leu Cys
1 5 10 15

Asp Ile Gly Asn Thr Arg Ile His Phe Ala Gln Asn Tyr Gln Leu Phe
20 25 30

Ser Ser Ala Lys Glu Asp Leu Lys Arg Leu Gly Ile Gln Lys Glu Ile
35 40 45

Phe Tyr Ile Ser Val Asn Glu Glu Asn Glu Lys Ala Leu Leu Asn Cys
50 55 60

Tyr Pro Asn Ala Lys Asn Ile Ala Gly Phe Phe His Leu Glu Thr Asp
65 70 75 80

Tyr Val Gly Leu Gly Ile Asp Arg Gln Met Ala Cys Leu Ala Val Asn
85 90 95

Asn Gly Val Val Val Asp Ala Gly Ser Ala Ile Thr Ile Asp Leu Ile
100 105 110

Lys Glu Gly Lys His Leu Gly Gly Cys Ile Leu Pro Gly Leu Ala Gln
115 120 125

Tyr Ile His Ala Tyr Lys Lys Ser Ala Lys Ile Leu Glu Gln Pro Phe
130 135 140

Lys Ala Leu Asp Ser Leu Glu Val Leu Pro Lys Ser Thr Arg Asp Ala
145 150 155 160

Val Asn Tyr Gly Met Val Leu Ser Val Ile Ala Cys Ile Gln His Leu
165 170 175

Ala Lys Asn Gln Lys Ile Tyr Leu Cys Gly Gly Asp Ala Lys Tyr Leu
180 185 190

Ser Ala Phe Leu Pro His Ser Val Cys Lys Glu Arg Leu Val Phe Asp
195 200 205

Gly Met Glu Ile Ala Leu Lys Lys Ala Gly Ile Leu Glu Cys Lys

<210> SEQ ID NO 68
<211> LENGTH: 672
<212> TYPE: DNA
<213> ORGANISM: Helicobacter pylori

<400> SEQUENCE: 68

| | | | | | |
|---|---|---|---|---|---|
| atgccagcta | ggcaatcttt | tacagatttg | aaaaacctgg | ttttgtgcga | tataggcaac | 60 |
| acgcgtatcc | attttgcaca | aaactatcag | ctcttttcaa | gcgctaaaga | agatttaaag | 120 |
| cgtttgggta | ttcaaaagga | aatttttttac | attagcgtga | atgaagaaaa | tgaaaaagcc | 180 |
| cttttgaatt | gttaccctaa | cgctaaaaat | attgcagggt | ttttttcattt | agaaaccgac | 240 |
| tatgtagggc | ttgggataga | ccggcaaatg | gcgtgtctgg | cggtaaataa | tggcgtggtg | 300 |
| gtggatgccg | ggagtgcgat | tacgatagat | ttaatcaaag | agggcaagca | tttaggaggg | 360 |
| tgtattttac | ccggtttagc | ccaatatatt | catgcgtata | aaaaaagcgc | taaaatttta | 420 |
| gagcaaccct | tcaaggcctt | agattcttta | gaagttttac | ctaaaagcac | tagagacgct | 480 |
| gtgaattacg | gcatggtttt | gagcgtcatt | gcttgtatcc | agcatttagc | caaaaatcaa | 540 |
| aaaatctatc | tttgtggggg | cgatgcgaag | tatttgagcg | cgttttttacc | ccattctgtt | 600 |
| tgcaaggagc | gtttggtttt | tgacgggatg | gaaatcgctc | ttaaaaaagc | agggatacta | 660 |
| gaatgcaaat | ga | | | | | 672 |

<210> SEQ ID NO 69
<211> LENGTH: 750
<212> TYPE: DNA
<213> ORGANISM: Pseudomonas syringae

<400> SEQUENCE: 69

| | | | | | |
|---|---|---|---|---|---|
| atgattcttg | agctcgattg | cggcaacagc | tttatcaagt | ggcggataat | cacaaagagt | 60 |
| tgctcaacgt | tggtcagcgg | cggagtagtg | gactcggaca | cagccttgct | agagtgcctg | 120 |
| ggcaatctgt | caggcgcagc | attcagcgat | tgccgtctgg | taagcgttcg | tagcgcggaa | 180 |
| gaaacggcga | agctggtttg | cgcgctggca | gataccttt | ccattagccc | tgtctgtgca | 240 |
| gcgccggcgc | cagagcttgc | cggggtaatc | aatggatacg | acgattttgc | acgcttgggg | 300 |
| ctggatcgct | ggttggcatt | tgtagggggct | taccaccttg | ttaagggtgc | ctgcctggtg | 360 |
| atcgatctgg | gcaccgccat | tacgtctgac | tttgttgaag | cgtcaggaaa | gcatctgggt | 420 |
| ggtttcatct | gtcctggcat | gccactgatg | cgcaatcagc | tgcgtaccca | cacccgtcgc | 480 |
| attcgatatg | acgatgcaga | ggctgaaaaa | gccctggtac | gactcgtgcc | tggccgtgcg | 540 |
| acggccgagg | ctgtggagcg | aggttgttct | ctcatgcttc | gcggattcgc | aatgactcag | 600 |
| atcgagatag | ctcgcgaata | ctgggggggac | gactttgcta | ttttcgtgac | aggaggcgac | 660 |
| gctgtcttgg | ttgctgatgt | gttaccgggc | gctcgcattg | tccctgattt | ggtattcgtt | 720 |
| ggcctggctc | tcgcttgccc | tttacgttga | | | | 750 |

<210> SEQ ID NO 70
<211> LENGTH: 249
<212> TYPE: PRT
<213> ORGANISM: Pseudomonas syringae

<400> SEQUENCE: 70

Met Ile Leu Glu Leu Asp Cys Gly Asn Ser Phe Ile Lys Trp Arg Ile
1               5                   10                  15

```
Ile Thr Lys Ser Cys Ser Thr Leu Val Ser Gly Gly Val Val Asp Ser
            20                  25                  30

Asp Thr Ala Leu Leu Glu Cys Leu Gly Asn Leu Ser Gly Ala Ala Phe
            35                  40                  45

Ser Asp Cys Arg Leu Val Ser Val Arg Ser Ala Glu Glu Thr Ala Lys
 50                  55                  60

Leu Val Cys Ala Leu Ala Asp Thr Phe Ser Ile Ser Pro Val Cys Ala
 65                  70                  75                  80

Ala Pro Ala Pro Glu Leu Ala Gly Val Ile Asn Gly Tyr Asp Asp Phe
                 85                  90                  95

Ala Arg Leu Gly Leu Asp Arg Trp Leu Ala Phe Val Gly Ala Tyr His
            100                 105                 110

Leu Val Lys Gly Ala Cys Leu Val Ile Asp Leu Gly Thr Ala Ile Thr
            115                 120                 125

Ser Asp Phe Val Glu Ala Ser Gly Lys His Leu Gly Phe Ile Cys
            130                 135                 140

Pro Gly Met Pro Leu Met Arg Asn Gln Leu Arg Thr His Thr Arg Arg
145                 150                 155                 160

Ile Arg Tyr Asp Asp Ala Glu Ala Glu Lys Ala Leu Val Arg Leu Val
            165                 170                 175

Pro Gly Arg Ala Thr Ala Glu Ala Val Glu Arg Gly Cys Ser Leu Met
            180                 185                 190

Leu Arg Gly Phe Ala Met Thr Gln Ile Glu Ile Ala Arg Glu Tyr Trp
            195                 200                 205

Gly Asp Asp Phe Ala Ile Phe Val Thr Gly Gly Asp Ala Val Leu Val
            210                 215                 220

Ala Asp Val Leu Pro Gly Ala Arg Ile Val Pro Asp Leu Val Phe Val
225                 230                 235                 240

Gly Leu Ala Leu Ala Cys Pro Leu Arg
            245

<210> SEQ ID NO 71
<211> LENGTH: 8320
<212> TYPE: DNA
<213> ORGANISM: Artificial Sequence
<220> FEATURE:
<223> OTHER INFORMATION: Description of Artificial Sequence: plasmid,
      pAN296

<400> SEQUENCE: 71
tgcgccgcta cagggcgcgt ccattcgcca ttcaggctgc gcaactgttg ggaagggcga      60
tcggtgcggg cctcttcgct attacgccag ctggcgaaag ggggatgtgc tgcaaggcga     120
ttaagttggg taacgccagg gttttcccag tcacgacgtt gtaaaacgac ggccagtgaa     180
ttgtaatacg actcactata gggcgaattg gcccgacgt cgcatgctgg atgaaaagcc      240
gatgaccgct tttcaggtct gtcagcagct ttttcctgct gtatatgaaa aggaattgtt     300
tttaacgatg tcagaaacgg caggtcacct tgatgtgttg gaggctgaag aagccatcac     360
gtcatattgg gaaggaaata ccgtatactt taaaacaatg aagaggtgaa atgggtgaaa     420
catatagcgg gaaaaaggat ttggataacc ggcgcttcag gagggcttgg agaaagaatc     480
gcatacttat gcgcggctga aggagcccat gtcctgctgt cggctagacg cgaggatcgt     540
ttgatagaaa tcaaaaggaa aataaccgag gaatggagcg acagtgtga  gattttttcct   600 ctggatgtcg gccgcctaga ggatatcgcc cgggtccgcg atcagatcgg ctcgattgat     660
gtactgatta acaatgcagg cttcggtata tttgaaacgg ttttagactc tacattggat     720
```

```
gacatgaaag cgatgtttga tgtgaatgtc ttcggcctga tcgcctgtac aaaagcggtg      780
cttccgcaaa tgcttgagca aaaaaaggga catatcatca atatcgcctc tcaagcgggg      840
aaaatcgcca caccgaagtc tagcctgtat tccgcgacca acatgccgt gttaggttac       900 tcaaacgctt tgcggatgga gctttcggga accggcattt atgtgacaac agtcaacccg      960
ggcccgattc agacggactt ttttccatt gctgataaag cggggacta cgccaaaaat       1020 gtcggccgct ggatgcttga tcctgatgac gtggcagctc aaattacagc tgcaattttt     1080
acgaaaaagc gggagatcaa tcttccgcgt taatgaatg ccggcactaa gctgtatcag      1140
ctgtttccag ctcttgtaga aaagctggca ggacgcgcgc tcatgaaaaa ataatgatag     1200
aactgcctgt ggtggagtgg cttgtttctc acggggcagt ttttgatagt ggaagggaga    1260
gattgttgaa tgtcagttca ttcagaagtc cttcatgctc tgcttaaaga tccgtttatt    1320
cagaaactga ttgatgcaga gcctgtattc tgggcaaatt caggcaagaa agaggggcca   1380
ttaccccgtg cagatgagtg ggcaaccgag atagcggaag cggaaaaaag aatgcagcgg   1440
tttgcacctt acattgccga ggtgtttcct gagacgaaag gcgctaaagg aatcatcgag   1500
tctccgcttt ttgaggtgca gcatatgaag ggaaagctgg aagcggcata tcagcagcca   1560
tttcccggaa gatggctttt aaagtgcgac catgagcttc cgatttcagg atcgattaaa   1620
gcgaggggcg ggatttatga agtgttaaag tatgctgaaa atctcgcgct tcaagaagga   1680
atgcttcagg aaaccgatga ttaccgcatc ttacaggaag agcggtttac cgggtttttc   1740
tcccgctatt cgattgctgt cggttcgaca ggaaatctag gtttaagcat cggcatcatc   1800
ggcgcggcac tcgggtttcg cgtgacagtg catatgtccg ccgatgctaa gcagtggaaa   1860
aaggatctcc tccgccaaaa gggagtcact gttatggagt acgaaacaga ttacagtgaa   1920
gcggtgaacg aagggagacg gcaggcggaa caagatccat tctgttattt tattgatgat   1980
gaacattctc gtcagctgtt cttaggatat gctgttgctg caagccgatt aaaaacacag   2040
cttgactgta tgaatataaa gccaagtctt gagacgccct tgtttgtgta tctgccgtgc   2100
ggagtcggcg gaggaccggg cggtgtagca tttgggctga agcttttata cggagatgat   2160
gttcatgtgt ttttcgcaga accaactcat tcaccttgta tgctgttagg gctttattca   2220
ggacttcacg agaagatctc cgtccaggat atcggcctgg ataatcagac ggctgctgac   2280
ggacttgccg tagggaggcc gtcaggattt gtcggcaagc tgattgaacc gcttctgagc   2340
ggctgttata cggtagagga caatacgctt tatactttgc ttcatatgct ggctgtatct   2400
gaagataaat atttagagcc ctctgctctt gctggcatgt tcgggccggt tcagcttttt   2460
tcgacagaag agggaaggcg ctatgctcag aaatataaga tggaacatgc cgtacatgtc   2520
gtctggggaa cgggaggaag catggttcca aaagatgaaa tggctgcgta taccgaatc    2580 ggtgctgatt tgctaaaaaa acgaaatgga aaataagcag acagtgaaaa ggttttccgt   2640
tacaatcttt gtaagggttt taacctacag agagtcaggt gtaaacagtg aaaaataaag   2700 aacttaaccct acatacttta tatacacagc acaatcggga gtcttctgca gctcgagcaa   2760
tagttaccct tattatcaag ataagaaaga aaaggatttt tcgctacgct caaatccttt   2820
aaaaaaacac aaaaagaccac attttttaat gtggtcttta ttcttcaact aaagcaccca   2880
ttagttcaac aaacgaaaat tggataaagt gggatatttt taaaatatat atttatgtta   2940
cagtaatatt gacttttaaa aaaggattga ttctaatgaa gaaagcagac aagtaagcct   3000
cctaaattca ctttagataa aaatttagga ggcatatcaa atgaacttta ataaaattga   3060
```

```
tttagacaat tggaagagaa aagagatatt taatcattat ttgaaccaac aaacgactttt    3120 tagtataacc acagaaattg atattagtgt tttataccga aacataaaac aagaaggata     3180
taaattttac cctgcattta ttttcttagt gacaagggtg ataaactcaa atacagcttt     3240
tagaactggt tacaatagcg acggagagtt aggttattgg gataagttag agccactttta   3300 tacaatttt gatggtgtat ctaaaacatt ctctggtatt tggactcctg taaagaatga     3360
cttcaaagag ttttatgatt tatacctttc tgatgtagag aaatataatg gttcggggaa    3420
attgttcccc aaaacaccta acctgaaaa tgcttttttct ctttctatta ttccatggac    3480
ttcatttact gggtttaact taaatatcaa taataatagt aattaccttc tacccattat    3540
tacagcagga aaattcatta ataaaggtaa ttcaatatat ttaccgctat ctttacaggt    3600
acatcattct gtttgtgatg gttatcatgc aggattgttt atgaactcta ttcaggaatt    3660
gtcagatagg cctaatgact ggcttttata atatgagata atgccgactg tacttttttac   3720 agtcggtttt ctaatgtcac taacctgccc cgttagttga agaaggtttt tatattacag    3780
ctgtcgacta aggtcgagga agtgttggta aggagggtat gaaatgtgca tcatattgaa    3840
ctgtatgtct ctgatttgga ggcgtctagg cggttttggg gctggttctt aaaagaactt    3900
ggttataaag agtatcaaaa atggagctca ggcatcagct ggaagaaaga tcgttttac    3960 ctagtgattg tgcaggcgaa agagccattt ctagagccgg aataccatag atgccgagtc    4020
ggtctgaacc atctcgcatt tcatgctgaa tccaagcttc aagtcgatca gatgactgaa    4080
aaattgacgg caaaaggcta tcgtgtgttg taccgagaca ggcatccttt tgccggagga    4140
gacgggcatt atgcagtctt ttgtgaggat ccagaccgga ttaaggtaga gctcgttgcc    4200
ccaagctgtt aatcgtgatc ttcggacagg ctgttcagct ttttctcaat gcgatccagc    4260
tgcgcttttc ggttttttcgc atacttgaag cctgtaacag ccgcaaagac gacagcggca    4320
aatataataa atacaaacag ctgaaacatc acatcaccta tattcatgtt cttcacctca    4380
tgtttgcggg agagattcat tctcttccgt tttttattta aagcggctttt tccagacggg   4440 aacggtgttt tgtggtctcc atttttcattt gccgataggc gaacgctaaa aatggcaggc    4500
cgagcagggt aatgccgctc aggacagaaa aaatataaat cggccggcca gcgccaaaca    4560
ggtctataca tatcccccccg acccaagggc cgatgacgtt tccgagctgt ggaaaaccga    4620
ttgccccgaa ataagtgcct tttaatcctg gttttgcaat ctggtctaca tacaaatcca    4680
tcatagagaa taaaagcact tcgccgattg taaatgtgat gacaatcatc acaattgatg    4740
gaacaccgtg tgatacggtg aaaatggcca tgctgatgct aaccatcaca ttaccgagca    4800
tcagagaaca aagcggcgaa aaccgttttg caaaatggac aatgggaaat tgcgtcgcca    4860
acacaacgat tgcgttaat gtcagcatca gcccatacag cttcgttcca ttgccgatca    4920 agggggttctg cgccatatac tgagggaatg tggaactgaa ttgtgagtag ccgaaggtgc    4980
atagcgtaat gccgaccaaa gcaatggtaa aaagataatc cttttgcgtg accataaacg    5040
cttcccgcac gctcatattt cgggactggg ctggtgctga taaggatgga tgttttttaa    5100
attggagggc aagcacaatt ccgtatagtc cgtaaatgac tgcaggcacc aaaaagggcg    5160
tagtcgattg cgatgagccg aaatataggc caagcacagg tccgaagaca acgccgatat    5220
taatagccgc atagcgtaaa ttaaaaacta gcagtctcgt ttttttcttct gtcatatcag    5280 acaacaaggc ctttgaagcg ggctcaaaca gtgatttgca aagaccgttt aatgcgttta    5340
ctacaaaaaa cacccagaga ttagatgctg ccgcaaagcc tgcaaatacc agcatccatc    5400
cgaaaatcga tacaagcatc atgtttttc tgccgaattt atctgagata tatccgccgt    5460
```

```
aaaagcttgc gaggatgccg actgatgagc tcgcggcgat gaccagccct gcataggaag    5520
ctgatgcgcc ttggacggct gtcaaataaa tcgctaaaaa aggaatgctc atcgatgttg    5580
ccattctgcc gaaaatggtt ccgattataa ttgtaacgcg ttggatgcat agcttgagta    5640
ttctatagtg tcacctaaat agcttggcgt aatcatggtc atagctgttt cctgtgtgaa    5700
attgttatcc gctcacaatt ccacacaaca tacgagccgg aagcataaag tgtaaagcct    5760
ggggtgccta atgagtgagc taactcacat taattgcgtt gcgctcactg cccgctttcc    5820
agtcgggaaa cctgtcgtgc cagctgcatt aatgaatcgg ccaacgcgcg gggagaggcg    5880
gtttgcgtat tgggcgctct tccgcttcct cgctcactga ctcgctgcgc tcggtcgttc    5940
ggctgcggcg agcggtatca gctcactcaa aggcggtaat acggttatcc acagaatcag    6000
gggataacgc aggaaagaac atgtgagcaa aaggccagca aaaggccagg aaccgtaaaa    6060
aggccgcgtt gctggcgttt ttcgataggc tccgccccc tgacgagcat cacaaaaatc    6120
gacgctcaag tcagaggtgg cgaaacccga caggactata aagataccag gcgtttcccc    6180
ctggaagctc cctcgtgcgc tctcctgttc cgaccctgcc gcttaccgga tacctgtccg    6240
cctttctccc ttcgggaagc gtggcgcttt ctcatagctc acgctgtagg tatctcagtt    6300
cggtgtaggt cgttcgctcc aagctgggct gtgtgcacga accccccgtt cagcccgacc    6360
gctgcgcctt atccggtaac tatcgtcttg agtccaaccc ggtaagacac gacttatcgc    6420
cactggcagc agccactggt aacaggatta gcagagcgag gtatgtaggc ggtgctacag    6480
agttcttgaa gtggtggcct aactacggct acactagaag gacagtattt ggtatctgcg    6540
ctctgctgaa gccagttacc ttcggaaaaa gagttggtag ctcttgatcc ggcaaacaaa    6600
ccaccgctgg tagcggtggt ttttttgttt gcaagcagca gattacgcgc agaaaaaaag    6660
gatctcaaga agatccttg atcttttcta cggggtctga cgctcagtgg aacgaaaact    6720
cacgttaagg gattttggtc atgagattat caaaaaggat cttcacctag atccttttaa    6780
attaaaaatg aagttttaaa tcaatctaaa gtatatatga gtaaacttgg tctgacagtt    6840
accaatgctt aatcagtgag gcacctatct cagcgatctg tctatttcgt tcatccatag    6900
ttgcctgact ccccgtcgtg tagataacta cgatacggga gggcttacca tctggcccca    6960
gtgctgcaat gataccgcga acccacgct caccggctcc agatttatca gcaataaacc    7020
agccagccgg aagggccgag cgcagaagtg gtcctgcaac tttatccgcc tccatccagt    7080
ctattaattg ttgccgggaa gctagagtaa gtagttcgcc agttaatagt ttgcgcaacg    7140
ttgttggcat tgctacaggc atcgtggtgt cacgctcgtc gtttggtatg gcttcattca    7200
gctccggttc ccaacgatca aggcgagtta catgatcccc catgttgtgc aaaaaagcgg    7260
ttagctcctt cggtcctccg atcgttgtca gaagtaagtt ggccgcagtg ttatcactca    7320
tggttatggc agcactgcat aattctctta ctgtcatgcc atccgtaaga tgcttttctg    7380
tgactggtga gtactcaacc aagtcattct gagaataccg cgcccggcga ccgagttgct    7440
cttgcccggc gtcaatacgg gataatagtg tatgacatag cagaaccttta aaagtgctca    7500 tcattggaaa acgttcttcg gggcgaaaac tctcaaggat cttaccgctg ttgagatcca    7560
gttcgatgta acccactcgt gcacccaact gatcttcagc atcttttact ttcaccagcg    7620
tttctgggtg agcaaaaaca ggaaggcaaa atgccgcaaa aaagggaata agggcgacac    7680
ggaaatgttg aatactcata ctcttccttt ttcaatatta ttgaagcatt tatcagggtt    7740
attgtctcat gagcggatac atatttgaat gtatttagaa aaataaacaa ataggggttc    7800
```

```
cgcgcacatt tccccgaaaa gtgccacctg tatgcggtgt gaaataccgc acagatgcgt      7860
aaggagaaaa taccgcatca ggcgaaattg taaacgttaa tattttgtta aaattcgcgt      7920
taaatatttg ttaaatcagc tcatttttta accaataggc cgaaatcggc aaaatccctt      7980
ataaatcaaa agaatagacc gagatagggt tgagtgttgt tccagtttgg aacaagagtc      8040
cactattaaa gaacgtggac tccaacgtca aagggcgaaa aaccgtctat cagggcgatg      8100
gcccactacg tgaaccatca cccaaatcaa gttttttgcg gtcgaggtgc cgtaaagctc      8160
taaatcggaa ccctaaaggg agcccccgat ttagagcttg acggggaaag ccggcgaacg      8220
tggcgagaaa ggaagggaag aaagcgaaag gagcgggcgc tagggcgctg gcaagtgtag      8280
cggtcacgct gcgcgtaacc accacacccg ccgcgcttaa                            8320

<210> SEQ ID NO 72
<211> LENGTH: 6688
<212> TYPE: DNA
<213> ORGANISM: Artificial Sequence
<220> FEATURE:
<223> OTHER INFORMATION: Description of Artificial Sequence: plasmid,
      pAN336

<400> SEQUENCE: 72
tgcgccgcta cagggcgcgt ccattcgcca ttcaggctgc gcaactgttg ggaagggcga       60
tcggtgcggg cctcttcgct attacgccag ctggcgaaag ggggatgtgc tgcaaggcga      120
ttaagttggg taacgccagg gttttcccag tcacgacgtt gtaaaacgac ggccagtgaa      180
ttgtaatacg actcactata gggcgaattg ggcccgacgt cgcatgcacc aggcttctca      240
ggcgctgact tagaaaacct cttgaatgaa gctgcgcttg tagcggctcg tcaaaacaag      300
aaaaaaatcg atgcgcgtga tattgacgaa gcgacggacc gtgtaattgc cggacccgct      360
aagaagagcc gcgttatctc caagaaagaa cgcaatatcg tggcttatca cgaaggcgga      420
cacaccgtta tcggtctcgt tttagatgag gcagatatgt tcataaagt aacgattgtt      480 cctcggggcc aggctggcgg ttatgctgtt atgctgccaa gagaagaccg ttatttccaa      540
acaaagccgg agctgcttga taaaattgtc ggcctcttgg gcgacgtgt tgctgaagag      600 attatcttcg gtgaagtcag cacaggggcg cacaatgact tccagcgtgc gacgaatatt      660
gcaagacgaa tggttacaga attcggtatg tcagaaaaac tgggaccgtt gcaatttgga      720
cagtctcagg gcggtcaggt attcttaggc cgtgatttca caacgaaca gaactacagt      780 gatcaaatcg cttacgaaat tgatcaggaa attcagcgca tcatcaaaga atgttatgag      840
cgtgcgaaac aaatcctgac tgaaaatcgt gacaagcttg aattgattgc ccaaacgctt      900
ctgaaagttg aaacgcttga cgctgaacaa atcaaacacc ttatcgatca tggaacatta      960
cctgagcgta atttctcaga tgatgaaaag aacgatgatg tgaaagtaaa cattctgaca     1020
aaaacagaag aaaagaaaga cgatacgaaa gagtaattcg ctttcttcct aaaaaaactg     1080
ccggctgacg ctggcagttt ttttatgtaa atgattggct cagctgcggc ttttacaatc     1140
atccaattct ggtatcgatt tgtttacaaa tgagccgctg atcgtgtatg gtattgtaga     1200
atgtttgtaa aaagtaaagt agagaaacta ttcaaaagtg gtgatagagg ttgttactgg     1260
ttatcgatgt ggggaacacc ctgcagctcg agtgaaatac cgcacagatg cgtaaggaga     1320
aaataccgca tcaggcgata aacccagcga accatttgag gtgataggta agattatacc     1380
gaggtatgaa aacgagaatt ggaccttat agaattactc tatgaagcgc catatttaaa     1440
aagctaccaa gacgaagagg atgaagagga tgaggaggca gattgccttg aatatattga     1500
```

```
caatactgat aagataatat atctttata tagaagatat cgccgtatgt aaggatttca    1560
gggggcaagg cataggcagc gcgcttatca atatatctat agaatgggca aagcataaaa    1620
acttgcatgg actaatgctt gaaacccagg acaataacct tatagcttgt aaattctatc    1680
ataattgtgg tttcaaaatc ggctccgtcg atactatgtt atacgccaac tttcaaaaca    1740
actttgaaaa agctgttttc tggtatttaa ggttttagaa tgcaaggaac agtgaattgg    1800
agttcgtctt gttataatta gcttcttggg gtatctttaa atactgtaga aaagaggaag    1860
gaaataataa atggctaaaa tgagaatatc accggaattg aaaaaactga tcgaaaaata    1920
ccgctgcgta aaagatacgg aaggaatgtc tcctgctaag gtatataagc tggtgggaga    1980
aaatgaaaac ctatatttaa aaatgacgga cagccggtat aaagggacca cctatgatgt    2040
ggaacgggaa aaggacatga tgctatggct ggaaggaaag ctgcctgttc caaaggtcct    2100
gcactttgaa cggcatgatg gctggagcaa tctgctcatg agtgaggccg atggcgtcct    2160
ttgctcggaa gagtatgaag atgaacaaag ccctgaaaag attatcgagc tgtatgcgga    2220
gtgcatcagg ctctttcact ccatcgacat atcggattgt ccctatacga atagcttaga    2280
cagccgctta gccgaattgg attacttact gaataacgat ctggccgatg tggattgcga    2340
aaactgggaa gaagacactc catttaaaga tccgcgcgag ctgtatgatt ttttaaagac    2400
ggaaaagccc gaagaggaac ttgtcttttc ccacggcgac ctgggagaca gcaacatctt    2460
tgtgaaagat ggcaaagtaa gtggctttat tgatcttggg agaagcggca gggcggacaa    2520
gtggtatgac attgccttct gcgtccggtc gatcagggag gatatcgggg aagaacagta    2580
tgtcgagcta ttttttgact tactggggat caagcctgat tgggagaaaa taaaatatta    2640
tattttactg gatgaattgt tttagtacct agatttagat gtctaaaaag ctttaactac    2700
aagcttttta gacatctaat cttttctgaa gtacatccgc aactgtccat actctgatgt    2760
tttatatctt ttctaaaagt tcgctagata ggggtcccga gcgcctacga ggaatttgta    2820
tcgccattcg ccattcaggc tgcgcaactg ttgggaaggg cgatcggtgc ggtcgactgg    2880
caggcaaaac aggacccaag gtcattgcga caggaggcct ggcgccgctc attgcgaacg    2940
aatcagattg tatagacatc gttgatccat tcttaaccct aaaagggctg aattgattt    3000
atgaaagaaa ccgcgtagga agtgtatagg aggtttagta atggattatt tagtaaaagc    3060
acttgcgtat gacggaaaag ttcgggctta tgcagcgaga cgactgata tggtaaatga    3120
ggggcagaga cgccatggta cgtggccgac agcatccgct gcactaggcc gtacaatgac    3180
agcttcactt atgctcggcg ctatgctgaa gggcgatgat aagctgaccg tgaaaatcga    3240
gggcggaggt ccgatcggag ctattgtagc tgatgccaat gccaaaggag aagtcagagc    3300
ctatgtctct aacccgcaag ttcattttga tttaaatgaa caaggtaagc ttgatgtcag    3360
acgtgcggtt ggaacaaacg gaacgttaag tgtcgtaaaa gatttaggtt tgcgcgagtt    3420
cttcacagga caagtagaaa tcgtttcagg agaattagga gatgattta cttactatct    3480
tgtgtcatct gagcaggttc cttcatcagt gggcgtaggt gtgctcgtaa atcctgacaa    3540
taccattctt gcggcagggg gctttattat tcagctgatg ccgggaacag atgatgaaac    3600
aatcacaaaa attgaacagc gtctatctca agtagagccg atttctaagc tcatccaaaa    3660
agggctgaca ccagaagaaa ttttagaaga agtcctaggc gagaaacctg agattttgga    3720
aacgatgcct gtcagattcc attgcccttg ttcaaaagaa cggttcgaaa cagccatttt    3780
aggactaggc aaaaagaaa ttcaagatat gatagaagaa gatggacaag ccgaagcagt    3840
atgccatttt tgtaatgaaa agtacttatt tacaaaagaa gagctggaag ggcttcgtga    3900
```

```
ccaaactacc cgctaagctc tttagcgggt ttttaatttg agaaaagggg ctgaaagcag   3960
gtttgaaatc aagaacaatc tggacgcgtt ggatgcatag cttgagtatt ctatagtgtc   4020
acctaaatag cttggcgtaa tcatggtcat agctgtttcc tgtgtgaaat tgttatccgc   4080
tcacaattcc acacaacata cgagccggaa gcataaagtg taaagcctgg ggtgcctaat   4140
gagtgagcta actcacatta attgcgttgc gctcactgcc cgctttccag tcgggaaacc   4200
tgtcgtgcca gctgcattaa tgaatcggcc aacgcgcggg gagaggcggt ttgcgtattg   4260
ggcgctcttc cgcttcctcg ctcactgact cgctgcgctc ggtcgttcgg ctgcggcgag   4320
cggtatcagc tcactcaaag gcggtaatac ggttatccac agaatcaggg gataacgcag   4380
gaaagaacat gtgagcaaaa ggccagcaaa aggccaggaa ccgtaaaaag gccgcgttgc   4440
tggcgttttt cgataggctc cgcccccctg acgagcatca caaaaatcga cgctcaagtc   4500
agaggtggcg aaacccgaca ggactataaa gataccaggc gtttccccct ggaagctccc   4560
tcgtgcgctc tcctgttccg accctgccgc ttaccggata cctgtccgcc tttctccctt   4620
cgggaagcgt ggcgctttct catagctcac gctgtaggta tctcagttcg gtgtaggtcg   4680
ttcgctccaa gctgggctgt gtgcacgaac cccccgttca gcccgaccgc tgcgccttat   4740
ccggtaacta tcgtcttgag tccaacccgg taagacacga cttatcgcca ctggcagcag   4800
ccactggtaa caggattagc agagcgaggt atgtaggcgg tgctacagag ttcttgaagt   4860
ggtggcctaa ctacggctac actagaagga cagtatttgg tatctgcgct ctgctgaagc   4920
cagttacctt cggaaaaaga gttggtagct cttgatccgg caaacaaacc accgctggta   4980
gcggtggttt ttttgtttgc aagcagcaga ttacgcgcag aaaaaaagga tctcaagaag   5040
atcctttgat cttttctacg gggtctgacg ctcagtggaa cgaaaactca cgttaaggga   5100
ttttggtcat gagattatca aaaaggatct tcacctagat ccttttaaat taaaaatgaa   5160
gttttaaatc aatctaaagt atatatgagt aaacttggtc tgacagttac caatgcttaa   5220
tcagtgaggc acctatctca gcgatctgtc tatttcgttc atccatagtt gcctgactcc   5280
ccgtcgtgta gataactacg atacgggagg gcttaccatc tggccccagt gctgcaatga   5340
taccgcgaga cccacgctca ccggctccag atttatcagc aataaaccag ccagccggaa   5400
gggccgagcg cagaagtggt cctgcaactt tatccgcctc catccagtct attaattgtt   5460
gccgggaagc tagagtaagt agttcgccag ttaatagttt gcgcaacgtt gttggcattg   5520
ctacaggcat cgtggtgtca cgctcgtcgt ttggtatggc ttcattcagc tccggttccc   5580
aacgatcaag gcgagttaca tgatccccca tgttgtgcaa aaaagcggtt agctccttcg   5640
gtcctccgat cgttgtcaga agtaagttgg ccgcagtgtt atcactcatg gttatggcag   5700
cactgcataa ttctcttact gtcatgccat ccgtaagatg cttttctgtg actggtgagt   5760
actcaaccaa gtcattctga gaataccgcg cccggcgacc gagttgctct tgcccggcgt   5820
caatacggga taatagtgta tgacatagca gaactttaaa agtgctcatc attggaaaac   5880
gttcttcggg gcgaaaactc tcaaggatct taccgctgtt gagatccagt tcgatgtaac   5940
ccactcgtgc acccaactga tcttcagcat cttttacttt caccagcgtt tctgggtgag   6000
caaaaacagg aaggcaaaat gccgcaaaaa agggaataag ggcgacacgg aaatgttgaa   6060
tactcatact cttcctttt caatattatt gaagcattta tcagggttat tgtctcatga   6120
gcggatacat atttgaatgt atttagaaaa ataaacaaat aggggttccg cgcacatttc   6180
cccgaaaagt gccacctgta tgcggtgtga aataccgcac agatgcgtaa ggagaaaata   6240
```

```
ccgcatcagg cgaaattgta aacgttaata ttttgttaaa attcgcgtta aatatttgtt     6300
aaatcagctc attttttaac caataggccg aaatcggcaa aatcccttat aaatcaaaag     6360
aatagaccga gatagggttg agtgttgttc cagtttggaa caagagtcca ctattaaaga     6420
acgtggactc caacgtcaaa gggcgaaaaa ccgtctatca gggcgatggc ccactacgtg     6480
aaccatcacc caaatcaagt tttttgcggt cgaggtgccg taaagctcta atcggaacc     6540 ctaaagggag ccccgattt agagcttgac ggggaaagcc ggcgaacgtg gcgagaaagg     6600
aagggaagaa agcgaaagga gcgggcgcta gggcgctggc aagtgtagcg gtcacgctgc     6660
gcgtaaccac cacacccgcc gcgcttaa                                        6688
```

<210> SEQ ID NO 73
<211> LENGTH: 9396
<212> TYPE: DNA
<213> ORGANISM: Artificial Sequence
<220> FEATURE:
<223> OTHER INFORMATION: Description of Artificial Sequence: plasmid,
      pAN341 and pAN342

<400> SEQUENCE: 73

```
ttgcggccgc ttcgaactgt tataaaaaaa ggatcaattt tgaactctct cccaaagttg       60
atcccttaac gatttagaaa tccctttgag aatgtttata tacattcaag gtaaccagcc      120
aactaatgac aatgattcct gaaaaaagta ataacaaatt actatacaga taagttgact      180
gatcaacttc cataggtaac aacctttgat caagtaaggg tatggataat aaaccaccta      240
caattgcaat acctgttccc tctgataaaa agctggtaaa gttaagcaaa ctcattccag      300
caccagcttc ctgctgtttc aagctacttg aaacaattgt tgatataact gttttggtga      360
acgaaagccc acctaaaaca aatacgatta taattgtcat gaaccatgat gttgtttcta      420
aaagaaagga agcagttaaa aagctaacag aaagaaatgt aactccgatg tttaacacgt      480
ataaaggacc tcttctatca acaagtatcc caccaatgta gccgaaaata atgacactca      540
ttgttccagg gaaataatt acacttccga tttcggcagt acttagctgg tgaacatctt      600
tcatcatata aggaaccata gagacaaacc ctgctactgt tccaaatata attccccac      660 aaagaactcc aatcataaaa ggtatatttt tccctaatcc gggatcaaca aaggatctg      720 ttactttcct gatatgtttt acaaatatca ggaatgacag cacgctaacg ataagaaaag      780
aaatgctata tgatgttgta acaacataa aaaatacaat gcctacagac attagtataa      840 ttccttttgat atcaaaatga ccttttatcc ttacttcttt ctttaataat ttcataagaa      900
acggaacagt gataattgtt atcataggaa tgagtagaag ataggaccaa tgaatataat      960
gggctatcat tccaccaatc gctggaccga ctccttctcc catggctact atcgatccaa     1020
taagaccaaa tgctttaccc ctattttcct ttggaatata gcgcgcaact acaaccatta     1080
cgagtgctgg aaatgcagct gcaccagccc cttgaataaa acgagccata ataagtaagg     1140
aaaagaaaga atggccaaca aacccaatta ccgacccgaa acaatttatt ataattccaa     1200
ataggagtaa cctttgatg cctaattgat cagatagctt tccatataca gctgttccaa     1260
tggaaaaggt taacataaag gctgtgttca cccagtttgt actcgcaggt ggtttattaa     1320
aatcatttgc aatatcaggt aatgagacgt tcaaaaccat tcatttaat acgctaaaaa     1380 aagataaaat gcaaagccaa attaaaattt ggttgtgtcg taaattcgat tgtgaatagg     1440
atgtattcac atttcaccct ccaataatga gggcagacgt agtttatagg gttaatgata     1500
cgcttccctc ttttaattga accctgttac attcattaca cttcataatt aattcctcct     1560
```

-continued

```
aaacttgatt aaaacatttt accacatata aactaagttt taaattcagt atttcatcac   1620
ttatacaaca atatggcccg tttgttgaac tactctttaa taaaataatt tttccgttcc   1680
caattccaca ttgcaataat agaaaatcca tcttcatcgg cttttttcgtc atcatctgta  1740
tgaatcaaat cgccttcttc tgtgtcatca aggtttaatt ttttatgtat ttctttttaac 1800
aaaccaccat aggagattaa ccttttacgg tgtaaacctt cctccaaatc agacaaacgt  1860
ttcaaattct tttcttcatc atcggtcata aaatccgtat cctttacagg atattttgca  1920
gtttcgtcaa ttgccgattg tatatccgat ttatatttat ttttcggtcg aatcatttga  1980
acttttacat ttggatcata gtctaatttc attgccttt tccaaaattg aatccattgt   2040
ttttgattca cgtagttttc tgtattctta aaataagttg gttccacaca taccaataca  2100
tgcatgtgct gattataaga attatctta ttatttattg tcacttccgt tgcacgcata   2160
aaaccaacaa gatttttatt aatttttta tattgcatca ttcggcgaaa tccttgagcc   2220
atatctgaca aactcttatt taattcttcg ccatcataaa cattttaaac tgttaatgtg  2280
agaaacaacc aacgaactgt tggcttttgt ttaataactt cagcaacaac cttttgtgac  2340
tgaatgccat gtttcattgc tctcctccag ttgcacattg acaaagcct ggatttacaa   2400
aaccacactc gatacaactt tcttttcgcct gtttcacgat tttgtttata ctctaatatt 2460
tcagcacaat cttttactct ttcagccttt ttaaattcaa gaatatgcag aagttcaaag  2520
taatcaacat tagcgatttt cttttctctc catggggaat tggaattctc agtcgctcca  2580
gttgcaaacg attctggata gtttgccgga tttgcgatag aaccaggccc gccgggaata  2640
aagagatccg tattccccgc tgaaaactca gggaaaatat cggccgaacg ccaggcattg  2700
accatgtctc tgtaccattc atcaagtcca gagcccctc cccatgagtt attgacaaca   2760
tcaggagcca tttccgggtg gggatttcct tccgcgtcct ttggtgctaa aacccattca  2820
ccagcttcca aaatgtcagc atcagtgccg ccatcttcag agaacgcttt aacagcaatc  2880
cattttgcgc caggtgctac accgatttga tttgttccat caggttcaga gcccaccatc  2940
gtgcctgtca cgtgggttcc atgagccaaa tcatcataag ggcttgcctc gcctgctacg  3000
gcatcatacc agttcatttc attttcaggc tcattaggat tttccggatt atatccgcga  3060
tatttctctt ttaatgccgg atgattccat tccaccccgg tatcaatgga cgcaacaacc  3120
gtgccagttc catcatatcc aagtgcccaa gcttttgggg catcgatttg gtctacattc  3180
cattccacac cgtcagttgc tttaatagct ttctgtgctt ttttcatatt aaatggggag  3240
gatgacttaa aaagctgccg tttctcatta ggaagcacct tttccacttc gggaaactgc  3300
accacttttt ccataacctc tttttgaggca tgaacagcaa tcccgttcac cacataataa  3360
gaatgaattt ggtctgcatt tccttatct ttctgggtgt tcaagtattt taggacatct   3420
tgctgggatt catcggctgt gacttttaaa gatgacacaa cagcagaacg cttttgatat  3480
tccgtcttag cggcagacag cttcttcgat ttcgcttttt taacagccgc ttttgccgct  3540
ttttctgggt accccctatgt attactagaa aataacatag taaaacggac atcactccgt  3600
ttcaatggag gtgatgtccg tttttcatta caacaaatta cttatctatt tgtaatgctg  3660
ctcttggacc cgggatccgc aagtgctttt actaaataat ccattactaa acctcctata  3720
cacttcctac gcggtttctt tcataaatca attccagccc ttttagggtt aagaatggat  3780
caacgatgtc tatacaatct gattcgttcg caatgagcgg cgccaggcct cctgtcgcaa  3840
tgaccttggg tcctgttttg cctgccattt cattcgctta acgattcctt ccacttggcc  3900
gacatagcca aataaaattc cagattgcat cgcgctaaca gtgtttttc cgataatatt   3960
```

```
gtcgggccgg gtgatttcga tacgaggaag ctttgctgca cgcgagtaaa gcgcctctgt    4020
cgaaattgta atcccagggg caatcgcccc gccatgtat tgtttgtttt catcaatata    4080
gcagtacgtt gtggcggttc cgaaatcgac aacaattaat ggattgccgt acaagtgtat    4140
cgcagcgaca gcatttacga ttctgtctgc ccctacttct ttcggattgt catattttat    4200
atttaaaccg gttttcatac ctggaccaac aatttgaggc tcgatatgaa agtattttgt    4260
gcacattctt tctaacgcaa acatgattgg cggcactact gacgaaataa taatgccatc    4320
tatctgttca aacataagcc cggagtgatc aaataaggag cgcaaaatca tcccaaactc    4380
atcttctgtt ttatgcctgc ttgtttctat acgccagtga tattctaatt ttccatcatg    4440
atatacacca agtacagtat tggtgttccc cacatcgata accagtaaca acctctatca    4500
ccacttttga atagtttctc tagaacaggc ggggttgccc ccgcctgtaa ttaaattatt    4560
acacaccctg tagggaaagt caatacccttt ttgtaaaatt tttacacagc gtggatctct    4620
tctagggaca cctctttgta cccctcaagg gagaaatatt ggcggtactg agcacagttt    4680
tggttggtgg acagtgaacc atagctgtcg tcaatagcct cgagttatgg cagttggtta    4740
aaaggaaaca aaaagaccgt tttcacacaa acggtctttt ttcgatttct ttttacagtc    4800
acagccactt ttgcaaaaac cggacagctt catgccttat aactgctgtt tcggtcgaca    4860
agcttcgcga agcggccgca aaattcactg gccgtcgttt tacaacgtcg tgactgggaa    4920
aaccctggcg ttaccaact taatcgcctt gcagcacatc ccctttcgc cagctggcgt    4980 aatagcgaag aggcccgcac cgatcgccct tcccaacagt tgcgcagcct gaatggcgaa    5040
tggcgcctga tgcggtattt tctccttacg catctgtgcg gtatttcaca ccgcatatgg    5100
tgcactctca gtacaatctg ctctgatgcc gcatagttaa gccagccccg acacccgcca    5160
acacccgctg actatgcttg taaaccgttt tgtgaaaaaa ttttttaaaat aaaaaagggg    5220 acctctaggg tccccaatta attagtaata taatctatta aaggtcattc aaaaggtcat    5280
ccaccggatc agcttagtaa agccctcgct agattttaat gcggatgttg cgattacttc    5340
gccaactatt gcgataacaa gaaaaagcca gcctttcatg atatatctcc caatttgtgt    5400
agggcttatt atgcacgctt aaaaataata aaagcagact tgacctgata gtttggctgt    5460
gagcaattat gtgcttagtg catctaacgc ttgagttaag ccgcgccgcg aagcggcgtc    5520
ggcttgaacg aattgttaga cattatttgc cgactacctt ggtgatctcg cctttcacgt    5580
agtggacaaa ttcttccaac tgatctgcgc gcgaggccaa gcgatcttct tcttgtccaa    5640
gataagcctg tctagcttca agtatgacgg gctgatactg ggccggcagg cgctccattg    5700
cccagtcggc agcgacatcc ttcggcgcga ttttgccggt tactgcgctg taccaaatgc    5760
gggacaacgt aagcactaca tttcgctcat cgccagccca gtcgggcggc gagttccata    5820
gcgttaaggt ttcatttagc gcctcaaata gatcctgttc aggaaccgga tcaaagagtt    5880
cctccgccgc tggacctacc aaggcaacgc tatgttctct tgcttttgtc agcaagatag    5940
ccagatcaat gtcgatcgtg gctggctcga agatacctgc aagaatgtca ttgcgctgcc    6000
attctccaaa ttgcagttcg cgcttagctg gataacgcca cggaatgatg tcgtcgtgca    6060
caacaatggt gacttctaca gcgcggagaa tctcgctctc tccagggga gccgaagttt    6120 ccaaaaggtc gttgatcaaa gctcgccgcg ttgtttcatc aagccttacg gtcaccgtaa    6180
ccagcaaatc aatatcactg tgtggcttca ggccgccatc cactgcggag ccgtacaaat    6240
gtacggccag caacgtcggt tcgagatggc gctcgatgac gccaactacc tctgatagtt    6300
```

```
gagtcgatac ttcggcgatc accgcttccc tcatgatgtt taactttgtt ttagggcgac    6360
tgccctgctg cgtaacatcg ttgctgctcc ataacatcaa acatcgaccc acggcgtaac    6420
gcgcttgctg cttggatgcc cgaggcatag actgtacccc aaaaaaacag tcataacaag    6480
ccatgaaaac cgccactgcg ccgttaccac cgctgcgttc ggtcaaggtt ctggaccagt    6540
tgcgtgagcg catacgctac ttgcattaca gcttacgaac cgaacaggct tatgtccact    6600
gggttcgtgc cttcatccgt ttccacggtg tgcgtcaccc ggcaaccttg ggcagcagcg    6660
aagtcgaggc atttctgtcc tggctggcga acgagcgcaa ggtttcggtc tccacgcatc    6720
gtcaggcatt ggcggccttg ctgttcttct acggcaaggt gctgtgcacg gatctgccct    6780
ggcttcagga gatcggaaga cctcggccgt cgcggcgctt gccggtggtg ctgaccccgg    6840
atgaagtggt tcgcatcctc ggttttctgg aaggcgagca tcgttgttc gcccagcttc    6900 tgtatggaac gggcatgcgg atcagtgagg gtttgcaact gcgggtcaag gatctggatt    6960
tcgatcacgg cacgatcatc gtgcgggagg gcaagggctc caaggatcgg gccttgatgt    7020
tacccgagag cttggcaccc agcctgcgcg agcaggggaa ttgatccggt ggatgacctt    7080
ttgaatgacc tttaatagat tatattacta attaattggg gaccctagag gtccccttt    7140 ttattttaaa aattttttca caaaacggtt tacaagcata acgggttttg ctgcccgcaa    7200
acgggctgtt ctggtgttgc tagtttgtta tcagaatcgc agatccggct tcaggtttgc    7260
cggctgaaag cgctatttct tccagaattg ccatgatttt ttccccacgg gaggcgtcac    7320
tggctcccgt gttgtcggca gctttgattc gataagcagc atcgcctgtt tcaggctgtc    7380
tatgtgtgac tgttgagctg taacaagttg tctcaggtgt tcaatttcat gttctagttg    7440
ctttgtttta ctggtttcac ctgttctatt aggtgttaca tgctgttcat ctgttacatt    7500
gtcgatctgt tcatggtgaa cagctttaaa tgcaccaaaa actcgtaaaa gctctgatgt    7560
atctatcttt tttacaccgt tttcatctgt gcatatggac agttttccct ttgatatcta    7620
acggtgaaca gttgttctac ttttgtttgt tagtcttgat gcttcactga tagatacaag    7680
agccataaga acctcagatc cttccgtatt tagccagtat gttctctagt gtggttcgtt    7740
gtttttgcgt gagccatgag aacgaaccat tgagatcatg cttactttgc atgtcactca    7800 aaaatttgc ctcaaaactg gtgagctgaa tttttgcagt taaagcatcg tgtagtgttt    7860
ttcttagtcc gttacgtagg taggaatctg atgtaatggt tgttggtatt ttgtcaccat    7920
tcatttttat ctggttgttc tcaagttcgg ttacgagatc catttgtcta tctagttcaa    7980
cttggaaaat caacgtatca gtcgggcggc ctcgcttatc aaccaccaat ttcatattgc    8040
tgtaagtgtt taaatcttta cttattggtt tcaaaaccca ttggttaagc cttttaaact    8100
catggtagtt attttcaagc attaacatga acttaaattc atcaaggcta atctctatat    8160
ttgccttgtg agttttcttt tgtgttagtt cttttaataa ccactcataa atcctcatag    8220
agtatttgtt ttcaaaagac ttaacatgtt ccagattata ttttatgaat tttttaact    8280 ggaaaagata aggcaatatc tcttcactaa aaactaattc taattttcg cttgagaact    8340 tggcatagtt tgtccactgg aaaatctcaa agcctttaac caaaggattc ctgatttcca    8400
cagttctcgt catcagctct ctggttgctt tagctaatac accataagca ttttccctac    8460
tgatgttcat catctgagcg tattggttat aagtgaacga taccgtccgt tctttccttg    8520
tagggttttc aatcgtgggg ttgagtagtg ccacacagca taaaattagc ttggtttcat    8580
gctccgttaa gtcatagcga ctaatcgcta gttcatttgc tttgaaaaca actaattcag    8640
acatacatct caattggtct aggtgatttt aatcactata ccaattgaga tgggctagtc    8700
```

```
aatgataatt actagtccTt ttcctttgag ttgtgggtat ctgtaaattc tgctagacct    8760
ttgctggaaa acttgtaaat tctgctagac cctctgtaaa ttccgctaga cctttgtgtg    8820
ttttttttgt ttatattcaa gtggttataa tttatagaat aaagaaagaa taaaaaaga     8880 taaaaagaat agatcccagc cctgtgtata actcactact ttagtcagtt ccgcagtatt    8940
acaaaaggat gtcgcaaacg ctgtttgctc ctctacaaaa cagaccttaa aaccctaaag    9000
gcttaagtag caccctcgca agctcgggca aatcgctgaa tattccttTt gtctccgacc    9060
atcaggcacc tgagtcgctg tcttttcgt gacattcagt tcgctgcgct cacggctctg    9120
gcagtgaatg ggggtaaatg gcactacagg cgccttttat ggattcatgc aaggaaacta    9180
cccataatac aagaaaagcc cgtcacgggc ttctcagggc gttttatggc gggtctgcta    9240
tgtggtgcta tctgactttt tgctgttcag cagttcctgc cctctgattt tccagtctga    9300
ccacttcgga ttatcccgtg acaggtcatt cagactggct aatgcaccca gtaaggcagc    9360
ggtatcatca acaggcttac ccgtcttact gtcaac                              9396

<210> SEQ ID NO 74
<211> LENGTH: 9292
<212> TYPE: DNA
<213> ORGANISM: Artificial Sequence
<220> FEATURE:
<223> OTHER INFORMATION: Description of Artificial Sequence: plasmid,
      pAN329 and pAN330

<400> SEQUENCE: 74
ttgcggccgc ttcgaactgt tataaaaaaa ggatcaattt tgaactctct cccaaagttg      60
atcccttaac gatttagaaa tcccTttgag aatgttTata tacattcaag gtaaccagcc    120
aactaatgac aatgattcct gaaaaaagta ataacaaatt actatacaga taagttgact    180
gatcaacttc cataggtaac aacctttgat caagtaaggg tatggataat aaaccaccta    240
caattgcaat acctgttccc tctgataaaa agctggtaaa gttaagcaaa ctcattccag    300
caccagcttc ctgctgtttc aagctacttg aaacaattgt tgatataact gttttggtga    360
acgaaagccc acctaaaaca aatacgatta taattgtcat gaaccatgat gttgtttcta    420
aaagaaagga agcagttaaa aagctaacag aaagaaatgt aactccgatg tttaacacgt    480
ataaaggacc tcttctatca acaagtatcc caccaatgta gccgaaaata atgacactca    540
ttgttccagg gaaataatt acacttccga tttcggcagt acttagctgg tgaacatctt    600
tcatcatata aggaaccata gagacaaacc ctgctactgt tccaaatata attcccccac    660
aaagaactcc aatcataaaa ggtatatttt tccctaatcc gggatcaaca aaaggatctg    720
ttactttcct gatatgtttt acaaatatca ggaatgacag cacgctaacg ataagaaaag    780
aaatgctata tgatgttgta acaacataaa aaatacaat gcctacgac attagtataa    840 ttcctttgat atcaaaatga cctTttatcc ttacttcTtt ctttaataat ttcataagaa    900
acggaacagt gataattgtt atcataggaa tgagtagaag ataggaccaa tgaatataat    960
gggctatcat tccaccaatc gctggaccga ctccttctcc catggctact atcgatccaa   1020
taagaccaaa tgctttaccc ctattttcct ttggaatata gcgcgcaact acaaccatta   1080
cgagtgctgg aaatgcagct gcaccagccc ttgaataaaa acgagccata taagtaagg    1140 aaagaaaga atggccaaca aacccaatta ccgacccgaa acaatttatt ataattccaa   1200
ataggagtaa ccttttgatg cctaattgat cagatagctt tccatataca gctgttccaa   1260
tggaaaaggt taacataaag gctgtgttca cccagtttgt actcgcaggt ggtttattaa   1320
```

```
aatcatttgc aatatcaggt aatgagacgt tcaaaaccat ttcatttaat acgctaaaaa   1380
aagataaaat gcaaagccaa attaaaattt ggttgtgtcg taaattcgat tgtgaatagg   1440
atgtattcac atttcaccct ccaataatga gggcagacgt agtttatagg gttaatgata   1500
cgcttccctc ttttaattga accctgttac attcattaca cttcataatt aattcctcct   1560
aaacttgatt aaaacatttt accacatata aactaagttt taaattcagt atttcatcac   1620
ttatacaaca atatggcccg tttgttgaac tactcttaa taaaataatt tttccgttcc    1680
caattccaca ttgcaataat agaaaatcca tcttcatcgg cttttcgtc atcatctgta    1740 tgaatcaaat cgccttcttc tgtgtcatca aggtttaatt ttttatgtat ttcttttaac   1800
aaaccaccat aggagattaa ccttttacgg tgtaaacctt cctccaaatc agacaaacgt   1860
ttcaaattct tttcttcatc atcggtcata aaatccgtat cctttacagg atattttgca   1920
gtttcgtcaa ttgccgattg tatatccgat ttatatttat ttttcggtcg aatcatttga   1980
acttttacat ttggatcata gtctaatttc attgcctttt tccaaaattg aatccattgt   2040
ttttgattca cgtagttttc tgtattctta aaataagttg gttccacaca taccaataca   2100
tgcatgtgct gattataaga attatcttta ttatttattg tcacttccgt tgcacgcata   2160
aaaccaacaa gatttttatt aattttttta tattgcatca ttcggcgaaa tccttgagcc   2220
atatctgaca aactcttatt taattcttcg ccatcataaa cattttaac tgttaatgtg     2280 agaaacaacc aacgaactgt tggcttttgt ttaataactt cagcaacaac cttttgtgac   2340
tgaatgccat gtttcattgc tctcctccag ttgcacattg acaaagcct ggatttacaa     2400 aaccacactc gatacaactt tcttttcgcct gtttcacgat tttgttata ctctaatatt    2460 tcagcacaat cttttactct ttcagccttt ttaaattcaa gaatatgcag aagttcaaag   2520
taatcaacat tagcgatttt cttttctctc catggggaat tggaattctc agtcgctcca   2580
gttgcaaacg attctggata gtttgccgga tttgcgatag aaccaggccc gccgggaata   2640
aagagatccg tattcccgc tgaaaactca gggaaaatat cggccgaacg ccaggcattg     2700
accatgtctc tgtaccattc atcaagtcca gagccccctc cccatgagtt attgacaaca   2760
tcaggagcca tttccgggtg gggatttcct tccgcgtcct ttggtgctaa aacccattca   2820
ccagcttcca aaatgtcagc atcagtgccg ccatcttcag agaacgcttt aacagcaatc   2880
cattttgcgc caggtgctac accgatttga tttgttccat caggttcaga gcccaccatc   2940
gtgcctgtca cgtgggttcc atgagccaaa tcatcataag ggcttgcctc gcctgctacg   3000
gcatcatacc agttcatttc attttcaggc tcattaggat tttccggatt atatccgcga   3060
tatttctctt ttaatgccgg atgattccat tccaccccgg tatcaatgga cgcaacaacc   3120
gtgccagttc catcatatcc aagtgcccaa gcttttgggg catcgatttg gtctacattc   3180
cattccacac cgtcagttgc tttaatagct ttctgtgctt ttttcatatt aaatggggag   3240
gatgacttaa aaagctgccg tttctcatta ggaagcacct tttccacttc gggaaactgc   3300
accacttttt cctaaccctc ttttgaggca tgaacagcaa tcccgttcac cacataataa   3360
gaatgaattt ggtctgcatt tcctttatct ttctgggtgt tcaagtattt taggacatct   3420
tgctgggatt catcggctgt gacttttaaa gatgacacaa cagcagaacg cttttgatat   3480
tccgtcttag cggcagacag cttcttcgat ttcgcttttt taacagccgc ttttgccgct   3540
ttttctgggt acccctatgt attactagaa aataacatag taaaacggac atcactccgt   3600
ttcaatggag gtgatgtccg tttttcatta caacaaatta cttatctatt tgtaatgctg   3660
```

```
ctcttggacc cgggatccac gatgtctata caatctgatt cgttcgcaat gagcggcgcc    3720
aggcctcctg tcgcaatgac cttgggtcct gttttgcctg ccatttcatt cgcttaacga    3780
ttccttccac ttggccgaca tagccaaata aaattccaga ttgcatcgcg ctaacagtgt    3840
tttttccgat aatattgtcg ggccgggtga tttcgatacg aggaagcttt gctgcacgcg    3900
agtaaagcgc ctctgtcgaa attgtaatcc caggggcaat cgccccgccc atgtattgtt    3960
tgttttcatc aatatagcag tacgttgtgg cggttccgaa atcgacaaca attaatggat    4020
tgccgtacaa gtgtatcgca gcgacagcat ttacgattct gtctgcccct acttctttcg    4080
gattgtcata ttttatattt aaaccggttt tcatacctgg accaacaatt tgaggctcga    4140
tatgaaagta ttttgtgcac attctttcta acgcaaacat gattggcggc actactgacg    4200
aaataataat gccatctatc tgttcaaaca taagcccgga gtgatcaaat aaggagcgca    4260
aaatcatccc aaactcatct tctgttttat gcctgcttgt ttctatacgc cagtgatatt    4320
ctaattttcc atcatgatat acaccaagta cagtattggt gttccccaca tcgataacca    4380
gtaacaacct ctatcaccac ttttgaatag tttctctaga acaggcgggg ttgccccgc     4440 ctgtaattaa attattacac accctgtagg gaaagtcaat accttttgt aaaatttta     4500 cacagcgtgg atctcttcta gggacacctc tttgtacccc tcaagggaga atattggcg     4560 gtactgagca cagttttggt tggtggacag tgaaccatag ctgtcgtcaa tagcctcgag    4620
ttatggcagt tggttaaaag gaaacaaaaa gaccgttttc acacaaaacg gtcttttcg     4680 atttctttt acagtcacag ccactttgc aaaaaccgga cagcttcatg ccttataact      4740
gctgtttcgg tcgacaagct tcgcgaagcg ccgcaaaat tcactggccg tcgttttaca     4800
acgtcgtgac tgggaaaacc ctggcgttac ccaacttaat cgccttgcag cacatccccc    4860
tttcgccagc tggcgtaata gcgaagaggc ccgcaccgat cgcccttccc aacagttgcg    4920
cagcctgaat ggcgaatggc gcctgatgcg gtatttctc cttacgcatc tgtgcggtat     4980
ttcacaccgc atatggtgca ctctcagtac aatctgctct gatgccgcat agttaagcca    5040
gccccgacac ccgccaacac ccgctgacta tgcttgtaaa ccgttttgtg aaaaaatttt    5100
taaaataaaa aaggggacct ctagggtccc caattaatta gtaatataat ctattaaagg    5160
tcattcaaaa ggtcatccac cggatcagct tagtaaagcc ctcgctagat tttaatgcgg    5220
atgttgcgat tacttcgcca actattgcga taacaagaaa aagccagcct ttcatgatat    5280
atctcccaat ttgtgtaggg cttattatgc acgcttaaaa ataataaaag cagacttgac    5340
ctgatagttt ggctgtgagc aattatgtgc ttagtgcatc taacgcttga gttaagccgc    5400
gccgcgaagc ggcgtcggct tgaacgaatt gttagacatt atttgccgac taccttggtg    5460
atctcgcctt tcacgtagtg acaaattct tccaactgat ctgcgcgcga ggccaagcga    5520
tcttcttctt gtccaagata agcctgtcta gcttcaagta tgacgggctg atactgggcc    5580
ggcaggcgct ccattgccca gtcggcagcg acatccttcg cgcgatttt gccggttact     5640 gcgctgtacc aaatgcggga caacgtaagc actacatttc gctcatcgcc agcccagtcg    5700
ggcggcgagt tccatagcgt taaggtttca tttagcgcct caaatagatc ctgttcagga    5760
accggatcaa agagttcctc cgccgctgga cctaccaagg caacgctatg ttctcttgct    5820
tttgtcagca agatagccag atcaatgtcg atcgtggctg gctcgaagat acctgcaaga    5880
atgtcattgc gctgccattc tccaaattgc agttcgcgct tagctggata acgccacgga    5940
atgatgtcgt cgtgcacaac aatggtgact tctacagcgc ggagaatctc gctctctcca    6000
ggggaagccg aagtttccaa aaggtcgttg atcaaagctc gccgcgttgt ttcatcaagc    6060
```

```
cttacggtca ccgtaaccag caaatcaata tcactgtgtg gcttcaggcc gccatccact   6120
gcggagccgt acaaatgtac ggccagcaac gtcggttcga gatggcgctc gatgacgcca   6180
actacctctg atagttgagt cgatacttcg gcgatcaccg cttccctcat gatgtttaac   6240
tttgttttag ggcgactgcc ctgctgcgta acatcgttgc tgctccataa catcaaacat   6300
cgacccacgg cgtaacgcgc ttgctgcttg gatgcccgag gcatagactg taccccaaaa   6360
aaacagtcat aacaagccat gaaaaccgcc actgcgccgt taccaccgct gcgttcggtc   6420
aaggttctgg accagttgcg tgagcgcata cgctacttgc attacagctt acgaaccgaa   6480
caggcttatg tccactgggt tcgtgccttc atccgtttcc acggtgtgcg tcacccggca   6540
accttgggca gcagcgaagt cgaggcattt ctgtcctggc tggcgaacga gcgcaaggtt   6600
tcggtctcca cgcatcgtca ggcattggcg gccttgctgt tcttctacgg caaggtgctg   6660
tgcacggatc tgccctggct tcaggagatc ggaagacctc ggccgtcgcg gcgcttgccg   6720
gtggtgctga ccccggatga agtggttcgc atcctcggtt ttctggaagg cgagcatcgt   6780
ttgttcgccc agcttctgta tggaacgggc atgcggatca gtgagggttt gcaactgcgg   6840
gtcaaggatc tggatttcga tcacggcacg atcatcgtgc gggagggcaa gggctccaag   6900
gatcgggcct tgatgttacc cgagagcttg gcacccagcc tgcgcgagca ggggaattga   6960
tccggtggat gaccttttga atgacccttta atagattata ttactaatta attggggacc   7020
ctagaggtcc cctttttat tttaaaaatt ttttcacaaa acggtttaca agcataacgg   7080
gttttgctgc ccgcaaacgg gctgttctgg tgttgctagt tgttatcag aatcgcagat   7140 ccggcttcag gtttgccggc tgaaagcgct atttcttcca gaattgccat gattttttcc   7200
ccacgggagg cgtcactggc tcccgtgttg tcggcagctt tgattcgata agcagcatcg   7260
cctgtttcag gctgtctatg tgtgactgtt gagctgtaac aagttgtctc aggtgttcaa   7320
tttcatgttc tagttgcttt gttttactgg tttcacctgt tctattaggt gttacatgct   7380
gttcatctgt tacattgtcg atctgttcat ggtgaacagc tttaaatgca ccaaaaactc   7440
gtaaaagctc tgatgtatct atcttttta caccgttttc atctgtgcat atggacagtt   7500 ttcccttga tatctaacgg tgaacagttg ttctacttt gtttgttagt cttgatgctt   7560
cactgataga tacaagagcc ataagaacct cagatccttc cgtatttagc cagtatgttc   7620
tctagtgtgg ttcgttgttt ttgcgtgagc catgagaacg aaccattgag atcatgctta   7680
ctttgcatgt cactcaaaaa ttttgcctca aaactggtga gctgaatttt tgcagttaaa   7740
gcatcgtgta gtgttttct tagtccgtta cgtaggtagg aatctgatgt aatggttgtt   7800
ggtattttgt caccattcat tttatctgg ttgttctcaa gttcggttac gagatccatt   7860
tgtctatcta gttcaacttg gaaaatcaac gtatcagtcg gcggcctcg cttatcaacc   7920 accaatttca tattgctgta agtgtttaaa tctttactta ttggttttcaa acccattgg   7980 ttaagccttt taaactcatg gtagttattt tcaagcatta acatgaactt aaattcatca   8040
aggctaatct ctatatttgc cttgtgagtt ttcttttgtg ttagttcttt taataaccac   8100
tcataaatcc tcatagagta tttgttttca aaagacttaa catgttccag attatatttt   8160
atgaattttt ttaactggaa agataaggc aatatctctt cactaaaaac taattctaat   8220
ttttcgcttg agaacttggc atagtttgtc cactggaaaa tctcaaagcc tttaaccaaa   8280
ggattcctga tttccacagt tctcgtcatc agctctctgg ttgctttagc taatacccha   8340
taagcatttt ccctactgat gttcatcatc tgagcgtatt ggttataagt gaacgatacc   8400
```

```
gtccgttctt tccttgtagg gttttcaatc gtggggttga gtagtgccac acagcataaa    8460
attagcttgg tttcatgctc cgttaagtca tagcgactaa tcgctagttc atttgctttg    8520
aaaacaacta attcagacat acatctcaat tggtctaggt gattttaatc actataccaa    8580
ttgagatggg ctagtcaatg ataattacta gtccttttcc tttgagttgt gggtatctgt    8640
aaattctgct agacctttgc tggaaaactt gtaaattctg ctagaccctc tgtaaattcc    8700
gctagacctt tgtgtgtttt ttttgtttat attcaagtgg ttataattta tagaataaag    8760
aaagaataaa aaaagataaa aagaatagat cccagccctg tgtataactc actactttag    8820
tcagttccgc agtattacaa aaggatgtcg caaacgctgt ttgctcctct acaaaacaga    8880
ccttaaaacc ctaaaggctt aagtagcacc ctcgcaagct cgggcaaatc gctgaatatt    8940 cctttgtct ccgaccatca ggcacctgag tcgctgtctt tttcgtgaca ttcagttcgc    9000
tgcgctcacg gctctggcag tgaatggggg taaatggcac tacaggcgcc ttttatggat    9060
tcatgcaagg aaaactaccca taatacaaga aagcccgtc acgggcttct cagggcgttt    9120
tatggcgggt ctgctatgtg gtgctatctg acttttgct gttcagcagt tcctgccctc    9180
tgattttcca gtctgaccac ttcggattat cccgtgacag gtcattcaga ctggctaatg    9240
cacccagtaa ggcagcggta tcatcaacag gcttacccgt cttactgtca ac           9292

<210> SEQ ID NO 75
<211> LENGTH: 3964
<212> TYPE: DNA
<213> ORGANISM: Artificial Sequence
<220> FEATURE:
<223> OTHER INFORMATION: Description of Artificial Sequence: plasmid,
      pOTP71

<400> SEQUENCE: 75
ccatcgaatg gccagatgat taattcctaa ttttttgttga cactctatca ttgatagagt      60
tattttacca ctccctatca gtgatagaga aagtgaaat gaatagttcg acaaaaatct      120
agaaaaggag gaatttaaat gttactggtt atcgatgtgg ggaacaccaa tactgtactt      180
ggtgtatatc atgatggaaa attagaatat cactggcgta tagaaacaag caggcataaa      240
acagaagatg agtttgggat gattttgcgc tccttatttg atcactccgg gcttatgttt      300
gaacagatag atggcattat tatttcgtca gtagtgccgc caatcatgtt tgcgttagaa      360
agaatgtgca caaaatactt tcatatcgag cctcaaattg ttggtccagg tatgaaaacc      420
ggtttaaata taaatatga caatccgaaa gaagtagggg cagacagaat cgtaaatgct      480
gtcgctgcga tacacttgta cggcaatcca ttaattgttg tcgatttcgg aaccgccaca      540
acgtactgct atattgatga aaacaaacaa tacatgggcg gggcgattgc ccctgggatt      600
acaatttcga cagaggcgct ttactcgcgt gcagcaaagc ttcctcgtat cgaaatcacc      660
cggcccgaca atattatcgg aaaaaacact gttagcgcga tgcaatctgg aattttattt      720
ggctatgtcg gccaagtgga aggaatcgtt aagcgaatga atggcaggc aaaacaggac      780 cccaaggtca ttgcgacagg aggcctggcg ccgctcattg cgaacgaatc agattgtata      840
gacatcgttg atccattctt aacccctaaaa gggctggaat tgatttatga agaaaccgc      900 gtaggaagtg tataaggatc cctcgaggtc gacctgcagg gggaccatgg tctcagcgct      960
tggagccacc cgcagttcga aaaataataa gcttgacctg tgaagtgaaa aatggcgcac     1020
attgtgcgac attttttttg tctgccgttt accgctactg cgtcacggat ctccacgcgc     1080
cctgtagcgg cgcattaagc gcggcgggtg tggtggttac gcgcagcgtg accgctacac     1140
```

```
ttgccagcgc cctagcgccc gctcctttcg ctttcttccc ttcctttctc gccacgttcg   1200
ccggctttcc ccgtcaagct ctaaatcggg ggctcccttt agggttccga tttagtgctt   1260
tacggcacct cgaccccaaa aaacttgatt agggtgatgg ttcacgtagt gggccatcgc   1320
cctgatagac ggttttcgc cctttgacgt tggagtccac gttctttaat agtggactct   1380
tgttccaaac tggaacaaca ctcaaccta tctcggtcta ttcttttgat ttataaggga   1440
ttttgccgat ttcggcctat tggttaaaaa atgagctgat ttaacaaaaa tttaacgcga   1500
attttaacaa aatattaacg cttacaattt caggtggcac ttttcgggga aatgtgcgcg   1560 gaaccctat ttgtttattt ttctaaatac attcaaatat gtatccgctc atgagacaat   1620
aaccctgata aatgcttcaa taatattgaa aaaggaagag tatgagtatt caacatttcc   1680
gtgtcgccct tattcccttt tttgcggcat tttgccttcc tgttttgct cacccagaaa   1740 cgctggtgaa agtaaaagat gctgaagatc agttgggtgc acgagtgggt tacatcgaac   1800
tggatctcaa cagcggtaag atccttgaga gttttcgccc cgaagaacgt tttccaatga   1860
tgagcacttt taaagttctg ctatgtggcg cggtattatc ccgtattgac gccgggcaag   1920
agcaactcgg tcgccgcata cactattctc agaatgactt ggttgagtac tcaccagtca   1980
cagaaaagca tcttacggat ggcatgacag taagagaatt atgcagtgct gccataacca   2040
tgagtgataa cactgcggcc aacttacttc tgacaacgat cggaggaccg aaggagctaa   2100 ccgcttttt gcacaacatg ggggatcatg taactcgcct gatcgttgg gaaccggagc   2160 tgaatgaagc cataccaaac gacgagcgtg acaccacgat gcctgtagca atggcaacaa   2220
cgttgcgcaa actattaact ggcgaactac ttactctagc ttcccggcaa caattgatag   2280
actggatgga ggcggataaa gttgcaggac cacttctgcg ctcggccctt ccggctggct   2340
ggtttattgc tgataaatct ggagccggtg agcgtggctc tcgcggtatc attgcagcac   2400
tggggccaga tggtaagccc tcccgtatcg tagttatcta cacgacgggg agtcaggcaa   2460
ctatggatga acgaaataga cagatcgctg agataggtgc ctcactgatt aagcattggt   2520
aggaattaat gatgtctcgt ttagataaaa gtaaagtgat taacagcgca ttagagctgc   2580
ttaatgaggt cggaatcgaa ggtttaacaa cccgtaaact cgcccagaag ctaggtgtag   2640
agcagcctac attgtattgg catgtaaaaa ataagcgggc tttgctcgac gccttagcca   2700
ttgagatgtt agataggcac catactcact tttgcccttt agaagggaa agctggcaag   2760 atttttacg taataacgct aaaagtttta gatgtgcttt actaagtcat cgcgatggag   2820
caaaagtaca tttaggtaca cggcctacag aaaaacagta tgaaactctc gaaaatcaat   2880
tagccttttt atgccaacaa ggttttttcac tagagaatgc attatatgca ctcagcgcag   2940
tggggcattt tactttaggt tgcgtattgg aagatcaaga gcatcaagtc gctaaagaag   3000
aaagggaaac acctactact gatagtatgc cgccattatt acgacaagct atcgaattat   3060
ttgatcacca aggtgcagag ccagccttct tattcggcct tgaattgatc atatgcggat   3120
tagaaaaaca acttaaatgt gaaagtgggt cttaaaagca gcataaccct ttccgtgat   3180 ggtaacttca ctagtttaaa aggatctagg tgaagatcct ttttgataat ctcatgacca   3240
aaatccctta acgtgagttt tcgttccact gagcgtcaga ccccgtagaa aagatcaaag   3300
gatcttcttg agatccttt tttctgcgcg taatctgctg cttgcaaaca aaaaaaccac   3360
cgctaccagc ggtggtttgt ttgccggatc aagagctacc aactcttttt ccgaaggtaa   3420
ctggcttcag cagagcgcag ataccaaata ctgtccttct agtgtagccg tagttaggcc   3480
accacttcaa gaactctgta gcaccgccta catacctcgc tctgctaatc ctgttaccag   3540
```

```
tggctgctgc cagtggcgat aagtcgtgtc ttaccgggtt ggactcaaga cgatagttac    3600
cggataaggc gcagcggtcg ggctgaacgg ggggttcgtg cacacagccc agcttggagc    3660
gaacgaccta caccgaactg agatacctac agcgtgagct atgagaaagc gccacgcttc    3720
ccgaagggag aaaggcggac aggtatccgg taagcggcag ggtcggaaca ggagagcgca    3780
cgagggagct tccaggggga aacgcctggt atctttatag tcctgtcggg tttcgccacc    3840
tctgacttga gcgtcgattt tgtgatgct cgtcagggg gcggagccta tggaaaaacg    3900
ccagcaacgc ggccttttta cggttcctgg ccttttgctg gccttttgct cacatgaccc    3960
gaca                                                                3964
```

<210> SEQ ID NO 76
<211> LENGTH: 3859
<212> TYPE: DNA
<213> ORGANISM: Artificial Sequence
<220> FEATURE:
<223> OTHER INFORMATION: Description of Artificial Sequence: plasmid,
    pOTP72

<400> SEQUENCE: 76

```
ccatcgaatg gccagatgat taattcctaa ttttttgttga cactctatca ttgatagagt      60
tattttacca ctccctatca gtgatagaga aagtgaaat gaatagttcg acaaaaatct     120
agaaaaggag gaatttaaat gccagctagg caatcttta cagatttgaa aaacctggtt     180
ttgtgcgata taggcaacac gcgtatccat tttgcacaaa actatcagct cttttcaagc     240
gctaaagaag atttaaagcg tttgggtatt caaaaggaaa ttttttacat tagcgtgaat     300
gaagaaaatg aaaaagccct tttgaattgt taccctaacg ctaaaaatat tgcagggttt     360
tttcatttag aaaccgacta tgtagggctt gggatagacc ggcaaatggc gtgtctggcg     420
gtaaataatg gcgtggtggt ggatgccggg agtgcgatta cgatagattt aatcaaagag     480
ggcaagcatt taggagggtg tatttttaccc ggtttagccc aatatattca tgcgtataaa     540
aaaagcgcta aaattttaga gcaacctttc aaggccttag attctttaga agttttacct     600
aaaagcacta gagacgctgt gaattacggc atggttttga gcgtcattgc ttgtatccag     660
catttagcca aaaatcaaaa aatctatctt tgtgggggcg atgcgaagta tttgagcgcg     720 ttttttacccc attctgtttg caaggagcgt ttggttttg acgggatgga aatcgctctt     780
aaaaaagcag ggatactaga atgcaaataa ggatccctcg aggtcgacct gcaggggggac     840 catggtctca gcgcttggag ccacccgcag ttcgaaaaat aataagcttg acctgtgaag     900
tgaaaaatgg cgcacattgt gcgacatttt tttttgtctgc cgtttaccgc tactgcgtca     960
cggatctcca cgcgccctgt agcggcgcat taagcgcggc gggtgtggtg gttacgcgca    1020
gcgtgaccgc tacacttgcc agcgccctag cgcccgctcc tttcgctttc ttcccttcct    1080
ttctcgccac gttcgccggc tttccccgtc aagctctaaa tcgggggctc cctttagggt    1140
tccgatttag tgctttacgg cacctcgacc ccaaaaaact tgattagggt gatggttcac    1200
gtagtgggcc atcgccctga tagacggttt ttcgcccttt gacgttggag tccacgttct    1260
ttaatagtgg actcttgttc caaactggaa caacactcaa ccctatctcg gtctattctt    1320
ttgatttata agggattttg ccgatttcgg cctattggtt aaaaaatgag ctgatttaac    1380
aaaaatttaa cgcgaatttt aacaaaatat taacgcttac aatttcaggt ggcacttttc    1440
ggggaaatgt gcgcggaacc cctatttgtt tatttttcta aatacattca aatatgtatc    1500
cgctcatgag acaataaccc tgataaatgc ttcaataata ttgaaaaagg aagagtatga    1560
```

```
gtattcaaca tttccgtgtc gcccttattc ccttttttgc ggcatttttgc cttcctgttt    1620
ttgctcaccc agaaacgctg gtgaaagtaa aagatgctga agatcagttg ggtgcacgag    1680
tgggttacat cgaactggat ctcaacagcg gtaagatcct tgagagtttt cgccccgaag    1740
aacgttttcc aatgatgagc acttttaaag ttctgctatg tggcgcggta ttatcccgta    1800
ttgacgccgg gcaagagcaa ctcggtcgcc gcatacacta ttctcagaat gacttggttg    1860
agtactcacc agtcacagaa aagcatctta cggatggcat gacagtaaga gaattatgca    1920
gtgctgccat aaccatgagt gataacactg cggccaactt acttctgaca acgatcggag    1980
gaccgaagga gctaaccgct tttttgcaca acatgggggga tcatgtaact cgccttgatc    2040
gttgggaacc ggagctgaat gaagccatac caaacgacga gcgtgacacc acgatgcctg    2100
tagcaatggc aacaacgttg cgcaaactat taactggcga actacttact ctagcttccc    2160
ggcaacaatt gatagactgg atggaggcgg ataaagttgc aggaccactt ctgcgctcgg    2220
cccttccggc tggctggttt attgctgata aatctggagc cggtgagcgt ggctctcgcg    2280
gtatcattgc agcactgggg ccagatggta agccctcccg tatcgtagtt atctacacga    2340
cggggagtca ggcaactatg gatgaacgaa atagacagat cgctgagata ggtgcctcac    2400
tgattaagca ttggtaggaa ttaatgatgt ctcgtttaga taaaagtaaa gtgattaaca    2460
gcgcattaga gctgcttaat gaggtcggaa tcgaaggttt aacaacccgt aaactcgccc    2520
agaagctagg tgtagagcag cctacattgt attggcatgt aaaaaataag cgggctttgc    2580
tcgacgcctt agccattgag atgttagata ggcaccatac tcacttttgc cctttagaag    2640
gggaaagctg gcaagatttt ttacgtaata acgctaaaag ttttagatgt gctttactaa    2700
gtcatcgcga tggagcaaaa gtacatttag gtacacggcc tacagaaaaa cagtatgaaa    2760
ctctcgaaaa tcaattagcc tttttatgcc aacaaggttt ttcactagag aatgcattat    2820
atgcactcag cgcagtgggg catttttactt taggttgcgt attggaagat caagagcatc    2880
aagtcgctaa agaagaaagg gaaacaccta ctactgatag tatgccgcca ttattacgac    2940
aagctatcga attatttgat caccaaggtg cagagccagc cttcttattc ggccttgaat    3000
tgatcatatg cggattagaa aaacaactta aatgtgaaag tgggtcttaa aagcagcata    3060
accttttttcc gtgatggtaa cttcactagt ttaaaaggat ctaggtgaag atccttttttg    3120
ataatctcat gaccaaaatc ccttaacgtg agttttcgtt ccactgagcg tcagaccccg    3180
tagaaaagat caaaggatct tcttgagatc ctttttttct gcgcgtaatc tgctgcttgc    3240
aaacaaaaaa accaccgcta ccagcggtgg tttgtttgcc ggatcaagag ctaccaactc    3300
tttttccgaa ggtaactggc ttcagcagag cgcagatacc aaatactgtc cttctagtgt    3360
agccgtagtt aggccaccac ttcaagaact ctgtagcacc gcctacatac ctcgctctgc    3420
taatcctgtt accagtggct gctgccagtg gcgataagtc gtgtcttacc gggttggact    3480
caagacgata gttaccggat aaggcgcagc ggtcgggctg aacggggggt cgtgcacac    3540
agcccagctt ggagcgaacg acctacaccg aactgagata cctacagcgt gagctatgag    3600
aaagcgccac gcttcccgaa gggagaaagg cggacaggta tccggtaagc ggcagggtcg    3660
gaacaggaga gcgcacgagg gagcttccag ggggaaacgc ctggtatctt tatagtcctg    3720
tcgggtttcg ccacctctga cttgagcgtc gatttttgtg atgctcgtca ggggggcgga    3780
gcctatggaa aaacgccagc aacgcggcct ttttacggtt cctggccttt tgctggcctt    3840
ttgctcacat gacccgaca                                                 3859
```

<210> SEQ ID NO 77
<211> LENGTH: 3934
<212> TYPE: DNA
<213> ORGANISM: Artificial Sequence
<220> FEATURE:
<223> OTHER INFORMATION: Description of Artificial Sequence: plasmid, pOTP73

<400> SEQUENCE: 77

| | | | | | |
|---|---|---|---|---|---|
| ccatcgaatg | gccagatgat | taattcctaa | tttttgttga | cactctatca | ttgatagagt | 60 |
| tattttacca | ctccctatca | gtgatagaga | aaagtgaaat | gaatagttcg | acaaaaatct | 120 |
| agaaaaggag | gaatttaaat | gattcttgag | ctcgactgtg | gaaactcgct | gatcaagtgg | 180 |
| cgggtcatcg | agggggcggc | gcggtcggtc | gccggtggcc | ttgcggagtc | cgatgatgcc | 240 |
| ctggtcgaac | agttaacgtc | gcagcaagcg | ctgccagtgc | gagcctgtcg | cctggtgagc | 300 |
| gttcgcagcg | agcaggaaac | ctcgcaactg | gtcgcacggt | tggagcagct | gttcccggtt | 360 |
| tcggcgctgg | ttgcatcatc | cggcaagcag | ttggcgggtg | tgcgcaacgg | ctatctcgat | 420 |
| taccagcgcc | tggggctcga | ccgctggctg | gccctcgtcg | cggctcatca | cctggctaag | 480 |
| aaggcctgcc | tggtcattga | tctggggacc | gcggtcacct | ctgacctggt | cgcggcggat | 540 |
| ggagtgcatc | tggggggcta | catatgcccg | ggcatgaccc | tgatgagaag | ccagttgcgc | 600 |
| acccataccc | gacgtatccg | ctacgacgat | gcagaggccc | ggcgggcgct | tgccagtctc | 660 |
| cagccagggc | aggccacggc | cgaggcggtt | gagcggggtt | gtctgctcat | gctcagggg | 720 |
| ttcgttcgtg | agcagtacgc | catggcgtgc | gagctgctcg | gtccggattg | tgaaatattc | 780 |
| ctgacgggtg | gggatgccga | actggttcgc | gacgaactgg | ctggcgcccg | gatcatgccg | 840 |
| gacctggttt | tcgtagggct | ggcactggct | tgcccgattg | agtaaggatc | cctcgaggtc | 900 |
| gacctgcagg | gggaccatgg | tctcagcgct | tggagccacc | cgcagttcga | aaataataa | 960 |
| gcttgacctg | tgaagtgaaa | aatggcgcac | attgtgcgac | atttttttg | tctgccgttt | 1020 |
| accgctactg | cgtcacggat | ctccacgcgc | cctgtagcgg | cgcattaagc | gcggcgggtg | 1080 |
| tggtggttac | gcgcagcgtg | accgctacac | ttgccagcgc | cctagcgccc | gctcctttcg | 1140 |
| ctttcttccc | ttcctttctc | gccacgttcg | ccggctttcc | ccgtcaagct | ctaaatcggg | 1200 |
| ggctcccttt | agggttccga | tttagtgctt | tacggcacct | cgaccccaaa | aaacttgatt | 1260 |
| agggtgatgg | ttcacgtagt | gggccatcgc | cctgatagac | ggtttttcgc | cctttgacgt | 1320 |
| tggagtccac | gttctttaat | agtggactct | tgttccaaac | tggaacaaca | ctcaacccta | 1380 |
| tctcggtcta | ttcttttgat | ttataaggga | ttttgccgat | ttcggcctat | tggttaaaaa | 1440 |
| atgagctgat | ttaacaaaaa | tttaacgcga | attttaacaa | aatattaacg | cttacaattt | 1500 |
| caggtggcac | ttttcgggga | aatgtgcgcg | gaacccctat | ttgtttattt | ttctaaatac | 1560 |
| attcaaatat | gtatccgctc | atgagacaat | aaccctgata | aatgcttcaa | taatattgaa | 1620 |
| aaaggaagag | tatgagtatt | caacatttcc | gtgtcgccct | tattcccttt | tttgcggcat | 1680 |
| tttgccttcc | tgttttgct | cacccagaaa | cgctggtgaa | agtaaaagat | gctgaagatc | 1740 |
| agttgggtgc | acgagtgggt | tacatcgaac | tggatctcaa | cagcggtaag | atccttgaga | 1800 |
| gttttcgccc | cgaagaacgt | tttccaatga | tgagcacttt | taaagttctg | ctatgtggcg | 1860 |
| cggtattatc | ccgtattgac | gccgggcaag | agcaactcgg | tcgccgcata | cactattctc | 1920 |
| agaatgactt | ggttgagtac | tcaccagtca | cagaaaagca | tcttacggat | ggcatgacag | 1980 |

```
taagagaatt atgcagtgct gccataacca tgagtgataa cactgcggcc aacttacttc    2040
tgacaacgat cggaggaccg aaggagctaa ccgcttttt gcacaacatg ggggatcatg    2100
taactcgcct tgatcgttgg aaccggagc tgaatgaagc cataccaaac gacgagcgtg    2160
acaccacgat gcctgtagca atggcaacaa cgttgcgcaa actattaact ggcgaactac    2220
ttactctagc ttcccggcaa caattgatag actggatgga ggcggataaa gttgcaggac    2280
cacttctgcg ctcggccctt ccggctggct ggtttattgc tgataaatct ggagccggtg    2340
agcgtggctc tcgcggtatc attgcagcac tggggccaga tggtaagccc tcccgtatcg    2400
tagttatcta cacgacgggg agtcaggcaa ctatggatga cgaaataga cagatcgctg    2460 agataggtgc ctcactgatt aagcattggt aggaattaat gatgtctcgt ttagataaaa    2520
gtaaagtgat taacagcgca ttagagctgc ttaatgaggt cggaatcgaa ggtttaacaa    2580
cccgtaaact cgcccagaag ctaggtgtag agcagcctac attgtattgg catgtaaaaa    2640
ataagcgggc tttgctcgac gccttagcca ttgagatgtt agataggcac catactcact    2700
tttgcccttt agaaggggaa agctggcaag atttttacg taataacgct aaaagtttta    2760
gatgtgcttt actaagtcat cgcgatggag caaaagtaca tttaggtaca cggcctacag    2820
aaaaacagta tgaaactctc gaaaatcaat tagccttttt atgccaacaa ggttttcac    2880 tagagaatgc attatatgca ctcagcgcag tggggcattt tactttaggt tgcgtattgg    2940
aagatcaaga gcatcaagtc gctaaagaag aaagggaaac acctactact gatagtatgc    3000
cgccattatt acgacaagct atcgaattat ttgatcacca aggtgcagag ccagccttct    3060
tattcggcct tgaattgatc atatgcggat tagaaaaaca acttaaatgt gaaagtgggt    3120
cttaaaagca gcataacctt tttccgtgat ggtaacttca ctagtttaaa aggatctagg    3180
tgaagatcct tttgataat ctcatgacca aaatccctta acgtgagttt tcgttccact    3240
gagcgtcaga ccccgtagaa aagatcaaag gatcttcttg agatcctttt tttctgcgcg    3300
taatctgctg cttgcaaaca aaaaaaccac cgctaccagc ggtggtttgt ttgccggatc    3360
aagagctacc aactctttt ccgaaggtaa ctggcttcag cagagcgcag ataccaaata    3420
ctgtccttct agtgtagccg tagttaggcc accacttcaa gaactctgta gcaccgccta    3480
catacctcgc tctgctaatc ctgttaccag tggctgctgc cagtggcgat aagtcgtgtc    3540
ttaccgggtt ggactcaaga cgatagttac cggataaggc gcagcggtcg ggctgaacgg    3600
ggggttcgtg cacacagccc agcttggagc gaacgaccta caccgaactg agatacctac    3660
agcgtgagct atgagaaagc gccacgcttc ccgaagggag aaaggcggac aggtatccgg    3720
taagcggcag ggtcggaaca ggagagcgca cgagggagct tccaggggga aacgcctggt    3780
atctttatag tcctgtcggg tttcgccacc tctgacttga gcgtcgattt tgtgatgct    3840 cgtcaggggg gcggagccta tggaaaaacg ccagcaacgc ggccttttta cggttcctgg    3900
ccttttgctg gccttttgct cacatgaccc gaca                              3934
```

<210> SEQ ID NO 78
<211> LENGTH: 54
<212> TYPE: DNA
<213> ORGANISM: Artificial Sequence
<220> FEATURE:
<223> OTHER INFORMATION: Synthetic primer

<400> SEQUENCE: 78

```
gggtctagaa aaggaggaat ttaaatgtta ctggttatcg atgtggggaa cacc          54
```

```
<210> SEQ ID NO 79
<211> LENGTH: 47
<212> TYPE: DNA
<213> ORGANISM: Artificial Sequence
<220> FEATURE:
<223> OTHER INFORMATION: Synthetic primer

<400> SEQUENCE: 79
gggatcctta tacacttcct acgcggtttc tttcataaat caattcc        47

<210> SEQ ID NO 80
<211> LENGTH: 48
<212> TYPE: DNA
<213> ORGANISM: Artificial Sequence
<220> FEATURE:
<223> OTHER INFORMATION: Synthetic primer

<400> SEQUENCE: 80
gggtctagaa aaggaggaat ttaaatgatt atcctcatcg actccggc       48

<210> SEQ ID NO 81
<211> LENGTH: 35
<212> TYPE: DNA
<213> ORGANISM: Artificial Sequence
<220> FEATURE:
<223> OTHER INFORMATION: Synthetic primer

<400> SEQUENCE: 81
gggatcctta ggccgttggc gcgccttgcg cggcg                     35

<210> SEQ ID NO 82
<211> LENGTH: 75
<212> TYPE: DNA
<213> ORGANISM: Artificial Sequence
<220> FEATURE:
<223> OTHER INFORMATION: Synthetic primer

<400> SEQUENCE: 82
gggtctagaa aaggaggaat ttaaatgaat aaacctttat tatcagaatt gataattgat    60
attggaaata ccagc                                           75

<210> SEQ ID NO 83
<211> LENGTH: 63
<212> TYPE: DNA
<213> ORGANISM: Artificial Sequence
<220> FEATURE:
<223> OTHER INFORMATION: Synthetic primer

<400> SEQUENCE: 83
gggatcctta attaacaaac ttaaagtcaa tagaatttcc taaaattcta acgccttcta    60
cag                                                        63

<210> SEQ ID NO 84
<211> LENGTH: 64
<212> TYPE: DNA
<213> ORGANISM: Artificial Sequence
<220> FEATURE:
<223> OTHER INFORMATION: Synthetic primer

<400> SEQUENCE: 84
gggtctagaa aaggaggaat ttaaatgcca gctaggcaat cttttacaga tttgaaaaac    60
ctgg                                                       64
```

-continued

```
<210> SEQ ID NO 85
<211> LENGTH: 58
<212> TYPE: DNA
<213> ORGANISM: Artificial Sequence
<220> FEATURE:
<223> OTHER INFORMATION: Synthetic primer

<400> SEQUENCE: 85
gggatcctta tttgcattct agtatccctg cttttttaag agcgatttcc atcccgtc        58

<210> SEQ ID NO 86
<211> LENGTH: 57
<212> TYPE: DNA
<213> ORGANISM: Artificial Sequence
<220> FEATURE:
<223> OTHER INFORMATION: Synthetic primer

<400> SEQUENCE: 86
gggtctagaa aaggaggaat ttaaatgatt cttgagctcg actgtggaaa ctcgctg         57

<210> SEQ ID NO 87
<211> LENGTH: 41
<212> TYPE: DNA
<213> ORGANISM: Artificial Sequence
<220> FEATURE:
<223> OTHER INFORMATION: Synthetic primer

<400> SEQUENCE: 87
gggatcctta ctcaatcggg caagccagtg ccagccctac g                         41
```